United States Patent
Schwink et al.

(10) Patent No.: US 8,586,609 B2
(45) Date of Patent: Nov. 19, 2013

(54) ARYL-SUBSTITUTED POLYCYCLIC AMINES, METHOD FOR THE PRODUCTION THEREOF, AND USE THEREOF AS A MEDICAMENT

(75) Inventors: Lothar Schwink, Stadtallendorf (DE); Siegfried Stengelin, Eppstein (DE); Matthias Gossel, Hofheim (DE); Gerhard Hessler, Hofheim (DE); Petra Lennig, Mainz (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 363 days.

(21) Appl. No.: 12/846,075

(22) Filed: Jul. 29, 2010

(65) Prior Publication Data

US 2010/0298378 A1 Nov. 25, 2010

Related U.S. Application Data

(60) Division of application No. 11/674,353, filed on Feb. 13, 2007, now Pat. No. 7,838,547, which is a continuation of application No. PCT/EP2005/008889, filed on Aug. 16, 2005.

(30) Foreign Application Priority Data

Aug. 16, 2004 (DE) .................... 10 2004 039 789

(51) Int. Cl.
| | |
|---|---|
| C07D 471/04 | (2006.01) |
| C07D 471/08 | (2006.01) |
| C07D 487/04 | (2006.01) |
| C07D 487/08 | (2006.01) |
| C07D 401/14 | (2006.01) |
| C07D 498/10 | (2006.01) |
| C07D 417/14 | (2006.01) |
| A61K 31/4545 | (2006.01) |
| A61K 31/407 | (2006.01) |
| A61K 31/454 | (2006.01) |
| A61K 31/424 | (2006.01) |
| A61K 31/4439 | (2006.01) |
| A61K 31/427 | (2006.01) |
| A61P 3/06 | (2006.01) |
| A61P 3/10 | (2006.01) |

(52) U.S. Cl.
USPC ........... 514/318; 514/322; 514/338; 514/365; 514/375; 514/412; 546/194; 546/199; 546/277.1; 548/204; 548/216; 548/453

(58) Field of Classification Search
None
See application file for complete search history.

(56) References Cited

U.S. PATENT DOCUMENTS

| 7,569,583 B2 * | 8/2009 | Schwink et al. ............... 514/306 |
| 7,838,547 B2 * | 11/2010 | Schwink et al. ............... 514/412 |
| 8,163,741 B2 * | 4/2012 | Schwink et al. ............ 514/233.2 |

FOREIGN PATENT DOCUMENTS

| EP | 1 249 233 A1 | 10/2002 |
| WO | WO 00/53591 | 9/2000 |
| WO | WO 01/57037 A1 | 8/2001 |
| WO | WO 03/015769 | 2/2003 |
| WO | WO 2005/002577 | 1/2005 |

OTHER PUBLICATIONS

Fahmy et al., caplus an 1987:32764.*
Gehlert et al., 2009, J. Pharmacol Exp Ther, abstract.*
SNAP-7941, 2013, http://en.wikipedia.org/wiki/SNAP-7941.*
Chen, Yanyun et al., "Targeted Disruption of the Melanin-Concentrating Hormone Receptor-1 Results in Hyperphagia and Resistance to Diet-Induced Obesity," Endocrinology (2002), vol. 143, pp. 2469-2477.
Winterfield, K. et al., "Synthese von 1-Hydroxy-2-chlorchinolizidin und 1-Hydroxy-2-amino-4-oxochinolizidin," Archiv der Pharmazie (1969), vol. 302, pp. 900-908.
Borowsky Beth et al., "Antidepessant, anxiolytic and anorectic effects of a melanin-concentrating hormone-1 receptor antagonist," Nature Medicine (2002), vol. 8, No. 8, pp. 825-830.
Hervieu, Guillaume, "Melanin-concentrating hormone functions in the nervous system: food intake and stress," Expert Opinion on Therapeutic Targets (2003), vol. 7, pp. 495-511.
Audinot, Valerie et al., "Structure-Activty Relationship Studies of Melanin-concentrating Hormone (MCH)-related Peptide Ligands at SLC-1, the Human MCH Receptor," The Journal of Biological Chemistry (2001), vol. 276, No. 17, pp. 13554-13562.
Qu, Daqing et al., "A role for melanin-concentrating hormone in the central regulation of feeding behaviour," Nature (1996), vol. 380, pp. 243-247.
Shimada, Masako et al., "Mice lacking melanin-concentrating hormone are hypophagic and lean," Nature (1998), vol. 396, pp. 670-674.
Pereira, Marcio et al., "Hypothalamic Melanin-Concentrating Hormone Is Induced by Cold Exposure and Particpates in the Control of Energy Expenditure in Rats," Endocrinology (2003), vol. 144, pp. 4831-4840.

* cited by examiner

*Primary Examiner* — Sun Jae Loewe
(74) *Attorney, Agent, or Firm* — Scully, Scott, Murphy & Presser, P.C.

(57) ABSTRACT

The invention relates to aryl-substituted polycyclic amines of formula I, especially bicyclic amines, and to the physiologically tolerated salts and physiologically functional derivatives thereof;

$$R2\diagdown_K\diagup^E\diagdown_X\diagup\overset{O}{\underset{|}{C}}\diagdown_N\diagup\overset{A=B}{\underset{G-D}{\diagdown}}-L-Q$$
$$\qquad\qquad\qquad\qquad R1$$

where the symbols and radicals are explained in the description, as well as to pharmaceutical compositions containing them and to methods of treatment using them.

14 Claims, No Drawings

ARYL-SUBSTITUTED POLYCYCLIC AMINES, METHOD FOR THE PRODUCTION THEREOF, AND USE THEREOF AS A MEDICAMENT

CROSS REFERENCE TO RELATED APPLICATIONS

This application is a divisional of U.S. application Ser. No. 11/674,353, filed Feb. 13, 2007, now allowed, which is a continuation of International application No. PCT/EP2005/008889, filed Aug. 16, 2005, both of which are incorporated herein by reference in their entirety; which claims the benefit of priority of German Patent Application No. 102004039789.9, filed Aug. 16, 2004.

FIELD OF THE INVENTION

The invention relates to aryl-substituted polycyclic amines, especially bicyclic amines, and to the physiologically tolerated salts and physiologically functional derivatives thereof.

The invention was based on the object of providing compounds which bring about a weight reduction in mammals and are suitable for the prevention and treatment of obesity and diabetes and the diverse sequelae thereof.

BACKGROUND OF THE INVENTION

Compounds which have a similar overall structure to the aryl-substituted polycyclic amines described herein and have a pharmacological effect have been described in the prior art. Thus, for example, WO2000053591 describes ureido-substituted azabicycles having an antiviral effect. WO2004024702 claims inter alia amidoalkylaryl-substituted azabicycles having MCH-antagonistic effect for the treatment of obesity.

Compounds having an MCH-antagonistic effect for the treatment of obesity are described in the prior art (examples: WO2001021577, WO2003035624, WO2002089729, WO2002006245, WO2002002744, WO2002057233, WO2003045313, WO2003097047, WO2002010146, WO2003087044).

SUMMARY OF THE INVENTION

Surprisingly, a series of compounds which modulate the activity of MCH receptors has been found. The compounds are distinguished In particular by antagonism of the MCH1R.

The invention therefore relates to compounds of the formula I

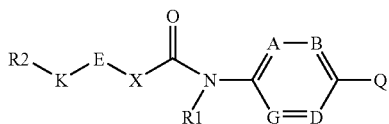

I in which the meanings are

A, B, D, G
independently of one another N, C(R3);
or
groups A and B or groups D and G are in each case C(R3) and form together a 5- or 6-membered carbocyclic or heterocyclic radical to result overall in a bicyclic system;

R3 H, F, Cl, Br, I, OH, $CF_3$, $NO_2$, CN, $OCF_3$, O—($C_1$-$C_6$)-alkyl, O—($C_1$-$C_4$)-alkoxy-($C_1$-$C_4$)-alkyl, S—($C_1$-$C_6$)-alkyl, ($C_1$-$C_6$)-alkyl, ($C_2$-$C_6$)-alkenyl, ($C_3$-$C_8$)-cycloalkyl, O—($C_3$-$C_8$)-cycloalkyl, ($C_3$-$C_8$)-cycloalkenyl, ($C_2$-$C_6$)-alkynyl, ($C_0$-$C_8$)-alkylene-aryl, O—($C_0$-$C_8$)-alkylene-aryl, S-aryl, N(R4)(R5), $SO_2$—$CH_3$, COOH, COO—($C_1$-$C_6$)-alkyl, CON(R6)(R7), N(R8)CO(R9), N(R10)$SO_2$(R11), CO(R12), (CR13R14)$_x$—O(R15);

R4, R5, R6, R7, R8, R10
independently of one another H, ($C_1$-$C_8$)-alkyl;
or
R4 and R5, R6 and R7
independently of one another optionally together with the nitrogen atom to which they are bonded a 5-6 membered ring which, apart from the nitrogen atom, may also include 0-1 further heteroatoms from the group of NH, N—($C_1$-$C_6$)-alkyl, oxygen and sulfur;

R9, R11, R12
independently of one another H, ($C_1$-$C_8$)-alkyl, aryl;

R13, R14
independently of one another H, ($C_1$-$C_8$)-alkyl;

R15 H, ($C_1$-$C_6$)-alkyl, aryl;

x 0, 1, 2, 3, 4, 5, 6;

R1 H, ($C_1$-$C_8$)-alkyl, ($C_3$-$C_6$)-alkenyl, ($C_3$-$C_6$)-alkynyl;

X N(R16), O, a bond, (R17)C=C(R18), C=O, a group of the formula (CR19R20)$_y$, in which one or two (CR19R20) groups may be replaced by Y to result in a chemically reasonable radical;

Y O, S, N(R21), C=O;

R16, R17, R18
independently of one another H, ($C_1$-$C_8$)-alkyl;

R19, R20
independently of one another H, ($C_1$-$C_4$)-alkyl, where R19 and R20 in the y groups may in each case have identical or different meanings;

y 1, 2, 3, 4, 5, 6;

R21 H, ($C_1$-$C_8$)-alkyl;

E 3-14 membered bivalent carbo- or heterocyclic ring structure having 0-4 heteroatoms from the group of N, O and S, which may optionally have substituents from the group of H, F, Cl, Br, I, OH, $CF_3$, $NO_2$, CN, $OCF_3$, oxo, O—($C_1$-$C_6$)-alkyl, O—($C_1$-$C_4$)-alkoxy-($C_1$-$C_4$)-alkyl, S—($C_1$-$C_6$)-alkyl, ($C_1$-$C_6$)-alkyl, ($C_2$-$C_6$)-alkenyl, ($C_3$-$C_8$)-cycloalkyl, O—($C_3$-$C_8$)-cycloalkyl, ($C_3$-$C_8$)-cycloalkenyl, O—($C_3$-$C_8$)-cycloalkenyl, ($C_2$-$C_6$)-alkynyl, ($C_0$-$C_8$)-alkylene-aryl, O—($C_0$-$C_8$)-alkylene-aryl, S-aryl, N(R22)(R23), $SO_2$—$CH_3$, COOH, COO—($C_1$-$C_6$)-alkyl, CON(R24)(R25), N(R26)CO(R27), N(R28)$SO_2$(R29), CO(R30) and be mono- or bicyclic;

R22, R23, R24, R25, R26, R28
independently of one another H, ($C_1$-$C_8$)-alkyl, aryl;
or
R22 and R23, R24 and R25
independently of one another optionally together with the nitrogen atom to which they are bonded a 5-6 membered ring which, apart from the nitrogen atom, may also include 0-1 further heteroatoms from the group of NH, N—($C_1$-$C_6$)-alkyl, oxygen and sulfur;

R27, R29, R30
independently of one another H, ($C_1$-$C_8$)-alkyl, aryl;

K a bond, C=C, (R31)C=C(R32), a group of the formula (CR33R34)$_z$ in which one or more (CR33R34) groups may be replaced by Z to result in a chemically reasonable radical, preferably a bond, O, $OCH_2$, $CH_2O$, S, SO, $SO_2$, N(R35), N(R36)CO, CON(R37), (C(R38)(R39))$_v$, CO, (R31)C=C(R32), C=C, $SCH_2$, $SO_2CH_2$;

v 1, 2, 3, 4;

R31, R32, R35, R36, R37, R38, R39
  independently of one another H, $(C_1-C_8)$-alkyl;

Z O, S, N(R40), CO, SO, $SO_2$;

R33, R34
  independently of one another H, $(C_1-C_8)$-alkyl, hydroxy-$(C_1-C_4)$-alkyl, hydroxy, $(C_1-C_4)$-alkoxy-$(C_1-C_4)$-alkyl, where R38 and R39 in the z groups may in each case have identical or different meanings;

z 1, 2, 3, 4, 5, 6;

R40 H, $(C_1-C_8)$-alkyl;

R2 H, $(C_1-C_8)$-alkyl, $(C_1-C_8)$-alkoxy-$(C_1-C_4)$-alkyl, $(C_3-C_8)$-alkenyl, $(C_3-C_8)$-alkynyl, a 3 to 10-membered mono-, bi-, tri- or spirocyclic ring which may include 0 to 4 heteroatoms selected from the group of oxygen, nitrogen and sulfur, where the ring system may additionally be substituted by one or more of the following substituents: F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, $(C_0-C_8)$-alkylene-aryl, oxo, CO(R41), CON(R42)(R43), hydroxy, COO(R44), N(R45)CO$(C_1-C_6)$-alkyl, N(R46)(R47), $SO_2CH_3$, $SCF_3$ or S—$(C_1-C_6)$-alkyl;

R41, R42, R43, R44, R45, R46, R47
  independently of one another H, $(C_1-C_8)$-alkyl;
or
R42 and R43, R46 and R47
  form independently of one another optionally together with the nitrogen atom to which they are bonded a 5-6 membered ring which, apart from the nitrogen atom, may also include 0-1 further heteroatoms from the group of NH, N—$(C_1-C_6)$-alkyl, oxygen and sulfur;

E, K and R2
  together form a tricyclic system where the rings may independently of one another be saturated, partially saturated or unsaturated and in each case may comprise 3-8 ring atoms;

Q bi-, tri- or spirocyclic saturated or partially unsaturated ring structure having one nitrogen atom and 0-3 further heteroatoms selected from the group of N, O and S, where the rings of the structure may be spiro-linked, fused or bridged, and where the ring system may be substituted by one or more of the following substituents: F, OH, $CF_3$, CN, $OCF_3$, oxo, O—$(C_1-C_8)$-alkyl, $(C_1-C_4)$-alkoxy-$(C_1-C_4)$-alkyl, $(C_1-C_6)$-alkyl, $(C_2-C_6)$-alkenyl, $(C_2-C_6)$-alkynyl, CO(R51), $(CR52R53)_o$-R54, $CO(CR52R53)_p$-R55;

R51 H, $(C_1-C_8)$-alkyl;

R52, R53
  independently of one another H, $(C_1-C_8)$-alkyl, OH, $(C_3-C_8)$-cycloalkyl, $(C_1-C_4)$-alkoxy-$(C_1-C_4)$alkyl;

o, p independently of one another 0, 1, 2, 3, 4, 5, 6;

R54, R55
  independently of one another OH, O—$(C_1-C_8)$-alkyl, CON(R56)(R57), N(R58)CO(R59), N(R60)(R61), $CO_2$(R62), $SO_2$Me, CN, a 3-10 membered ring system having 0 to 3 heteroatoms selected from the group of N, O and S, which may be substituted by one or more of the following substituents: F, Cl, Br, $CF_3$, $(C_1-C_8)$-alkyl, O—$(C_1-C_8)$-alkyl, CO(R63), oxo, OH;

R56, R57, R58, R59, R62, R63
  independently of one another H, $(C_1-C_8)$-alkyl;
or
R56 and R57
  form optionally together with the nitrogen atom to which they are bonded a 5-6 membered ring which, apart from the nitrogen atom, may also include 0-1 further heteroatoms from the group of NH, N—$(C_1-C_6)$-alkyl, oxygen and sulfur;

R60, R61
  independently of one another H, $(C_1-C_6)$-alkyl, $(C_1-C_4)$-alkoxy-$(C_1-C_4)$-alkyl, $(C_2-C_6)$-alkenyl, $(C_2-C_6)$-alkynyl, CO(R64), $(CR65R66)_q$-R67, $CO(CR68R69)_r$-R70; or R60 and R61 form together with the nitrogen atom to which they are bonded a 4 to 10-membered mono-, bi- or spirocyclic ring which, apart from the nitrogen atom, comprises 0 to 3 additional heteroatoms selected from the group of N, O and S and may additionally be substituted by one or more of the following substituents: F, Cl, Br, $CF_3$, O—$(C_1-C_8)$-alkyl, $(C_1-C_6)$-alkyl, CO(R71), oxo, OH, $(C_1-C_4)$-alkoxy-$(C_1-C_4)$-alkyl, hydroxy-$(C_1-C_4)$-alkyl, CON(R72)(R73), N(R74)CO(R75), N(R76)(R77), $CO_2$(R78), $SO_2$Me;

R64, R65, R66, R68, R69, R71, R72, R73, R74, R75, R76, R77, R78
  independently of one another H, $(C_1-C_8)$-alkyl;
or
R76 and R77
  form optionally together with the nitrogen atom to which they are bonded a 5-6 membered ring which, apart from the nitrogen atom, may also include 0-1 further heteroatoms from the group of NH, N—$(C_1-C_6)$-alkyl, oxygen and sulfur;

q, r independently of one another 0, 1, 2, 3, 4, 5, 6;

R67, R70
  independently of one another OH, O—$(C_1-C_8)$-alkyl, CON(R79)(R80), N(R81)CO(R82), N(R83)(R84), $CO_2$(R85), $SO_2$Me, CN, a 3-10 membered ring system having 0 to 3 heteroatoms selected from the group of N, O and S, which may be substituted by F, Cl, Br, $CF_3$, $(C_1-C_8)$-alkyl, O—$(C_1-C_8)$-alkyl, CO(R86), oxo, OH;

R79, R80, R81, R82, R83, R84, R85, R86
  independently of one another H, $(C_1-C_8)$-alkyl;
or
R79 and R80, R83 and R84
  form independently of one another optionally together with the nitrogen atom to which they are bonded a 5-6 membered ring which, apart from the nitrogen atom, may also include 0-1 further heteroatoms from the group of NH, N—$(C_1-C_6)$-alkyl, oxygen and sulfur;

the N-oxides thereof and the physiologically tolerated salts thereof.

The invention relates to compounds of the formula I in the form of their racemates, enantiomer-enriched mixtures and pure enantiomers and to their diastereomers and mixtures thereof.

DETAILED DESCRIPTION

The compounds of the formula I are distinguished by improved metabolic stability combined with high activity compared with compounds of similar structure.

The alkyl, alkenyl and alkynyl radicals in the substituents R1, R2, R3, R4, R5, R6, R7, R8, R9, R10, R11, R12, R13, R14, R15, R16, R17, R18, R19, R20, R21, R22, R23, R24, R25, R26, R27, R28, R29, R30, R31, R32, R33, R34, R35, R36, R37, R38, R39, R40, R41, R42, R43, R44, R45, R46, R47, R51, R52, R53, R54, R55, R56, R57, R58, R59, R60, R61, R62, R63, R64, R65, R66, R67, R68, R69, R70, R71, R72, R73, R74, R75, R76, R77, R78, R79, R80, R81, R82, R83, R84, R85, R86, R87, R88, R89 and R90 may be either straight-chain, branched and/or optionally substituted by substituents such as aryl, heteroaryl, alkoxy or halogen. This also applies if the alkyl, alkenyl and alkynyl radicals are part of another group, e.g. part of an alkoxy group (such as ($C_1$-$C_4$)-alkoxy-($C_1$-$C_4$-alkyl)). Suitable halogens are fluorine, chlorine, bromine and iodine, preferably fluorine, chlorine and bromine, particularly preferably fluorine.

Examples of alkyl groups are: methyl, ethyl, propyl, butyl, pentyl, hexyl, heptyl and octyl. Included therein are both the n isomers of these radicals and branched isomers such as isopropyl, isobutyl, isopentyl, sec-butyl, tert-butyl, neopentyl, 3,3-dimethylbutyl etc. Unless described otherwise, the term alkyl additionally includes alkyl radicals which are unsubstituted or optionally substituted by one or more further radicals, for example 1, 2, 3 or 4 identical or different radicals such as aryl, heteroaryl, ($C_1$-$C_4$)-alkoxy or halogen. It is moreover possible for the additional substituents to occur in any position of the alkyl radical. The alkyl radicals are preferably unsubstituted, unless defined otherwise.

Cycloalkyl means for the purposes of the present application cycloalkyl and cycloalkyl-alkyl (alkyl which is in turn substituted by cycloalkyl), with cycloalkyl having at least 3 carbon atoms. Examples of cycloalkyl radicals are: cyclopropyl, cyclobutyl, cyclopentyl, cyclohexyl, cycloheptyl, cyclooctyl, cyclononyl and cyclodecyl. Polycyclic ring systems are also possible where appropriate, such as decalinyl, norbornanyl, bornanyl or adamantanyl. The cycloalkyl radicals may be unsubstituted or optionally substituted by one or more further radicals as detailed by way of example above for the alkyl radicals. The cycloalkyl radicals are preferably unsubstituted, unless defined otherwise.

Examples of alkenyl and alkynyl groups are: vinyl, 1-propenyl, 2-propenyl (allyl), 2-butenyl, 2-methyl-2-propenyl, 3-methyl-2-butenyl, ethynyl, 2-propynyl(propargyl), 2-butynyl or 3-butynyl.

Cycloalkenyl means for the purposes of the present application cycloalkenyl radicals and cycloalkenyl-alkyl radicals (alkyl which is substituted by cycloalkenyl) which comprise at least three carbon atoms. Examples of cycloalkenyl are: cyclopentenyl, cyclohexenyl, cycloheptenyl and cyclooctenyl.

The alkenyl radicals and cycloalkenyl radicals may have one to three conjugated or unconjugated double bonds (that is also alk-dienyl and alk-trienyl radicals), preferably one double bond in a straight or branched chain. The same applies to the triple bonds in alkynyl radicals. The alkenyl and alkynyl radicals may be unsubstituted or optionally substituted by one or more further radicals as detailed by way of example for the alkyl radicals above. The alkenyl and alkynyl radicals are preferably unsubstituted, unless defined otherwise.

Aryl refers in the present invention to radicals derived from monocyclic or bicyclic aromatic systems comprising no ring heteroatoms. Where the systems are not monocyclic, the term aryl includes for the second ring also the saturated form (perhydro form) or the partially unsaturated form (for example the dihydro form or tetrahydro form) where the respective forms are known and stable. The term aryl also includes in the present invention for example bicyclic radicals in which both the rings are aromatic and bicyclic radicals in which only one ring is aromatic. Examples of aryl are: phenyl, naphthyl, indanyl, 1,2-dihydronaphthenyl, 1,4-dihydronaphthenyl, indenyl or 1,2,3,4-tetrahydronaphthyl. The aryl radicals are preferably unsubstituted, unless defined otherwise. Aryl is particularly preferably phenyl or naphthyl.

Heteroaryl radicals mean radicals derived from monocyclic or bicyclic aromatic systems which comprise ring heteroatoms, preferably N, O or S. Otherwise, that stated concerning aryl radicals applies to the heteroaryl radicals.

A "tricyclic system" means structures having 3 rings which are connected together by more than one bond. Examples of such systems are fused systems having 3 rings and spirocyclic systems having a fused-on ring system.

The bivalent carbo- or heterocyclic ring structure E also includes structures which are linked via one and the same atom to the two adjacent groups K and X.

A polycyclic group means for the purposes of the present application a group derived from spiranes, fused ring systems or bridged ring systems. Spiranes are distinguished by two rings having only one carbon atom in common and the ring planes of the two rings being perpendicular to one another. In the fused ring systems, two rings are linked together so that they have two atoms in common. This type of linkage involves an "ortho fusion". Bridged ring systems are ring systems which have a bridge of carbon atoms and/or heteroatoms between two nonadjacent atoms of a ring.

A "chemically reasonable radical" means for the purposes of the present invention a radical which is stable at room temperature and atmospheric pressure. For the purposes of the present invention a "chemically reasonable radical" in the definitions of the groups X and K in the compounds of the formula (I) is preferably understood to be groups of the formula (CR19R20)$_y$ (in the definition of X) or (CR33R34), (in the definition of K), which have no heteroatom-heteroatom bonds between the individual groups (CR19R20) or (CR33R34).

The compounds of the formula I may have one or more centers of asymmetry. The compounds of the formula I may therefore exist in the form of their racemates, enantiomer-enriched mixtures, pure enantiomers, diastereomers and mixtures of diastereomers. The present invention encompasses all these isomeric forms of the compounds of the formula I. These isomeric forms may be obtained by known methods, even if not expressly described in some cases.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts), alkaline earth metal salts (such as magnesium and calcium salts) and salts of trometamol (2-amino-2-hydroxymethyl-1,3-propanediol), diethanolamine, lysine or ethylenediamine.

Salts with a pharmaceutically unacceptable anion, such as, for example, trifluoro acetate, likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the formula I of the invention, for example an ester, which on administration to a mammal such as, for example, a human is able to form (directly or indirectly) a compound of the formula I or an active metabolite thereof.

Physiologically functional derivatives also include prodrugs of the compounds of the invention, as described, for example, in H. Okada et al., Chem. Pharm. Bull. 1994, 42, 57-61. Such prodrugs can be metabolized in vivo to a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) of the formula I as described above, and their salts, solvates and physiologically functional derivatives as described herein.

If radicals or substituents may occur more than once in the compounds of the formula I, they may all have the stated meanings independently of one another and be identical or different.

The symbols in compound I preferably have the following meanings:

A, B, D, G
  independently of one another N, C(R3) or groups A and B or D and G are each C(R3) and form together an orthophenylene unit to result overall in a 1,4-disubstituted naphthalene system; preferably independently of one another N or C(R3), where the total number of nitrogen atoms in the ring is 0-2, preferably 0 or 1, particularly preferably C(R3);

R3 H, F, Cl, Br, $CF_3$, CN, O—$(C_1$-$C_8)$-alkyl, O—$(C_1$-$C_4)$-alkoxy-$(C_1$-$C_4)$-alkyl, S—$(C_1$-$C_6)$-alkyl, $(C_1$-$C_6)$-alkyl, $(C_0$-$C_8)$-alkylene-aryl, O—$(C_0$-$C_8)$-alkylene-aryl, N(R4)(R5), $SO_2$—$CH_3$, CON(R6)(R7), N(R8)CO(R9), CO(R12), $(CR13R14)_x$—O(R15); preferably H, F, Cl, Br, $CF_3$, CN, O—$(C_1$-$C_8)$-alkyl, $(C_1$-$C_8)$-alkyl, $SO_2$—$CH_3$, CON(R6)(R7), N(R8)CO(R9), CO(R12), $(CR13R14)_x$—O(R15), particularly preferably H, F, Cl, $CF_3$, CN, $(C_1$-$C_8)$-alkyl, $(C(R13)(R14))_x$—O(R15); very particularly preferably H, F, Cl, $(C_1$-$C_8)$-alkyl;

R4, R5, R6, R7, R8
  independently of one another H, $(C_1$-$C_8)$-alkyl;
or
R4 and R5, R6 and R7
  form independently of one another optionally together with the nitrogen atom to which they are bonded a 5-6 membered ring which, apart from the nitrogen atom, may also include 0-1 further heteroatoms from the group of NH, N—$(C_1$-$C_8)$-alkyl, oxygen and sulfur;

R9, R12
  independently of one another H, $(C_1$-$C_8)$-alkyl;

R13, R14
  H;

R15 H, $(C_1$-$C_6)$-alkyl;

x 0, 1, 2, preferably 0, 1, particularly preferably 1;

R1 H, $(C_1$-$C_8)$-alkyl;

X N(R16), a bond, (R17)C=C(R18), C≡C, $CH_2$—$CH_2$, $YCH_2$, $CH_2Y$, preferably N(R16), a bond;

Y O, S, N(R21);

R16, R17, R18
  independently of one another H, $(C_1$-$C_8)$-alkyl; preferably H;

R21 H, $(C_1$-$C_8)$-alkyl;

E 3-8 membered bivalent carbo- or heterocyclic ring structure having 0-4 heteroatoms from the group of N, O and S, which may optionally have substituents from the group of H, F, Cl, Br, OH, $CF_3$, $NO_2$, CN, $OCF_3$, O—$(C_1$-$C_6)$-alkyl, O—$(C_1$-$C_4)$-alkoxy-$(C_1$-$C_4)$-alkyl, S—$(C_1$-$C_6)$-alkyl, $(C_1$-$C_6)$-alkyl, $(C_2$-$C_6)$-alkenyl, O—$(C_3$-$C_8)$-cycloalkyl, $(C_3$-$C_8)$-cycloalkenyl, $(C_2$-$C_6)$-alkynyl, $(C_0$-$C_8)$-alkylene-aryl, O—$(C_0$-$C_8)$-alkylene-aryl, S-aryl, N(R22)(R23), $SO_2$—$CH_3$, N(R26)CO(R27), N(R28)$SO_2$(R29), CO(R30) and be mono- or bicyclic;

preferably 5-7 membered bivalent carbo- or heterocyclic ring structure having 0-3 heteroatoms from the group of N, O and S, which may optionally have substituents from the group of H, F, Cl, Br, OH, $CF_3$, $NO_2$, CN, $OCF_3$, O—$(C_1$-$C_6)$-alkyl, S—$(C_1$-$C_6)$-alkyl, $(C_1$-$C_6)$-alkyl, $(C_2$-$C_6)$-alkenyl, O—$(C_0$-$C_8)$-alkylene-aryl, S-aryl, N(R22)(R23), $SO_2$—$CH_3$, N(R26)CO(R27), CO(R30) and be mono- or bicyclic;

particularly preferably 5-7 membered bivalent carbo- or heterocyclic ring structure having 0-2 heteroatoms from the group of N, O and S, which may optionally have substituents from the group of H, F, Cl, Br, OH, $CF_3$, $NO_2$, $OCF_3$, O—$(C_1$-$C_6)$-alkyl, $(C_1$-$C_6)$-alkyl, $(C_2$-$C_6)$-alkenyl, N(R22)(R23), $SO_2$—$CH_3$, CO(R30), preferably H, F, Cl, Br, OH, $CF_3$, $(C_1$-$C_6)$-alkyl, O—$(C_1$-$C_6)$-alkyl, e.g. E is selected from the group consisting of which may optionally have substituents from the group of H, F, Cl, Br, OH, $CF_3$, $NO_2$, $OCF_3$, O—$(C_1$-$C_6)$-alkyl, $(C_1$-$C_6)$-alkyl, $(C_2$-$C_6)$-alkenyl, N(R22)(R23), $SO_2$—$CH_3$, CO(R30), preferably H, F, Cl, Br, OH, $CF_3$, $(C_1$-$C_6)$-alkyl, O—$(C_1$-$C_6)$-alkyl;

preferably

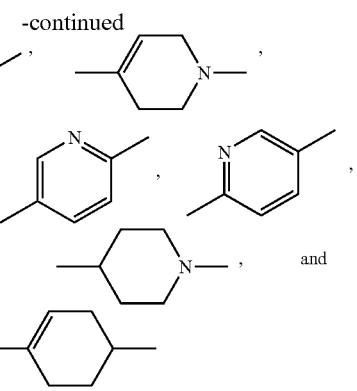

which may optionally have the aforementioned substituents;

R22, R23, R24, R25, R26, R28
independently of one another H, $(C_1-C_8)$-alkyl;
or
R22 and R23, R24 and R25
independently of one another optionally together with the nitrogen atom to which they are bonded a 5-6 membered ring which, apart from the nitrogen atom, may also include 0-1 further heteroatoms from the group of NH, N—$(C_1-C_6)$-alkyl, oxygen and sulfur;

R27, R29, R30
independently of one another H, $(C_1-C_8)$-alkyl;

K a bond, O, OCH$_2$, CH$_2$O, S, SO, SO$_2$, N(R35), N(R36)CO, N—SO$_2$, CON(R37), (C(R38)(R39))$_v$, CO, (R31)C=C(R32), C≡C, SCH$_2$, SO$_2$CH$_2$, preferably a bond, O, OCH$_2$, CH$_2$O, S, SO, SO$_2$, N(R35), N(R36)CO, CON(R37), (C(R38)(R39))$_v$, CO, (R31)C=C(R32), C≡C, SCH$_2$, SO$_2$CH$_2$, particularly preferably OCH$_2$, CH$_2$O, N(R36)CO, CON(R37), (C(R38)(R39))$_2$, (R31)C=C(R32), C≡C, SCH$_2$, SO$_2$CH$_2$, very particularly preferably OCH$_2$, CH$_2$O, CON(R37), C≡C, SCH$_2$;

v 1, 2, 3, preferably 2;

R31, R32, R35, R36, R37, R38, R39
independently of one another H, $(C_1-C_8)$-alkyl;

R2 $(C_1-C_8)$-alkyl, $(C_1-C_4)$-alkoxy-$(C_1-C_4)$-alkyl, a 3 to 10-membered mono-, bi-, tri- or spirocyclic ring which may include 0 to 3 heteroatoms selected from the group of oxygen, nitrogen and sulfur, where the ring system may additionally be substituted by one or more of the following substituents: F, Cl, Br, CF$_3$, CN, $(C_1-C_6)$-alkyl, O—$(C_1-C_8)$-alkyl, $(C_0-C_2)$-alkylene-aryl, oxo, CO(R41), CON(R42)(R43), hydroxy, N(R45)CO$(C_1-C_6)$-alkyl, N(R46)(R47) or SO$_2$CH$_3$; preferably $(C_1-C_8)$-alkyl, $(C_1-C_4)$-alkoxy-$(C_1-C_4)$-alkyl, a 3 to 10-membered mono- or bicyclic ring which may include 0 to 2 heteroatoms selected from the group of oxygen, nitrogen and sulfur, where the ring system may additionally be substituted by one or more of the following substituents: F, Cl, Br, CF$_3$, CN, $(C_1-C_6)$-alkyl, O—$(C_1-C_8)$-alkyl, oxo, CO(R41), CON(R42)(R43), N(R45)CO$(C_1-C_6)$-alkyl or SO$_2$CH$_3$, R41, R42, R43, R45, R46, R47
independently of one another H, $(C_1-C_8)$-alkyl;
or
R42 and R43, R46 and R47
form independently of one another optionally together with the nitrogen atom to which they are bonded a 5-6 membered ring which, apart from the nitrogen atom, may also include 0-1 further heteroatoms from the group of NH, N—$(C_1-C_6)$-alkyl, oxygen and sulfur;

Q bi-, tri- or spirocyclic saturated or partially unsaturated ring structure having one nitrogen atom and 0-3 further heteroatoms selected from the group of N, O and S, where the rings of the structure may be spiro-linked, fused or bridged, and where the ring system may be substituted by one or more of the following substituents: F, OH, CF$_3$, CN, OCF$_3$, oxo, O—$(C_1-C_8)$-alkyl, $(C_1-C_4)$-alkoxy-$(C_1-C_4)$-alkyl, $(C_1-C_6)$-alkyl, $(C_2-C_6)$-alkenyl, $(C_2-C_6)$-alkynyl, CO(R51), (CR52R53)$_o$-R54, CO(CR52R53)$_p$-R55;

R51 H, $(C_1-C_8)$-alkyl;

R52, R53
independently of one another H, $(C_1-C_8)$-alkyl, OH, $(C_3-C_8)$-cycloalkyl, $(C_1-C_4)$-alkoxy-$(C_1-C_4)$alkyl;

o, p independently of one another 0, 1, 2, 3, 4, 5, 6;

R54, R55
independently of one another OH, O—$(C_1-C_8)$-alkyl, CON(R56)(R57), N(R58)CO(R59), N(R60)(R61), CO$_2$(R62), SO$_2$Me, CN, a 3-10 membered ring system having 0 to 3 heteroatoms selected from the group of N, O and S, which may be substituted by one or more of the following substituents: F, Cl, Br, CF$_3$, $(C_1-C_8)$-alkyl, O—$(C_1-C_8)$-alkyl, CO(R63), oxo, OH;

R56, R57, R58, R59, R62, R63
independently of one another H, $(C_1-C_8)$-alkyl;
or
R56 and R57
form optionally together with the nitrogen atom to which they are bonded a 5-6 membered ring which, apart from the nitrogen atom, may also include 0-1 further heteroatoms from the group of NH, N—$(C_1-C_6)$-alkyl, oxygen and sulfur;

R60, R61
independently of one another H, $(C_1-C_6)$-alkyl, $(C_1-C_4)$-alkoxy-$(C_1-C_4)$-alkyl, $(C_2-C_6)$-alkenyl, $(C_2-C_6)$-alkynyl, CO(R64), (CR65R66)$_q$-R67, CO(CR68R69)$_r$-R70;
or R60 and R61 form together with the nitrogen atom to which they are bonded a 4 to 10-membered mono-, bi- or spirocyclic ring which, apart from the nitrogen atom, comprises 0 to 3 additional heteroatoms selected from the group of N, O and S and may additionally be substituted by one or more of the following substituents: F, Cl, Br, CF$_3$, O—$(C_1-C_8)$-alkyl, $(C_1-C_6)$-alkyl, CO(R71), oxo, OH, $(C_1-C_4)$-alkoxy-$(C_1-C_4)$-alkyl, hydroxy-$(C_1-C_4)$-alkyl, CON(R72)(R73), N(R74)CO(R75), N(R76)(R77), CO$_2$(R78), SO$_2$Me;

R64, R65, R66, R68, R69, R71, R72, R73, R74, R75, R76, R77, R78
independently of one another H, $(C_1-C_8)$-alkyl;
or
R76 and R77
form optionally together with the nitrogen atom to which they are bonded a 5-6 membered ring which, apart from the nitrogen atom, may also include 0-1 further heteroatoms from the group of NH, N—$(C_1-C_6)$-alkyl, oxygen and sulfur;

q, r independently of one another 0, 1, 2, 3, 4, 5, 6;

R67, R70
independently of one another OH, O—$(C_1-C_8)$-alkyl, CON(R79)(R80), N(R81)CO(R82), N(R83)(R84), CO$_2$(R85), SO$_2$Me, CN, a 3-10 membered ring system having 0 to 3 heteroatoms selected from the group of N, O and S, which may be substituted by one or more of the following substituents: F, Cl, Br, CF$_3$, $(C_1-C_8)$-alkyl, O—$(C_1-C_8)$-alkyl, CO(R86), oxo, OH;

R79, R80, R81, R82, R83, R84, R85, R86
  independently of one another H, $(C_1\text{-}C_8)$-alkyl;
or
R79 and R80, R83 and R84
  form independently of one another optionally together with the nitrogen atom to which they are bonded a 5-6 membered ring which, apart from the nitrogen atom, may also include 0-1 further heteroatoms from the group of NH, N—$(C_1\text{-}C_6)$-alkyl, oxygen and sulfur.

Particularly preferred compounds of the formula I are those in which
A, B, D, G are independently of one another N or C(R3), and the total number of nitrogen atoms in this ring is 0-2, preferably 0 or 1, particularly preferably 0.

The linkage between the group

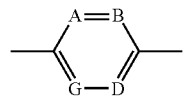

and Q preferably takes place via a nitrogen atom located within the ring structure Q.

In one embodiment of the present invention, Q in the compounds of the formula I is
a bi-, tri- or spirocyclic saturated or partially unsaturated ring structure having one nitrogen atom and 0-3 further heteroatoms selected from the group of N, O and S, where the rings of the structure may be spiro-linked, fused or bridged, and where the ring system may be substituted by one or more of the following substituents: F, OH, $CF_3$, CN, $OCF_3$, O—$(C_1\text{-}C_8)$-alkyl, $(C_1\text{-}C_4)$-alkoxy-$(C_1\text{-}C_4)$-alkyl, $(C_1\text{-}C_6)$-alkyl, $(C_2\text{-}C_6)$-alkenyl, $(C_2\text{-}C_6)$-alkynyl, CO(R51), (CR52R53)$_o$-R54, CO(CR52R53)$_p$-R55;
in which the meanings are
R51 H, $(C_1\text{-}C_8)$-alkyl;
R52, R53
  independently of one another H, $(C_1\text{-}C_8)$-alkyl, OH, $(C_3\text{-}C_8)$-cycloalkyl, $(C_1\text{-}C_4)$-alkoxy-$(C_1\text{-}C_4)$alkyl;
o, p independently of one another 0, 1, 2, 3, 4, 5, 6;
R54, R55
  independently of one another OH, O—$(C_1\text{-}C_8)$-alkyl, CON(R56)(R57), N(R58)CO(R59), N(R60)(R61), $CO_2$(R62), $SO_2Me$, CN, a 3-10 membered ring system having 0 to 3 heteroatoms selected from the group of N, O and S, which may be substituted by one or more of the following substituents: F, Cl, Br, $CF_3$, $(C_1\text{-}C_8)$-alkyl, O—$(C_1\text{-}C_8)$-alkyl, CO(R63), OH;
R56, R57, R58, R59, R62, R63
  independently of one another H, $(C_1\text{-}C_8)$-alkyl;
or
R56 and R57
  form optionally together with the nitrogen atom to which they are bonded a 5-6 membered ring which, apart from the nitrogen atom, may also include 0-1 further heteroatoms from the group of NH, N—$(C_1\text{-}C_6)$-alkyl, oxygen and sulfur;
R60, R61
  independently of one another H, $(C_1\text{-}C_6)$-alkyl, $(C_1\text{-}C_4)$-alkoxy-$(C_1\text{-}C_4)$-alkyl, $(C_2\text{-}C_6)$-alkenyl, $(C_2\text{-}C_6)$-alkynyl, CO(R64), (CR65R66)$_q$-R67, CO(CR68R69)$_r$-R70; or R60 and R61 form together with the nitrogen atom to which they are bonded a 4 to 10-membered mono-, bi- or spirocyclic ring which, apart from the nitrogen atom, comprises 0 to 3 additional heteroatoms selected from the group of N, O and S and may additionally be substituted by one or more of the following substituents: F, Cl, Br, $CF_3$, O—$(C_1\text{-}C_8)$-alkyl, $(C_1\text{-}C_6)$-alkyl, CO(R71), oxo, OH, $(C_1\text{-}C_4)$-alkoxy-$(C_1\text{-}C_4)$-alkyl, hydroxy-$(C_1\text{-}C_4)$-alkyl, CON(R72)(R73), N(R74)CO(R75), N(R76)(R77), $CO_2(R78)$, $SO_2Me$;
R64, R65, R66, R68, R69, R71, R72, R73, R74, R75, R76, R77, R78
  independently of one another H, $(C_1\text{-}C_8)$-alkyl;
or
R76 and R77
  form optionally together with the nitrogen atom to which they are bonded a 5-6 membered ring which, apart from the nitrogen atom, may also include 0-1 further heteroatoms from the group of NH, N—$(C_1\text{-}C_6)$-alkyl, oxygen and sulfur;
q, r independently of one another 0, 1, 2, 3, 4, 5, 6;
R67, R70
  independently of one another OH, O—$(C_1\text{-}C_8)$-alkyl, CON(R79)(R80), N(R81)CO(R82), N(R83)(R84), $CO_2$(R85), $SO_2Me$, CN, a 3-10 membered ring system having 0 to 3 heteroatoms selected from the group of N, O and S, which may be substituted by F, Cl, Br, $CF_3$, $(C_1\text{-}C_8)$-alkyl, O—$(C_1\text{-}C_8)$-alkyl, CO(R86), oxo, OH;
R79, R80, R81, R82, R83, R84, R85, R86
  independently of one another H, $(C_1\text{-}C_8)$-alkyl;
or
R79 and R80, R83 and R84
  form independently of one another optionally together with the nitrogen atom to which they are bonded a 5-6 membered ring which, apart from the nitrogen atom, may also include 0-1 further heteroatoms from the group of NH, N—$(C_1\text{-}C_6)$-alkyl, oxygen and sulfur.

In a further embodiment of the present invention, Q in the compounds of the formula I is
a bi-, tri- or spirocyclic saturated ring structure having one nitrogen atom and 0-3 further heteroatoms selected from the group of N, O and S, where the rings of the structure may be spiro-linked, fused or bridged, and where the ring system may be substituted by one or more of the following substituents: F, OH, $CF_3$, CN, $OCF_3$, oxo, O—$(C_1\text{-}C_8)$-alkyl, $(C_1\text{-}C_4)$-alkoxy-$(C_1\text{-}C_4)$-alkyl, $(C_1\text{-}C_6)$-alkyl, $(C_2\text{-}C_6)$-alkenyl, $(C_2\text{-}C_6)$-alkynyl, CO(R51), (CR52R53)$_o$-R54, CO(CR52R53)$_p$-R55;
in which the meanings are
R51 H, $(C_1\text{-}C_8)$-alkyl;
R52, R53
  independently of one another H, $(C_1\text{-}C_8)$-alkyl, OH, $(C_3\text{-}C_8)$-cycloalkyl, $(C_1\text{-}C_4)$-alkoxy-$(C_1\text{-}C_4)$-alkyl;
o, p independently of one another 0, 1, 2, 3, 4, 5, 6;
R54, R55
  independently of one another OH, O—$(C_1\text{-}C_8)$-alkyl, CON(R56)(R57), N(R58)CO(R59), N(R60)(R61), $CO_2$(R62), $SO_2Me$, CN, a 3-10 membered ring system having 0 to 3 heteroatoms selected from the group of N, O and S, which may be substituted by F, Cl, Br, $CF_3$, $(C_1\text{-}C_8)$-alkyl, O—$(C_1\text{-}C_8)$-alkyl, CO(R63), oxo, OH;
R56, R57, R58, R59, R62, R63
  independently of one another H, $(C_1\text{-}C_8)$-alkyl;
or
R56 and R57
  form optionally together with the nitrogen atom to which they are bonded a 5-6 membered ring which, apart from the nitrogen atom, may also include 0-1 further heteroatoms from the group of NH, N—$(C_1\text{-}C_6)$-alkyl, oxygen and sulfur;

R60, R61
  independently of one another H, $(C_1-C_6)$-alkyl, $(C_1-C_4)$-alkoxy-$(C_1-C_4)$-alkyl, $(C_2-C_6)$-alkenyl, $(C_2-C_6)$-alkynyl, CO(R64), $(CR65R66)_q$-R67, $CO(CR68R69)_r$-R70; or R60 and R61 form together with the nitrogen atom to which they are bonded a 4 to 10-membered mono-, bi- or spirocyclic ring which, apart from the nitrogen atom, comprises 0 to 3 additional heteroatoms selected from the group of N, O and S and may additionally be substituted by one or more of the following substituents: F, Cl, Br, $CF_3$, O—$(C_1-C_8)$-alkyl, $(C_1-C_6)$-alkyl, CO(R71), oxo, OH, $(C_1-C_4)$-alkoxy-$(C_1-C_4)$-alkyl, hydroxy-$(C_1-C_4)$-alkyl, CON(R72)(R73), N(R74)CO(R75), N(R76)(R77), $CO_2$(R78), $SO_2$Me;

R64, R65, R66, R68, R69, R71, R72, R73, R74, R75, R76, R77, R78
  independently of one another H, $(C_1-C_8)$-alkyl;
or
R76 and R77
  form optionally together with the nitrogen atom to which they are bonded a 5-6 membered ring which, apart from the nitrogen atom, may also include 0-1 further heteroatoms from the group of NH, N—$(C_1-C_6)$-alkyl, oxygen and sulfur;

q, r independently of one another 0, 1, 2, 3, 4, 5, 6;

R67, R70
  independently of one another OH, O—$(C_1-C_8)$-alkyl, CON(R79)(R80), N(R81)CO(R82), N(R83)(R84), $CO_2$(R85), $SO_2$Me, CN, a 3-10 membered ring system having 0 to 3 heteroatoms selected from the group of N, O and S, which may be substituted by one or more of the following substituents: F, Cl, Br, $CF_3$, $(C_1-C_8)$-alkyl, O—$(C_1-C_8)$-alkyl, CO(R86), oxo, OH;

R79, R80, R81, R82, R83, R84, R85, R86
  independently of one another H, $(C_1-C_8)$-alkyl;
or
R79 and R80, R83 and R84
  form independently of one another optionally together with the nitrogen atom to which they are bonded a 5-6 membered ring which, apart from the nitrogen atom, may also include 0-1 further heteroatoms from the group of NH, N—$(C_1-C_6)$-alkyl, oxygen and sulfur.

The group Q in the compounds of the formula I particularly preferably has the following meanings:

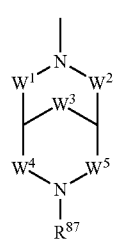

(II)

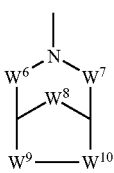

(III)

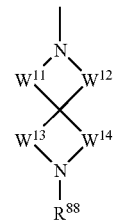

(IV)

in which the meanings are

W1, W2, W3, W4, W5, W6, W7, W8, W9, W10, W11, W12, W13, W14
  independently of one another a bond, C=C, 1 to 4-membered alkylene or alkylidene chain in which 0-1 carbon atoms outside a double bond present in the alkylidene chain may be replaced by an element from the group of N(R90), O and S, preferably a bond, a 1- to 4-membered alkylene chain in which 0-1 carbon atoms may be replaced by an element from the group of N(R90), O and S;

where the carbon atoms in the groups of the formulae (II), (III) and (IV) may be substituted by H, F, OH, oxo, $(C_1-C_6)$-alkyl, O—$(C_1-C_6)$-alkyl, $(CR52R53)_oR54$, preferably H, $(CR52R53)_oR54$;

R87, R88, R90
  H, $(C_1-C_4)$-alkoxy-$(C_1-C_4)$-alkyl, $(C_1-C_6)$-alkyl, $(C_2-C_6)$-alkenyl, $(C_2-C_6)$-alkynyl, CO(R51), $(CR52R53)_o$-R54, $CO(CR52R53)_p$-R55;

R51 H, $(C_1-C_8)$-alkyl;

R52, R53
  independently of one another H, $(C_1-C_8)$-alkyl, OH, $(C_3-C_8)$-cycloalkyl, $(C_1-C_4)$-alkoxy-$(C_1-C_4)$alkyl;

o, p independently of one another 0, 1, 2, 3, 4, 5, 6;

R54, R55
  independently of one another OH, O—$(C_1-C_8)$-alkyl, CON(R56)(R57), N(R58)CO(R59), N(R60)(R61), $CO_2$(R62), $SO_2$Me, CN, a 3-10 membered ring system having 0 to 3 heteroatoms selected from the group of N, O and S, which may be substituted by one or more of the following substituents: F, Cl, Br, $CF_3$, $(C_1-C_8)$-alkyl, O—$(C_1-C_8)$-alkyl, CO(R63), oxo, OH;

R56, R57, R58, R59, R62, R63
  independently of one another H, $(C_1-C_8)$-alkyl;
or
R56 and R57
  form optionally together with the nitrogen atom to which they are bonded a 5-6 membered ring which, apart from the nitrogen atom, may also include 0-1 further heteroatoms from the group of NH, N—$(C_1-C_6)$-alkyl, oxygen and sulfur;

R60, R61
  independently of one another H, $(C_1-C_6)$-alkyl, $(C_1-C_4)$-alkoxy-$(C_1-C_4)$-alkyl, $(C_2-C_6)$-alkenyl, $(C_2-C_6)$-alkynyl, CO(R64), $(CR65R66)_q$-R67, $CO(CR68R69)_r$-R70; or R60 and R61 form together with the nitrogen atom to which they are bonded a 4 to 10-membered mono-, bi- or spirocyclic ring which, apart from the nitrogen atom, comprises 0 to 3 additional heteroatoms selected from the group of N, O and S and may additionally be substituted by one or more of the following substituents: F, Cl, Br, $CF_3$, O—$(C_1-C_8)$-alkyl, $(C_1-C_6)$-alkyl, CO(R71), oxo, OH, $(C_1-C_4)$-alkoxy-$(C_1-C_4)$-alkyl, hydroxy-$(C_1-C_4)$-alkyl, CON(R72)(R73), N(R74)CO(R75), N(R76)(R77), $CO_2$(R78), $SO_2$Me;

R64, R65, R66, R68, R69, R71, R72, R73, R74, R75, R76, R77, R78 independently of one another H, $(C_1-C_8)$-alkyl;

or

R76 and R77 form optionally together with the nitrogen atom to which they are bonded a 5-6 membered ring which, apart from the nitrogen atom, may also include 0-1 further heteroatoms from the group of NH, N—$(C_1-C_6)$-alkyl, oxygen and sulfur;

q, r independently of one another 0, 1, 2, 3, 4, 5, 6;

R67, R70 independently of one another OH, O—$(C_1-C_8)$-alkyl, CON(R79)(R80), N(R81)CO(R82), N(R83)(R84), $CO_2$(R85), $SO_2$Me, CN, a 3-10 membered ring system having 0 to 3 heteroatoms selected from the group of N, O and S, which may be substituted by one or more of the following substituents: F, Cl, Br, $CF_3$, $(C_1-C_8)$-alkyl, O—$(C_1-C_8)$-alkyl, CO(R86), oxo, OH;

R79, R80, R81, R82, R83, R84, R85, R86 independently of one another H, $(C_1-C_8)$-alkyl;

or

R79 and R80, R83 and R84 form independently of one another optionally together with the nitrogen atom to which they are bonded a 5-6 membered ring which, apart from the nitrogen atom, may also include 0-1 further heteroatoms from the group of NH, N—$(C_1-C_6)$-alkyl, oxygen and sulfur.

In a preferred embodiment, W3 in formula II and W8 in formula III are each a bond.

It is further preferred for Q to be a radical of the formula IV in which at least one of the two rings is a 5-membered ring.

Very particularly preferred compounds of the formula I are those in which Q has the following meanings:

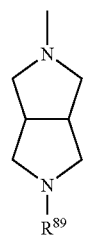
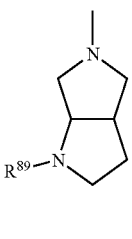
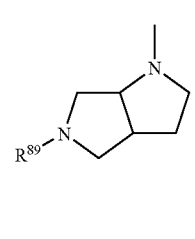
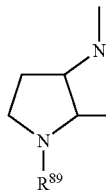
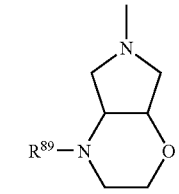
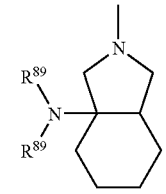
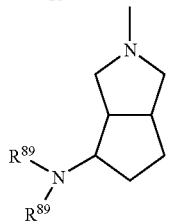
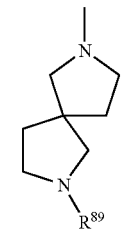
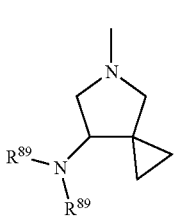
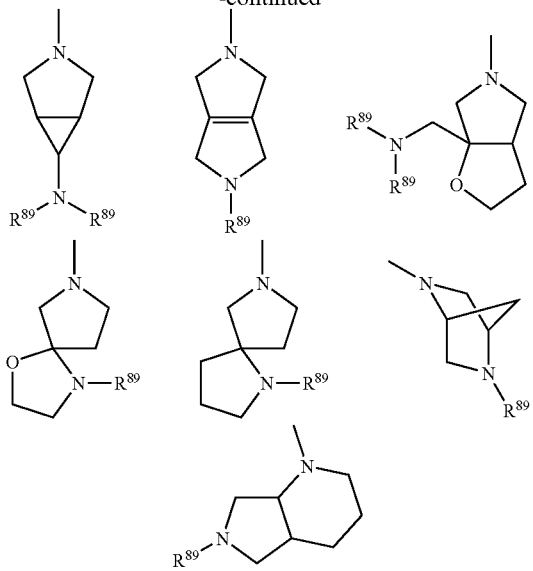

in which the meanings are:

R89 in the group N—R89:

H, $(C_1-C_4)$-alkoxy-$(C_1-C_4)$-alkyl, $(C_1-C_6)$-alkyl, $(C_2-C_6)$-alkenyl, $(C_2-C_6)$-alkynyl, CO(R51), $(CR52R53)_o$-R54, $CO(CR52R53)_p$-R55; preferably H, $(C_1-C_6)$-alkyl;

R51 H, $(C_1-C_8)$-alkyl;

R52, R53 independently of one another H, $(C_1-C_8)$-alkyl, OH, $(C_3-C_8)$-cycloalkyl, $(C_1-C_4)$-alkoxy-$(C_1-C_4)$alkyl;

o, p independently of one another 0, 1, 2, 3, 4, 5, 6;

R54, R55 independently of one another OH, O—$(C_1-C_8)$-alkyl, CON(R56)(R57), N(R58)CO(R59), N(R60)(R61), $CO_2$(R62), $SO_2$Me, CN, a 3-10 membered ring system having 0 to 3 heteroatoms selected from the group of N, O and S, which may be substituted by one or more of the following substituents: F, Cl, Br, $CF_3$, $(C_1-C_8)$-alkyl, O—$(C_1-C_8)$-alkyl, CO(R63), oxo, OH;

R56, R57, R58, R59, R62, R63 independently of one another H, $(C_1-C_8)$-alkyl;

or

R56 and R57 form optionally together with the nitrogen atom to which they are bonded a 5-6 membered ring which, apart from the nitrogen atom, may also include 0-1 further heteroatoms from the group of NH, N—$(C_1-C_6)$-alkyl, oxygen and sulfur;

R60, R61 independently of one another H, $(C_1-C_6)$-alkyl, $(C_1-C_4)$-alkoxy-$(C_1-C_4)$-alkyl, $(C_2-C_6)$-alkenyl, $(C_2-C_6)$-alkynyl, CO(R64), $(CR65R66)_q$-R67, $CO(CR68R69)_r$-R70; or R60 and R61 form together with the nitrogen atom to which they are bonded a 4 to 10-membered mono-, bi- or spirocyclic ring which, apart from the nitrogen atom, comprises 0 to 3 additional heteroatoms selected from the group of N, O and S and may additionally be substituted by one or more of the following substituents: F, Cl, Br, $CF_3$, O—$(C_1-C_8)$-alkyl, $(C_1-C_6)$-alkyl, CO(R71), oxo, OH, $(C_1-C_4)$-alkoxy-$(C_1-C_4)$-alkyl, hydroxy-$(C_1-C_4)$-alkyl, CON(R72)(R73), N(R74)CO(R75), N(R76)(R77), $CO_2$(R78), $SO_2$Me;

R64, R65, R66, R68, R69, R71, R72, R73, R74, R75, R76, R77, R78
  independently of one another H, $(C_1-C_8)$-alkyl;
or
R76 and R77
  form optionally together with the nitrogen atom to which they are bonded a 5-6 membered ring which, apart from the nitrogen atom, may also include 0-1 further heteroatoms from the group of NH, N—$(C_1-C_6)$-alkyl, oxygen and sulfur;
q, r independently of one another 0, 1, 2, 3, 4, 5, 6;
R67, R70
  independently of one another OH, O—$(C_1-C_8)$-alkyl, CON(R79)(R80), N(R81)CO(R82), N(R83)(R84), $CO_2$(R85), $SO_2$Me, CN, a 3-10 membered ring system having 0 to 3 heteroatoms selected from the group of N, O and S, which may be substituted by F, Cl, Br, $CF_3$, $(C_1-C_8)$-alkyl, O—$(C_1-C_8)$-alkyl, CO(R86), oxo, OH;
R79, R80, R81, R82, R83, R84, R85, R86
  independently of one another H, $(C_1-C_8)$-alkyl;
or
R79 and R80, R83 and R84
  form independently of one another optionally together with the nitrogen atom to which they are bonded a 5-6 membered ring which, apart from the nitrogen atom, may also include 0-1 further heteroatoms from the group of NH, N—$(C_1-C_6)$-alkyl, oxygen and sulfur;
R89 in the group $N(R89)_2$:
  independently of one another H, $(C_1-C_6)$-alkyl, $(C_1-C_4)$-alkoxy-$(C_1-C_4)$-alkyl, $(C_2-C_6)$-alkenyl, $(C_2-C_6)$-alkynyl, CO(R64), $(CR65R66)_q$-R67, CO$(CR68R69)_r$-R70; or the two R89 radicals form together with the nitrogen atom to which they are bonded a 4 to 10-membered mono-, bi- or spirocyclic ring, which, apart from the nitrogen atom, comprises 0 to 3 additional heteroatoms selected from the group of N, O and S and may additionally be substituted by one or more of the following substituents: F, Cl, Br, $CF_3$, O—$(C_1-C_8)$-alkyl, $(C_1-C_6)$-alkyl, CO(R71), oxo, OH, $(C_1-C_4)$-alkoxy-$(C_1-C_4)$-alkyl, hydroxy-$(C_1-C_4)$-alkyl, CON(R72)(R73), N(R74)CO(R75), N(R76)(R77), $CO_2$(R78), $SO_2$Me; preferably H, $(C_1-C_6)$-alkyl, or the two R89 radicals form together with the nitrogen atom to which they are bonded a 5 to 6-membered monocyclic ring which, apart from the nitrogen atom, comprises 0 to 1 additional heteroatoms selected from the group of N, O and S and may additionally be substituted by one or more of the following substituents: F, Cl, Br, $CF_3$, O—$(C_1-C_8)$-alkyl, $(C_1-C_6)$-alkyl, CO(R71), oxo, OH, $(C_1-C_4)$-alkoxy-$(C_1-C_4)$-alkyl, hydroxy-$(C_1-C_4)$-alkyl, CON(R72)(R73), N(R74)CO(R75), N(R76)(R77), $CO_2$(R78), $SO_2$Me.

It is further preferred for the group Q to have the following meanings:

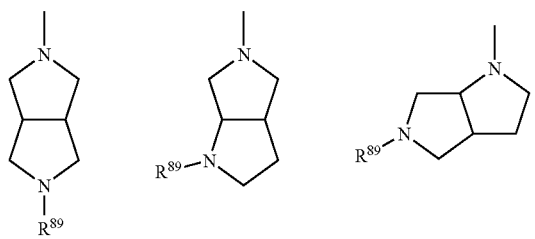

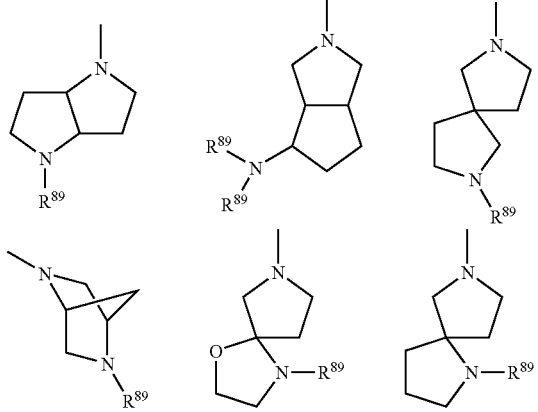

in which R89 has the abovementioned meanings.

It is particularly preferred for the group Q to have the following meanings:

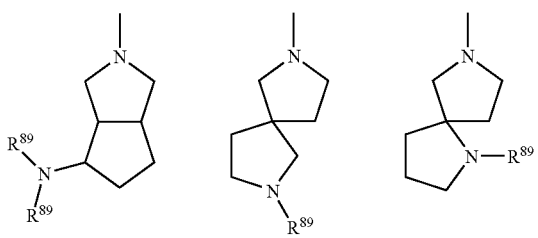

in which R89 has the abovementioned meanings.

It is very particularly preferred for Q to be

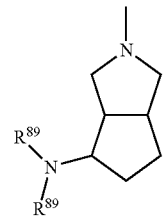

in which R89 has the abovementioned meanings.

The present invention further relates to compounds of the formula I in which
A, B, D, G
  are independently of one another N or C(R3), and the total number of nitrogen atoms in this ring is 0-2, preferably 0 or 1, particularly preferably 0;
where the other symbols in formula I have already been defined above.

In a preferred embodiment, the present application relates to compounds of the formula I
in which the meanings are
A, B, D, G
  C(R3);
R3 H, F, Cl, Br, $CF_3$, CN, O—$(C_1-C_8)$-alkyl, O—$(C_1-C_4)$-alkoxy-$(C_1-C_4)$-alkyl, S—$(C_1-C_8)$-alkyl, $(C_1-C_8)$-alkyl, $(C_0-C_8)$-alkylene-aryl, O—$(C_0-C_8)$-alkylene-aryl, N(R4)(R5), $SO_2$—$CH_3$, CON(R6)(R7), N(R8)CO(R9), CO(R12), $(CR13R14)_x$—O(R15); preferably H, F, Cl, Br, $CF_3$, CN, O—$(C_1-C_6)$-alkyl, $(C_1-C_6)$-alkyl, $SO_2$—$CH_3$, CON(R6)(R7), N(R8)CO(R9), CO(R12), (CR13R14)$_x$—O(R15), particularly preferably H, F, Cl, CF$_3$, CN, (C$_1$-C$_6$)-alkyl, (C(R13)(R14))$_x$—O(R15); very particularly preferably H, F, Cl, (C$_1$-C$_6$)-alkyl; very particularly preferably H, CH$_3$, F;

R4, R5, R6, R7, R8
  independently of one another H, (C$_1$-C$_8$)-alkyl;
or
R4 and R5, R6 and R7
  form independently of one another optionally together with the nitrogen atom to which they are bonded a 5-6 membered ring which, apart from the nitrogen atom, may also include 0-1 further heteroatoms from the group of NH, N—(C$_1$-C$_6$)-alkyl, oxygen and sulfur;
R9, R12
  independently of one another H, (C$_1$-C$_8$)-alkyl;
R13, R14
  H;
R15 H, (C$_1$-C$_6$)-alkyl;
x 0, 1, 2, preferably 0, 1, particularly preferably 1.

In a further preferred embodiment, A, B, G and D in the compounds of the formula I are CH.

R2 is preferably selected from the group consisting of: (C$_1$-C$_8$)-alkyl, (C$_1$-C$_4$)-alkoxy-(C$_1$-C$_4$)-alkyl, a 3 to 10-membered mono-, bi-, tri- or spirocyclic ring which may include 0 to 3 heteroatoms selected from the group of oxygen, nitrogen and sulfur, where the ring system may additionally be substituted by one or more of the following substituents: F, Cl, Br, CF$_3$, CN, (C$_1$-C$_6$)-alkyl, O—(C$_1$-C$_8$)-alkyl, (C$_0$-C$_2$)-alkylene-aryl, oxo, CO(R41), CON(R42)(R43), hydroxy, N(R45)CO(C$_1$-C$_6$)-alkyl, N(R46)(R47) or SO$_2$CH$_3$; preferably (C$_1$-C$_8$)-alkyl, (C$_1$-C$_4$)-alkoxy-(C$_1$-C$_4$)-alkyl, a 3 to 10-membered mono- or bicyclic ring which may include 0 to 2 heteroatoms selected from the group of oxygen, nitrogen and sulfur, where the ring system may additionally be substituted by one or more of the following substituents: F, Cl, Br, CF$_3$, CN, (C$_1$-C$_6$)-alkyl, O—(C$_1$-C$_8$)-alkyl, oxo, CO(R41), CON(R42)(R43), N(R45)CO(C$_1$-C$_6$)-alkyl or SO$_2$CH$_3$;
in which the meanings are:
R41, R42, R43, R45, R46, R47
  independently of one another H, (C$_1$-C$_8$)-alkyl;
or
R42 and R43, R46 and R47
  form independently of one another optionally together with the nitrogen atom to which they are bonded a 5-6 membered ring which, apart from the nitrogen atom, may also include 0-1 further heteroatoms from the group of NH, N—(C$_1$-C$_6$)-alkyl, oxygen and sulfur.

R2 is preferably selected from n-propyl, n-butyl, iso-butyl, iso-pentyl, cyclopropyl, cyclobutyl, cyclopentyl, cyclohexyl, cyclohex-(1)-enyl, phenyl, p-fluorophenyl, p-chlorophenyl, p-bromophenyl, p-tolyl, p-methoxyphenyl, p-trifluoromethyl phenyl, K is preferably selected from the group consisting of: bond, O, CO, OCH$_2$, CH$_2$O, N(R36)CO, N—SO$_2$, CON(R37), (C(R38)(R39))$_2$, (R31)C═C(R32), C═C, SCH$_2$, SO$_2$CH$_2$, preferably bond, O, CO, OCH$_2$, CH$_2$O, N(R36)CO, CON(R37), (C(R38)(R39))$_2$, (R31) C═C(R32), C═C, SCH$_2$, SO$_2$CH$_2$, particularly preferably OCH$_2$, CH$_2$O, N(R36)CO, CON(R37), (C(R38)(R39))$_2$, (R31)C═C(R32), C═C, SCH$_2$, SO$_2$CH$_2$, very particularly preferably OCH$_2$, CH$_2$O, CON(R37), (C(R38)(R39))$_2$, C═C, SCH$_2$; where
R31, R32, R36, R37, R38, R39
  are independently of one another H, (C$_1$-C$_8$)-alkyl.

X is preferably selected from the group consisting of bond and N(R16), in which R16 is H or (C$_1$-C$_8$)-alkyl, particularly preferably bond and NH.

The group E in the compounds of the formula I is defined above. According to the definitions above for E, E may, for example, be a five- or six-membered ring. If the group E is a five-membered ring, then the groups K and X in the compounds of the formula I are in a preferred embodiment arranged in positions 1 and 3 of the five-membered ring. If the group E is a six-membered ring, then the groups K and X are in a preferred embodiment arranged in positions 1 and 4 (that is to say in para position to one another) of the six-membered ring.

E is particularly preferably selected from the group consisting of:

This invention further relates to the use of compounds of the formula I and their pharmaceutical compositions as MCH receptor ligands. The MCH receptor ligands of the invention are particularly suitable as modulators of the activity of the MCH1R.

The role of MCH in regulating the energy balance has now been well documented (Qu, D. et al. Nature 1996, 380, 243-7; Shimada, M. et al. Nature 1998, 396, 670-4; Chen, Y et al. Endocrinology 2002, 143, 2469-77; Endocrinology 2003, 144, 4831-40; Review: G. Hervieu, Expert Opin. Ther. Targets 2003, 7, 495-511).

There are also indications that MCH antagonists can have a beneficial influence on centrally related disorders such as, for example, depressions (Borowsky, B. et al. Nature Medicine 2002, 8, 825-30; Review: G. Hervieu, Expert Opin. Ther. Targets 2003, 7, 495-511).

Compounds of this type are particularly suitable for the treatment and/or prevention of
1. Obesity
2. Diabetes mellitus, especially type 2 diabetes, including the prevention of the sequelae associated therewith.
    Particular aspects in this connection are
    hyperglycemia,
    improvement in insulin resistance,
    improvement in glucose tolerance,
    protection of the pancreatic R cells
    prevention of macro- and microvascular disorders
3. Dyslipidemias and the sequelae thereof such as, for example, atherosclerosis, coronary heart disease, cerebrovascular disorders etc, especially those (but not restricted thereto) which are characterized by one or more of the following factors:
    high plasma triglyceride concentrations, high postprandial plasma triglyceride concentrations
    low HDL cholesterol concentration
4. Various other conditions which may be associated with the metabolic syndrome, such as:
    thromboses, hypercoagulable and prothrombotic stages (arterial and venous)
    high blood pressure
    heart failure such as, for example (but not restricted thereto), following myocardial infarction, hypertensive heart disease or cardiomyopathy
5. Psychiatric indications such as
    depressions
    anxiety states
    disturbances of the circadian rhythm
    affection disorders
    schizophrenia
    addictive disorders Formulations The amount of a compound of formula I necessary to achieve the desired biological effect depends on a number of factors, for example the specific compound chosen, the intended use, the mode of administration and the clinical condition of the patient. The daily dose is generally in the range from 0.001 mg to 100 mg (typically from 0.01 mg to 50 mg) per day and per kilogram of bodyweight, for example 0.1-10 mg/kg/day. An intravenous dose may be, for example, in the range from 0.001 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampoules for injections may contain, for example, from 1 mg to 100 mg, and single-dose formulations which can be administered orally, such as, for example, tablets or capsules, may contain, for example, from 0.05 to 1000 mg, typically from 0.5 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical preparations for oral administration may be in the form of separate units such as, for example, capsules, cachets, suckable tablets or tablets, each of which contain a defined amount of the compound of formula I; as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one or more surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single plasters which are suitable for long-term close contact with the patient's epidermis. Such plasters suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

The compounds of the formula I are distinguished by beneficial effects on lipid metabolism, and they are particularly suitable for weight reduction and for maintaining a reduced weight after weight reduction has taken place in mammals and as anorectic agents. The compounds are distinguished by their low toxicity and their few side effects. The compounds can be employed alone or in combination with other weight-reducing or anorectic active ingredients. Further anorectic active ingredients of this type are mentioned, for example, in the Rote Liste, chapter 01 under weight-reducing agents/appetite suppressants, and may also include active ingredients which increase the energy turnover of the organism and thus lead to weight reduction or else those which influence the general metabolism of the organism in such a way that an increased calorie intake does not lead to an enlargement of the fat depots and a normal calorie intake leads to a reduction of the fat depots of the organism. The compounds are suitable for the prophylaxis and, in particular, for the treatment of excessive weight or obesity. The compounds are further suitable for the prophylaxis and, in particular, for the treatment of type II diabetes, of arteriosclerosis and for normalizing lipid metabolism and for the treatment of high blood pressure.

Combinations with Other Medicaments

The compounds of the invention can be administered alone or in combination with one or more further pharmacologically active substances which have, for example, beneficial effects on metabolic disturbances or disorders frequently associated therewith. Examples of such medicaments are 1. medicaments which lower blood glucose, antidiabetics,
2. active ingredients for the treatment of dyslipidemias,
3. antiatherosclerotic medicaments,
4. antiobesity agents,
5. antiinflammatory active ingredients
6. active ingredients for the treatment of malignant tumors
7. antithrombotic active ingredients
8. active ingredients for the treatment of high blood pressure
9. active ingredients for the treatment of heart failure and
10. active ingredients for the treatment and/or prevention of complications caused by diabetes or associated with diabetes.

They can be combined with the compounds of the invention of the formula I in particular for a synergistic improvement in the effect. Administration of the active ingredient combination can take place either by separate administration of the active ingredients to the patient or in the form of combination products in which a plurality of active ingredients are present in one pharmaceutical preparation.

Examples which may be mentioned are:
Antidiabetics

Suitable antidiabetics are disclosed for example in the Rote Liste 2001, chapter 12 or the USP Dictionary of USAN and International Drug Names, US Pharmacopeia, Rockville 2003. Antidiabetics include all insulins and insulin derivatives, such as, for example, Lantus® (see www.lantus.com) or Apidra®, and other fast-acting insulins (see, U.S. Pat. No. 6,221,633), GLP-1 receptor modulators, as described in WO 01/04146 or else such as those disclosed in WO 98/08871 of Novo Nordisk A/S for example.

The orally effective hypoglycemic active ingredients include, preferably, sulfonylureas, biguanides, meglitinides, oxadiazolidinediones, thiazolidinediones, glucosidase inhibitors, glucagon antagonists, oral GLP-1 agonists, DPP-IV inhibitors, potassium channel openers such as, for example, those disclosed in WO 97/26265 and WO 99/03861, insulin sensitizers, inhibitors of liver enzymes involved in the stimulation of gluconeogenesis and/or glycogenolysis, modulators of glucose uptake, compounds which alter lipid metabolism and lead to a change in the blood lipid composition, compounds which reduce food intake or food absorption, PPAR and PXR modulators and active ingredients which act on the ATP-dependent potassium channel of the beta cells.

In one embodiment of the invention, the compounds of the formula I are administered in combination with insulin.

In one embodiment of the invention, the compounds of the formula I are administered in combination with substances which influence hepatic glucose production such as, for example, glycogen phosphorylase inhibitors (see: WO 01/94300, WO 02/096864, WO 03/084923, WO 03/084922, WO 03/104188).

In one embodiment, the compounds of the formula I are administered in combination with a sulfonylurea such as, for example, tolbutamide, glibenclamide, glipizide or glimepiride.

In one embodiment, the compounds of the formula I are administered in combination with an active ingredient which acts on the ATP-dependent potassium channel of the beta cells, such as, for example, tolbutamide, glibenclamide, glipizide, glimepiride or repaglinide.

In one embodiment, the compounds of the formula I are administered in combination with a biguanide such as, for example, metformin.

In a further embodiment, the compounds of the formula I are administered in combination with a meglitinide such as, for example, repaglinide.

In one embodiment, the compounds of the formula I are administered in combination with a thiazolidinedione such as, for example, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl]methyl]-2,4-thiazolidinedione.

In one embodiment, the compounds of the formula I are in combination with a DPPIV inhibitor as described, for example, in WO98/19998, WO99/61431, WO99/67278, WO99/67279, WO01/72290, WO 02/38541, WO03/040174, in particular P 93/01 (1-cyclopentyl-3-methyl-1-oxo-2-pentanammonium chloride), P-31/98, LAF237 (1-[2-[3-hydroxyadamant-1-ylamino)acetyl]pyrrolidine-2-(S)-carbonitrile), TS021 ((2S,4S)-4-fluoro-1-[[(2-hydroxy-1,1-dimethylethyl)amino]-acetyl]pyrrolidine-2-carbonitrile monobenzenesulfonate).

In one embodiment of the invention, the compounds of the formula I are administered in combination with a PPAR-gamma agonist such as, for example, rosiglitazone, pioglitazone.

In one embodiment, the compounds of the formula I are administered in combination with compounds with an inhibitory effect on SGLT-1 and/or 2, as disclosed directly or indirectly for example in PCT/EP03/06841, PCT/EP03/13454 and PCT/EP03/13455.

In one embodiment, the compounds of the formula I are administered in combination with an α-glucosidase inhibitor such as, for example, miglitol or acarbose.

In one embodiment, the compounds of the formula I are administered in combination with more than one of the aforementioned compounds, e.g. in combination with a sulfonylurea and metformin, a sulfonylurea and acarbose, repaglinide and metformin, insulin and a sulfonylurea, insulin and metformin, insulin and troglitazone, insulin and lovastatin, etc.

Lipid Modulators

In one embodiment of the invention, the compounds of the formula I are administered in combination with an HMG-CoA-reductase inhibitor, such as lovastatin, fluvastatin, pravastatin, simvastatin, ivastatin, itavastatin, atorvastatin, rosuvastatin.

In one embodiment of the invention, the compounds of the formula I are administered in combination with a bile acid absorption inhibitor (see, for example, U.S. Pat. No. 6,245,744, U.S. Pat. No. 6,221,897, U.S. Pat. No. 6,277,831, EP 0683 773, EP 0683 774).

In one embodiment of the invention, the compounds of the formula I are administered in combination with a polymeric bile acid adsorbent such as, for example, cholestyramine or colesevelam.

In one embodiment of the invention, the compounds of the formula I are administered in combination with a cholesterol absorption inhibitor as described for example in WO 0250027, or ezetimibe, tiqueside, pamaqueside.

In one embodiment of the invention, the compounds of the formula I are administered in combination with an LDL receptor inducer (see, for example, U.S. Pat. No. 6,342,512).

In one embodiment, the compounds of the formula I are administered in combination with bulking agents, preferably insoluble bulking agents (see, for example, carob/Caromax® (Zunft H J; et al., Carob pulp preparation for treatment of hypercholesterolemia, ADVANCES IN THERAPY (2001 September-October), 18(5), 230-6). Caromax is a carob-containing product from Nutrinova, Nutrition Specialties & Food Ingredients GmbH, Industriepark Hoechst, 65926 Frankfurt/Main). Combination with Caromax® is possible in one preparation or by separate administration of compounds of the formula I and Caromax®. Caromax® can in this connection also be administered in the form of food products such as, for example, in bakery products or muesli bars.

In one embodiment of the invention, the compounds of the formula I are administered in combination with a PPARalpha agonist.

In one embodiment of the invention, the compounds of the formula I are administered in combination with a fibrate such as, for example, fenofibrate, gemfibrozil, clofibrate, bezafibrate.

In one embodiment of the invention, the compounds of the formula I are administered in combination with nicotinic acid or niacin.

In one embodiment of the invention, the compounds of the formula I are administered in combination with a CETP inhibitor, e.g. CP-529, 414 (torcetrapib).

In one embodiment of the invention, the compounds of the formula I are administered in combination with an ACAT inhibitor.

In one embodiment of the invention, the compounds of the formula I are administered in combination with an MTP inhibitor such as, for example, implitapide.

In one embodiment of the invention, the compounds of the formula I are administered in combination with an antioxidant.

In one embodiment of the invention, the compounds of the formula I are administered in combination with a lipoprotein lipase inhibitor.

In one embodiment of the invention, the compounds of the formula I are administered in combination with an ATP-citrate lyase inhibitor.

In one embodiment of the invention, the compounds of the formula I are administered in combination with a squalene synthetase inhibitor.

In one embodiment of the invention, the compounds of the formula I are administered in combination with a lipoprotein (a) antagonist.

Antiobesity Agents

In one embodiment of the invention, the compounds of the formula I are administered in combination with a lipase inhibitor such as, for example, orlistat.

In one embodiment, the further active ingredient is fenfluramine or dexfenfluramine.

In another embodiment, the further active ingredient is sibutramine.

In another embodiment, the further active ingredient is rimonabant.

In a further embodiment, the compounds of the formula I are administered in combination with CART modulators (see "Cocaine-amphetamine-regulated transcript influences energy metabolism, anxiety and gastric emptying in mice" Asakawa, A, et al., M.: Hormone and Metabolic Research (2001), 33(9), 554-558), NPY antagonists, e.g. naphthalene-1-sulfonic acid {4-[(4-aminoquinazolin-2-ylamino)methyl]-cyclohexylmethyl}amide; hydrochloride (CGP 71683A), MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]amide; (WO 01/91752)), orexin antagonists (e.g. 1-(2-methylbenzoxazol-6-yl)-3-[1,5]naphthyridin-4-ylurea; hydrochlorides (SB-334867-A)), CB1 antagonists/inverse agonists, H3 antagonists/inverse agonists (e.g. 3-cyclohexyl-1-(4,4-dimethyl-1,4,6,7-tetrahydroimidazo[4,5-c]pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl]dipropylamine (WO 00/66585)), CRF BP antagonists (e.g. urocortin), urocortin agonists, (33 agonists (e.g. 1-(4-chloro-3-methanesulfonylmethylphenyl)-2-[2-(2,3-dimethyl-1H-indol-6-yloxy)ethylamino]ethanol; hydrochloride (WO 01/83451)), MSH (melanocyte-stimulating hormone) agonists, CCK-A agonists (e.g. {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525)); serotonin reuptake inhibitors (e.g. dexfenfluramine), mixed serotoninergic and noradrenergic compounds (e.g. WO 00/71549), 5HT agonists e.g. 1-(3-ethylbenzofuran-7-yl)piperazine oxalic acid salt (WO 01/09111), BRS3 agonists, galanin antagonists, ghrelin antagonists, MCH antagonists, mGluR5 antagonists, opioid antagonists, growth hormone (e.g. human growth hormone), growth hormone-releasing compounds (6-benzyloxy-1-(2-diisopropylaminoethylcarbamoyl)-3,4-dihydro-1H-isoquinoline-2-carboxylic acid tertiary butyl ester (WO 01/85695)), CNTF, CNTF derivatives (e.g. Axokine), TRH agonists (see, for example, EP 0 462 884), uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881), DA agonists (bromocriptine, Doprexin), lipase/amylase inhibitors (e.g. WO 00/40569), PPAR modulators (e.g. WO 00/78312), RXR modulators or TR-β agonists.

In one embodiment of the invention, the further active ingredient is leptin.

In one embodiment, the further active ingredient is dexamphetamine, amphetamine, mazindole or phentermine.

In one embodiment, the compounds of the formula I are administered in combination with medicaments having effects on the coronary circulation and the vascular system, such as, for example, ACE inhibitors (e.g. ramipril), medicaments which act on the angiotensin-renine system, calcium antagonists, beta blockers etc.

In one embodiment, the compounds of the formula I are administered in combination with medicaments having an antiinflammatory effect.

In one embodiment, the compounds of the formula I are administered in combination with medicaments which are employed for cancer therapy and cancer prevention.

It will be appreciated that every suitable combination of the compounds of the invention with one or more of the aforementioned compounds and optionally one or more other pharmacologically active substances is regarded as falling within the protection conferred by the present invention.

The activity of the compounds was tested as follows:
Cloning of the cDNA for the human MCH receptor, preparation of a recombinant HEK293 cell line which expresses the human MCH receptor, and functional measurements with the recombinant cell line took place in analogy to the description by Audinot et al. (J. Biol. Chem. 276, 13554-13562, 2001). A difference from the reference was, however, the use of the plasmid pEAK8 from EDGE Biosystems (USA) for the construction of the expression vector. The host used for the transfection was a transformed HEK cell line named "PEAK Stable Cells" (likewise from EDGE Biosystems). Functional measurements of the cellular calcium flux after addition of agonist (MCH) in the presence of ligand of the invention took place with the aid of the FLIPR apparatus from Molecular Devices (USA), using protocols of the apparatus manufacturer.

Biological Test Model

The anorectic effect was tested on female NMRI mice. After withdrawal of feed for 17 hours, the test product was administered by gavage. The animals were housed singly with free access to drinking water and were offered condensed milk 30 minutes after administration of the product. The condensed milk consumption was determined every half hour for 7 hours, and the general wellbeing of the animals was observed. The measured milk consumption was compared with the vehicle-treated control animals.

TABLE 1

Anorectic effect relating to compounds of the formula I which have no linker L, measured as the reduction in the cumulative milk consumption of treated compared with control animals.

(I)

$$R2{-}K{-}E{-}X{-}\overset{O}{C}{-}N(R1){-}\underset{G-D}{\overset{A=B}{C}}{-}Q$$

| Example | Oral dose [mg/kg] | Reduction in cumulative milk consumption as % of the control |
|---|---|---|
| 9 | 30 | 82 |

The examples and preparation methods detailed below serve to illustrate the invention without, however, restricting it.

Preparation Methods

The compounds of the invention of the formula I can be prepared with the aid of reactions known in principle. For example, the compounds were obtained according to the following general reaction schemes.

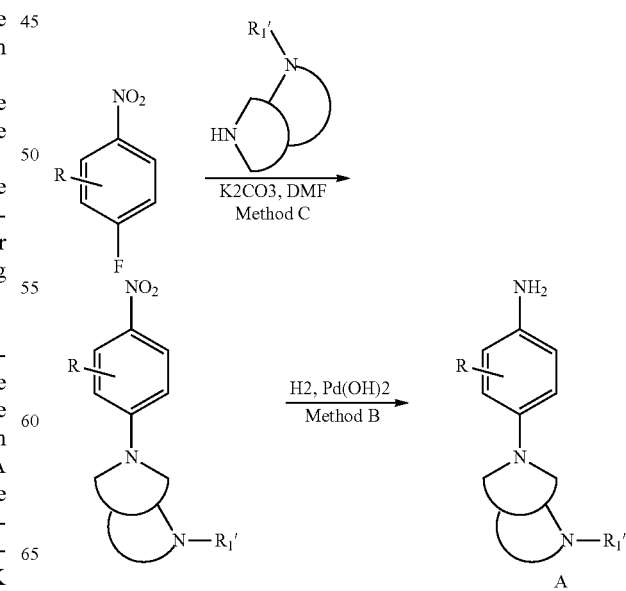

A

-continued

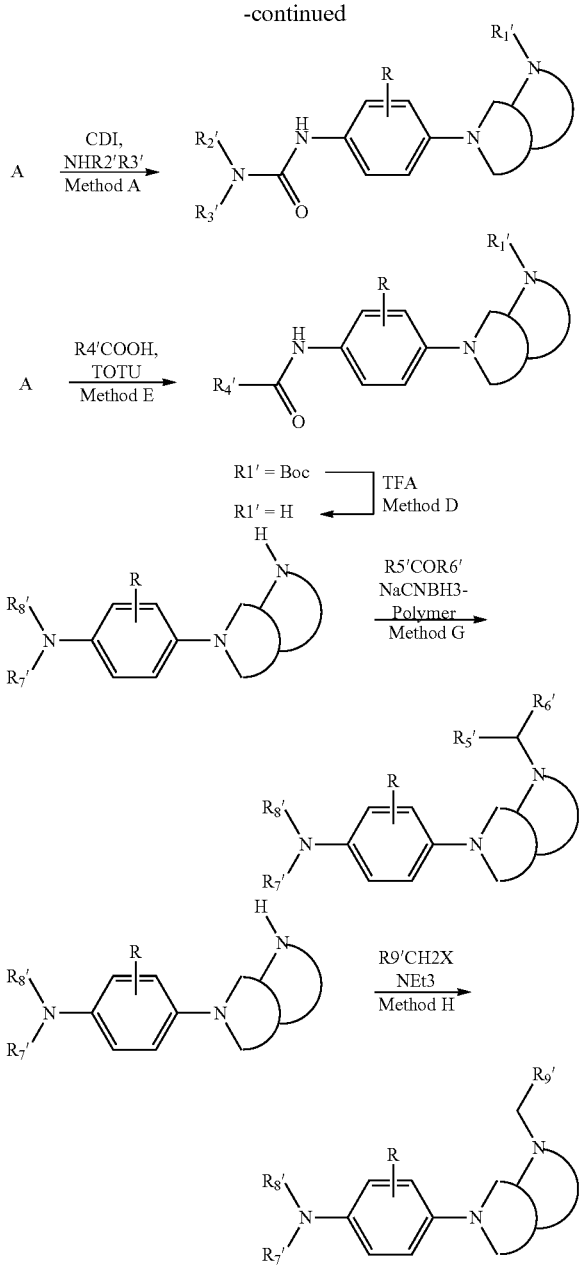

Descriptions of the general methods used are to be found by way of example at the following places:
Methods A, B and C in Example 1;
Method D in Example 2;
Method E in Example 4;
Method F in Example 5;
Method G in Example 98;
Method H in Example 185.

EXAMPLES

General Explanations a) Mode of Drawing the Structural Formulae

Only non-hydrogen atoms are depicted for clarity in the structural formulae of the examples given.

b) Salt Forms

Many of the compounds of the invention are bases and can form salts with appropriately strong acids. In particular, after purification of the compounds by HPLC chromatography using a trifluoroacetic acid-containing mobile phase they may be in the form of hydrotrifluoroacetates. These can be converted into the free bases shown by simple treatment of a solution of the salts for example with sodium carbonate solution.

c) Units of the Characterizing Data

The unit of the stated molecular weights is "g/mol". Peaks observed in the mass spectrum are indicated as integral quotient of the molar molecular ion mass and of the charge on the molecular ion (m/z).

Example 1

5-{4-[3-(4-Phenoxyphenyl)ureido]phenyl}-2,5-diazabicyclo[2.2.1]heptane-2-carboxylic acid tert-butyl ester

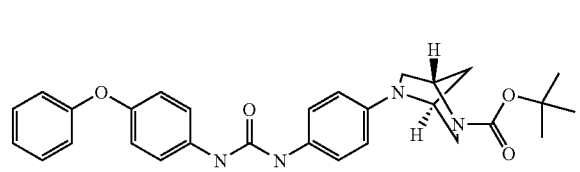 [SMILES: CC(C)(C)OC(=O)N1C[C@@H]2C[C@H]1CN2c1ccc(NC(=O)Nc2ccc(Oc3ccccc3)cc2)cc1]

Method A

A solution of 4-phenoxyaniline (185 mg) in DMF (1 ml) was added dropwise to a solution, cooled to 0° C., of carbonyldiimidazole (162 mg) in DMF (1 ml). After 30 minutes, 5-(4-aminophenyl)-2,5-diazabicyclo[2.2.1]heptane-2-carboxylic acid tert-butyl ester (289 mg) in DMF (1 ml) was added dropwise. The reaction solution was kept firstly at room temperature for 2 hours and then at 80° C. for 30 minutes. The mixture was added dropwise to water (20 ml), and the resulting precipitate was filtered off with suction and washed with water. Alternatively, the product can also be extracted with ethyl acetate and purified after concentration by chromatography. The product with the molecular weight of 500.60 (C29H32N4O4); MS (ESI): 501 (M+H+) was obtained in this way.

5-(4-Aminophenyl)-2,5-diazabicyclo[2.2.1]heptane-2-carboxylic acid tert-butyl ester Method B A suspension of 5-(4-nitrophenyl)-2,5-diazabicyclo[2.2.1]heptane-2-carboxylic acid tert-butyl ester (450 mg) and palladium(II) hydroxide (20% on carbon; 0.15 g) in ethanol (30 ml) was vigorously stirred under a hydrogen atmosphere (atmospheric pressure) for 3 hours. The catalyst was then removed by filtration, and the filtrate was concentrated. The product with the molecular weight of 289.38 (C16H23N3O2); MS (ESI): 290 (M+H+) was obtained in this way.

5-(4-Nitrophenyl)-2,5-diazabicyclo[2.2.1]heptane-2-carboxylic acid tert-butyl ester Method C A suspension of 2,5-diazabicyclo[2.2.1]heptane-2-carboxylic acid tert-butyl ester (400 mg) and potassium carbonate (300 mg) in DMF (5 ml) was mixed with 4-fluoronitrobenzene (290 mg). After 2 hours, the reaction mixture was poured into water, and the resulting precipitate was filtered off with suction. Alternatively, the product can also be extracted with ethyl acetate and purified after concentration by chromatography. The product with the molecular weight of 319.36 (C16H21N3O4); MS (ESI): 320 (M+H+) was obtained in this way.

Example 2

1-[4-(2,5-Diazabicyclo[2.2.1]hept-2-yl)phenyl]-3-(4-phenoxyphenyl)urea

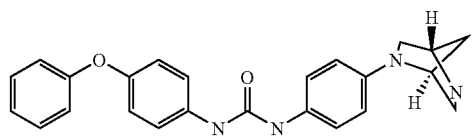 [SMILES: O=C(Nc1ccc(Oc2ccccc2)cc1)Nc1ccc(N2C[C@@H]3C[C@H]2CN3)cc1]

Method D

A solution of 5-{4-[3-(4-phenoxyphenyl)ureido]phenyl}-2,5-diaza-bicyclo[2.2.1]heptane-2-carboxylic acid tert-butyl ester (80 mg) in dichloromethane (1 ml) was mixed with trifluoroacetic acid (1 ml). After two hours at room temperature, the reaction mixture was made alkaline with saturated potassium carbonate solution, and the aqueous phase was extracted twice with dichloromethane. The combined organic phases were dried over magnesium sulfate and concentrated. The residue was purified by preparative HPLC. The product with the molecular weight of 400.48 (C24H24N4O2); MS (ESI): 401 (M+H+) was obtained in this way.

Example 3

4-(4-Chlorophenyl)piperidine-1-carboxylic acid [4-(1-methylhexahydro-pyrrolo[3,4-b]pyrrol-5-yl)phenyl]amide

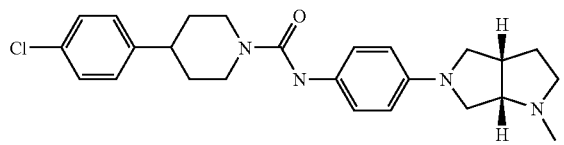 [SMILES: CN1CC[C@H]2CN(c3ccc(NC(=O)N4CCC(c5ccc(Cl)cc5)CC4)cc3)C[C@H]21]

4-(1-Methylhexahydropyrrolo[3,4-b]pyrrol-5-yl)phenylamine was reacted by method A initially with carbonyldiimidazole and then with 4-(4-chlorophenyl)piperidine. The product with the molecular weight of 439.01 (C25H31ClN4O); MS (ESI): 439 (M+H+) was obtained in this way.

4-(1-Methylhexahydropyrrolo[3,4-b]pyrrol-5-yl)-phenylamine

1-Methyloctahydropyrrolo[3,4-b]pyrrole (EP 0 393 424) was reacted by method C and B. The product with the molecular weight of 217.32 (C13H19N3); MS (ESI): 218 (M+H+) was obtained in this way.

Example 4

4-Isobutoxy-N-[4-(1-methylhexahydropyrrolo[3,4-b]pyrrol-5-yl)phenyl]benzamide

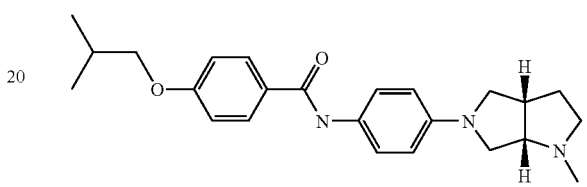

Method E

TOTU (78 mg) and ethyldiisopropylamine (31 mg) were added, followed by 4-(1-methylhexahydropyrrolo[3,4-b]pyrrol-5-yl)phenylamine to a solution of 4-isobutoxybenzoic acid (46.4 mg) in DMF (2 ml) at 0° C. After a reaction time of three hours at room temperature, the mixture was diluted with sodium bicarbonate solution and ethyl acetate. After separation of the phases, the aqueous phase was extracted with ethyl acetate, and the combined organic phases were dried over magnesium sulfate and concentrated. The residue was purified by preparative HPLC. The product with the molecular weight of 393.53 (C24H31N3O2); MS (ESI): 394 (M+H+) was obtained in this way.

Example 5

4-(4-Chlorophenyl)piperidine-1-carboxylic acid [4-(5-methylhexahydropyrrolo[3,4-c]pyrrol-2-yl)phenyl]amide

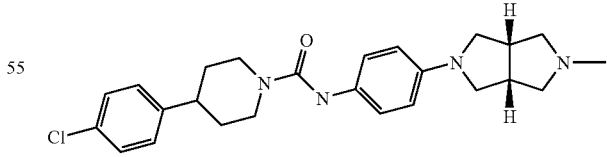

2-Methyloctahydropyrrolo[3,4-c]pyrrole was reacted as described in Example 3 initially to give 4-(5-methyl hexahydropyrrolo[3,4-c]pyrrol-2-yl)-phenylamine and then reacted with carbonyldiimidazole and finally with 4-(4-chlorophenyl)piperidine. The product with the molecular weight of 439.01 (C25H31ClN4O); MS (ESI): 439 (M+H+) was obtained in this way.

2-Methyloctahydropyrrolo[3,4-c]pyrrole

Method F

A solution of 2-benzyl-5-methyloctahydropyrrolo[3,4-c]pyrrole (2.4 g) in methanol (60 ml) was mixed with ammonium formate (2.1 g) and palladium on carbon (5%, 0.12 g), and the mixture was refluxed for 8 hours. After cooling, the reaction solution was filtered and concentrated. The crude product could be directly reacted further. The product with the molecular weight of 126.20 (C7H14N2); MS (ESI): 127 (M+H+) was obtained in this way.

2-Benzyl-5-methyloctahydropyrrolo[3,4-c]pyrrole

A solution of 5-benzyl-2-methyltetrahydropyrrolo[3,4-c]pyrrole-1,3-dione (3.6 g) in THF (15 ml) was added dropwise to a suspension of lithium aluminum hydride (1.68 g) in THF (20 ml) while cooling in ice. The mixture was heated to reflux for 4 hours and then, at 0° C., water (1.8 ml), sodium hydroxide solution (10 M; 1.8 ml) and water (2.5 ml) were cautiously added. The precipitate was filtered off with suction and washed with ethyl acetate. The filtrate was concentrated. The product with the molecular weight of 216.33 (C14H20N2); MS (ESI): 217 (M+H+) was obtained in this way.

5-Benzyl-2-methyltetrahydropyrrolo[3,4-c]pyrrole-1,3-dione

Trifluoroacetic acid (2.4 g) was added dropwise to a solution of benzyl-methoxymethyltrimethylsilanylmethylamine (5.1 g) and 1-methylpyrrole-2,5-dione (2.98 g) in dichloromethane (50 ml) at 0° C. Stirring at 0° C. for 15 minutes was followed by further stirring at room temperature for one hour. The reaction mixture was diluted with dichloromethane, washed with sodium bicarbonate solution and water, dried over magnesium sulfate and concentrated. The product with the molecular weight of 244.30 (C14H16N2O2); MS (ESI): 245 (M+H+) was obtained in this way.

Example 6

4-Butoxy-N-[4-(5-methyl hexahydropyrrolo[3,4-c]pyrrol-2-yl)phenyl]-benzamide

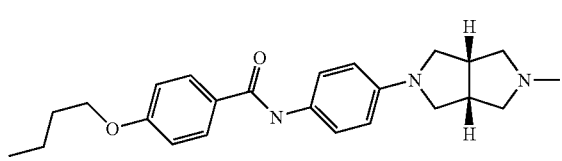 [SMILES: CCCCOc1ccc(C(=O)Nc2ccc(N3C[C@H]4CN(C)C[C@H]4C3)cc2)cc1]

4-Butoxybenzoic acid was reacted with 4-(5-methylhexahydropyrrolo[3,4-c]pyrrol-2-yl)phenylamine by method E. The product with the molecular weight of 393.53 (C24H31N3O2); MS (ESI): 394 (M+H+) was obtained in this way.

Example 7

4-(4-Chlorophenyl)piperidine-1-carboxylic acid [4-(4-methylhexahydropyrrolo[3,2-b]pyrrol-1-yl)phenyl]amide

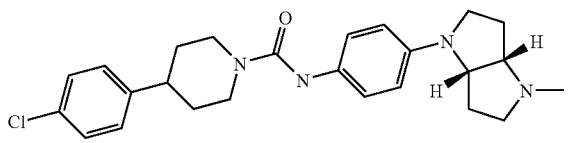 [SMILES: CN1CC[C@H]2[C@@H]1CCN2c1ccc(NC(=O)N2CCC(c3ccc(Cl)cc3)CC2)cc1]

4-(4-Methylhexahydropyrrolo[3,2-b]pyrrol-1-yl)phenylamine was reacted by method A with carbonyldiimidazole and finally with 4-(4-chlorophenyl)-piperidine. The product with the molecular weight of 439.01 (C25H31ClN4O); MS (ESI): 439 (M+H+) was obtained in this way.

4-(4-Methylhexahydropyrrolo[3,2-b]pyrrol-1-yl)phenylamine

1-Methyl-4-(4-nitrophenyl)octahydropyrrolo[3,2-b]pyrrole was hydrogenated by method B using methanol as solvent and palladium on carbon (5%) as catalyst. The product with the molecular weight of 217.32 (C13H19N3); MS (ESI): 218 (M+H+) was obtained in this way.

1-Methyl-4-(4-nitrophenyl)octahydropyrrolo[3,2-b]pyrrole

A mixture of 1-(4-nitrophenyl)octahydropyrrolo[3,2-b]pyrrole (0.7 g), formaldehyde (37%; 0.27 ml), formic acid (0.28 ml) and dioxane (1 ml) was heated to reflux for two hours. The cooled reaction mixture was mixed with hydrochloric acid (2M; 1.7 ml) and concentrated. The residue was taken up in water, and potassium hydroxide was added until the reaction was strongly alkaline. The resulting precipitate was filtered off with suction. The product with the molecular weight of 247.30 (C13H17N3O2); MS (ESI): 248 (M+H+) was obtained in this way.

1-(4-Nitrophenyl)octahydropyrrolo[3,2-b]pyrrole

Octahydropyrrolo[3,2-b]pyrrole (0.50 g) was reacted by method C with 4-fluoronitrobenzene (0.53 g). The product with the molecular weight of 233.27 (C12H15N3O2); MS (ESI): 234 (M+H+) was obtained in this way.

Octahydropyrrolo[3,2-b]pyrrole 1,4-Dibenzyloctahydropyrrolo[3,2-b]pyrrole was debenzylated by method F using palladium(II) hydroxide (20% on carbon). The product with the molecular weight of 112.18 (C6H12N2); MS (ESI): 113 (M+H+) was obtained in this way.

1,4-Dibenzyloctahydropyrrolo[3,2-b]pyrrole

A mixture of 1,3,4,6-tetramethanesulfonyloxyhexane (20.6 g), benzylamine (39.6 ml) and dioxane (550 ml) was refluxed for three hours. Triethylamine (60.5 ml) and acetyl chloride (25.9 ml) were added to the cooled reaction solution. After 40 minutes, the reaction mixture was concentrated and the residue was partitioned between hydrochloric acid (6 N) and ethyl acetate. The aqueous phase was basified with sodium hydroxide solution (10 N) and extracted 4 times with ethyl acetate. The combined organic phases were dried over magnesium sulfate and concentrated. The product with the molecular weight of 292.43 (C20H24N2); MS (ESI): 293 (M+H+) was obtained in this way.

1,3,4,6-Tetramethanesulfonyloxyhexane

Methanesulfonyl chloride (30.4 ml) was added to a solution of hexane-1,3,4,6-tetraole (8.3 g) in pyridine (150 ml) at −45° C. After reaction at ice-bath temperature for a time of three hours, the mixture was poured into hydrochloric acid (4 N). The resulting precipitate was filtered off with suction. The product with the molecular weight of 462.54 (C10H22O12S4); MS (ESI): 463 (M+H+) was obtained in this way.

Hexane-1,3,4,6-tetraole

4-Methylmorpholine 4-oxide (50% in water) was slowly added to a mixture of hex-3-ene-1,6-diol (7.2 g), acetone (77 ml), water (150 ml), tert-butanol (77 ml), methanesulfonamide (5.9 g) and potassium osmate (228 mg). After 12 hours, the mixture was concentrated and purified by column chromatography on silica gel (mobile phase: ethyl acetate/methanol 3:1). The product with the molecular weight of 150.18 (C6H14O4); MS (ESI): 151 (M+H+) was obtained in this way.

Example 8

4-Butoxy-N-[4-(4-methylhexahydropyrrolo[3,2-b]pyrrol-1-yl)phenyl]benzamide

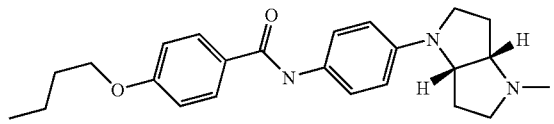 [SMILES: CCCCOc1ccc(C(=O)Nc2ccc(N3CC[C@H]4[C@@H]3CCN4C)cc2)cc1]

4-Butoxybenzoic acid was reacted with 4-(4-methylhexahydropyrrolo[3,2-b]pyrrol-1-yl)phenylamine by method E. The product with the molecular weight of 393.53 (C24H31N3O2); MS (ESI): 394 (M+H+) was obtained in this way.

Example 9

4-(4-Chlorophenyl)piperidine-1-carboxylic acid [4-(5-methylhexahydropyrrolo[3,4-b]pyrrol-1-yl)phenyl]amide

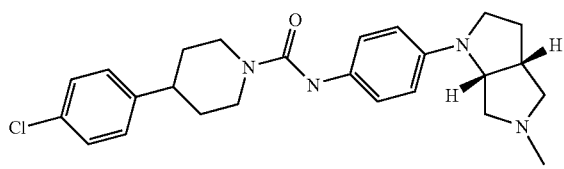 [SMILES: CN1C[C@H]2CCN(c3ccc(NC(=O)N4CCC(c5ccc(Cl)cc5)CC4)cc3)[C@H]2C1]

5-Methyloctahydropyrrolo[3,4-b]pyrrole (EP 0 393 424) was initially converted as described in Example 3 into 4-(5-methylhexahydropyrrolo[3,4-b]pyrrol-1-yl)-phenylamine and then reacted with carbonyldiimidazole and subsequently with 4-(4-chlorophenyl)piperidine. The product with the molecular weight of 439.01 (C25H31ClN4O); MS (ESI): 439 (M+H+) was obtained in this way.

Example 10

N-[4-(4-Acetyl-1-oxa-4,7-diazaspiro[4.4]non-7-yl)phenyl]-4-butoxybenzamide

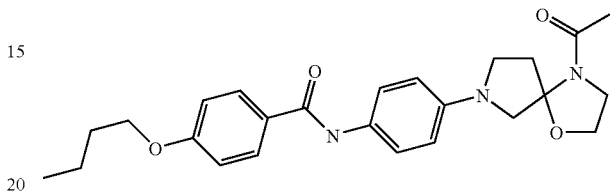

A mixture of 4-butoxy-N-[4-(3-oxopyrrolidin-1-yl)phenyl]benzamide (70 mg), ethanolamine (12 mg), potassium carbonate (27 mg) and dichloromethane (3 ml) was stirred for 48 hours, and then acetyl chloride (16 mg) was added. After 20 hours, the mixture was diluted with dichloromethane, washed with water, dried over magnesium sulfate and concentrated. The residue was purified by preparative HPLC. The product with the molecular weight of 437.54 (C25H31N3O4); MS (ESI): 438 (M+H+) was obtained in this way.

4-Butoxy-N-[4-(3-oxopyrrolidin-1-yl)phenyl]benzamide

4-Butoxybenzoic acid was reacted with 4-(1,4-dioxa-7-azaspiro[4.4]non-7-yl)phenylamine by method E. The resulting amide (0.25 g) in acetone (10 ml) was mixed with para-toluenesulfonic acid (monohydrate, 109 mg), and the mixture was refluxed for 8 hours. After addition of triethylamine (0.5 ml), the mixture was diluted with water and extracted with ethyl acetate. The organic phase was dried over magnesium sulfate and concentrated. The product with the molecular weight of 352.44 (C21H24N2O3); MS (ESI): 353 (M+H+) was obtained in this way.

4-(1,4-Dioxa-7-azaspiro[4.4]non-7-yl)phenylamine

Trimethylchlorosilane (9.3 g) was slowly added to a solution of 1-benzyl-3-pyrrolidinone (5.0 g) in dichloromethane (30 ml) and ethylene glycol (2.67 g). After 18 hours, the mixture was poured into sodium hydroxide solution (1N). The organic phase was separated off, dried over magnesium sulfate and concentrated. The residue was dissolved in methanol (30 ml), and ammonium formate (5.2 g) and palladium hydroxide (10% on carbon, 300 mg) were added. The mixture was refluxed for 8 hours, filtered and concentrated. The residue was reacted with 4-fluoronitrobenzene by method C. Finally, hydrogenation by method B was carried out. The product with the molecular weight of 220.27 (C12H16N2O2); MS (ESI): 221 (M+H+) was obtained in this way.

Further exemplary structures obtained by method A (for ureas) or E (for amides) are compiled in Table 2a and Table 2b.

TABLE 2a

| Ex. No. | Structure | Molecular formula | Molecular weight | ESI-MS [M + H]+ |
|---|---|---|---|---|
| 11 | 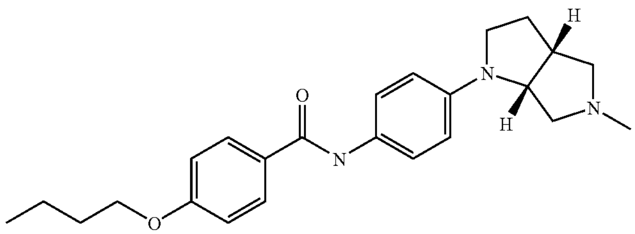 [SMILES: CCCCOc1ccc(C(=O)Nc2ccc(N3CC[C@@H]4CN(C)C[C@@H]43)cc2)cc1] | C24H31N3O2 | 393.53 | 394 |
| 12 | 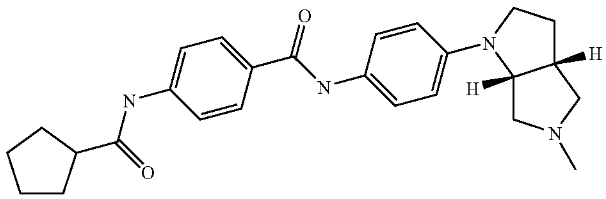 [SMILES: CN1C[C@H]2CCN(c3ccc(NC(=O)c4ccc(NC(=O)C5CCCC5)cc4)cc3)[C@H]2C1] | C26H32N4O2 | 432.57 | 433 |
| 13 | 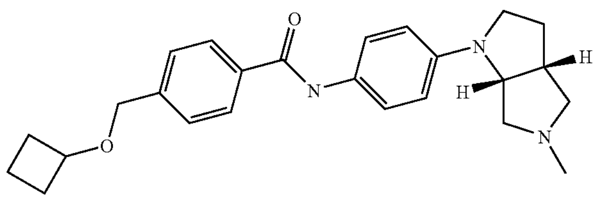 [SMILES: CN1C[C@H]2CCN(c3ccc(NC(=O)c4ccc(COC5CCC5)cc4)cc3)[C@H]2C1] | C25H31N3O2 | 405.54 | 406 |
| 14 | 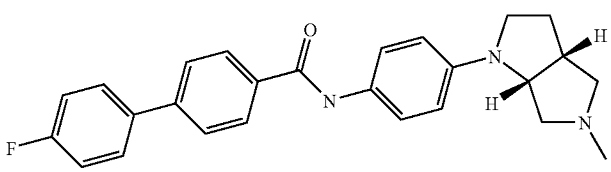 [SMILES: CN1C[C@H]2CCN(c3ccc(NC(=O)c4ccc(-c5ccc(F)cc5)cc4)cc3)[C@H]2C1] | C26H26FN3O | 415.52 | 416 |
| 15 | 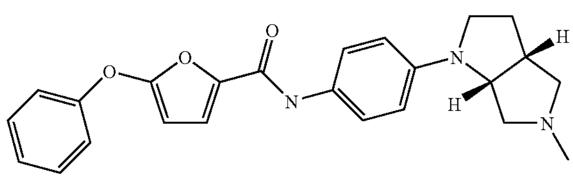 [SMILES: CN1C[C@H]2CCN(c3ccc(NC(=O)c4ccc(Oc5ccccc5)o4)cc3)[C@H]2C1] | C24H25N3O3 | 403.49 | 404 |
| 16 | 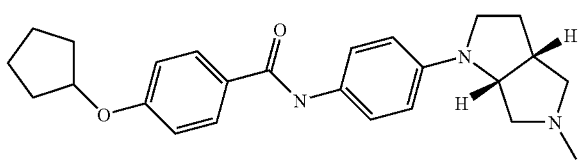 [SMILES: CN1C[C@H]2CCN(c3ccc(NC(=O)c4ccc(OC5CCCC5)cc4)cc3)[C@H]2C1] | C25H31N3O2 | 405.54 | 406 |
| 17 | 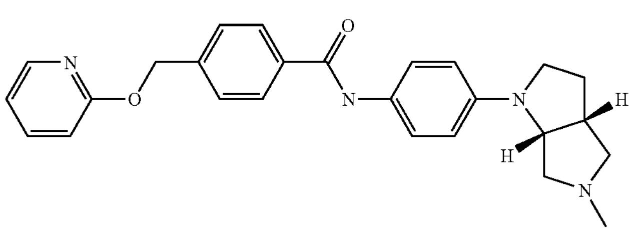 [SMILES: CN1C[C@H]2CCN(c3ccc(NC(=O)c4ccc(COc5ccccn5)cc4)cc3)[C@H]2C1] | C26H28N4O2 | 428.54 | 429 |

TABLE 2a-continued

| Ex. No. | Structure | Molecular formula | Molecular weight | ESI-MS [M + H]+ |
|---|---|---|---|---|
| 18 | 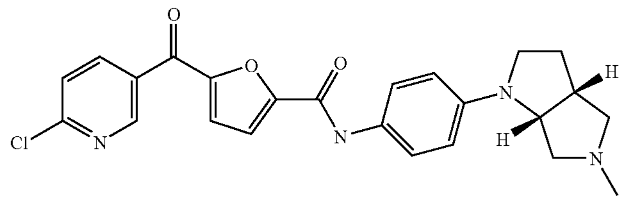 [SMILES: CN1C[C@H]2CCN(c3ccc(NC(=O)c4ccc(C(=O)c5ccc(Cl)nc5)o4)cc3)[C@H]2C1] | C24H23ClN4O3 | 450.93 | 451 |
| 19 | 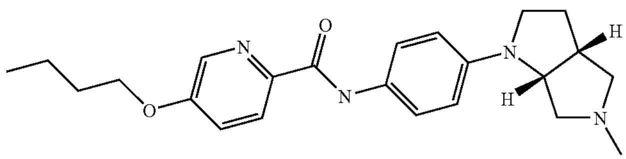 [SMILES: CCCCOc1ccc(C(=O)Nc2ccc(N3CC[C@@H]4CN(C)C[C@@H]43)cc2)nc1] | C23H30N4O2 | 394.52 | 395 |
| 20 | 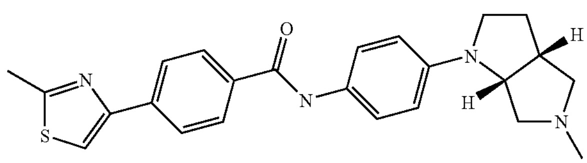 | C24H26N4OS | 418.57 | 419 |
| 21 | 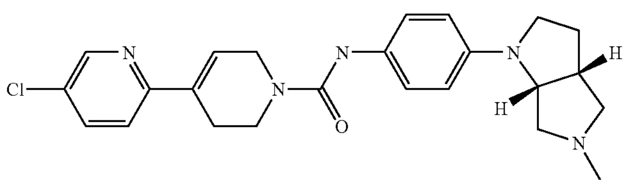 | C24H28ClN5O | 437.98 | 438 |
| 22 | 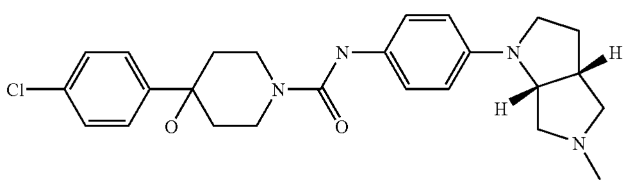 | C25H31ClN4O2 | 455.00 | 455 |
| 23 | 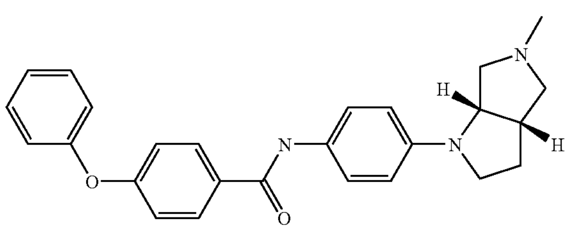 [SMILES: CN1C[C@@H]2CCN(c3ccc(NC(=O)c4ccc(Oc5ccccc5)cc4)cc3)[C@@H]2C1] | C26H27N3O2 | 413.52 | 414 |
| 24 | 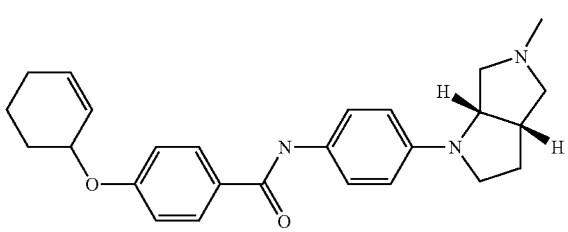 [SMILES: CN1C[C@@H]2CCN(c3ccc(NC(=O)c4ccc(OC5C=CCCC5)cc4)cc3)[C@@H]2C1] | C26H31N3O2 | 417.56 | 418 |
| 25 | 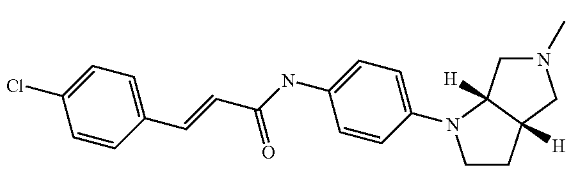 [SMILES: CN1C[C@@H]2CCN(c3ccc(NC(=O)/C=C/c4ccc(Cl)cc4)cc3)[C@@H]2C1] | C22H24ClN3O | 381.91 | 382 |

TABLE 2a-continued

| Ex. No. | Structure | Molecular formula | Molecular weight | ESI-MS [M + H]+ |
|---|---|---|---|---|
| 26 | 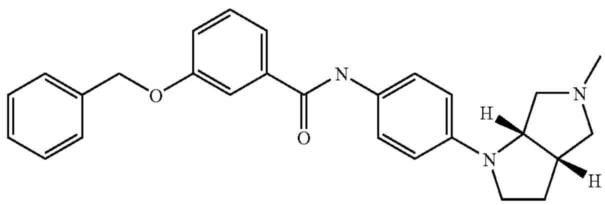 [SMILES: CN1C[C@@H]2CCN(c3ccc(NC(=O)c4cccc(OCc5ccccc5)c4)cc3)[C@@H]2C1] | C27H29N3O2 | 427.55 | 428 |
| 27 | 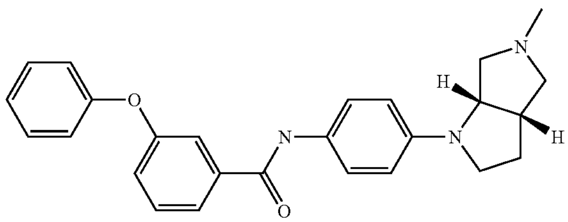 [SMILES: CN1C[C@@H]2CCN(c3ccc(NC(=O)c4cccc(Oc5ccccc5)c4)cc3)[C@@H]2C1] | C26H27N3O2 | 413.52 | 414 |
| 28 | 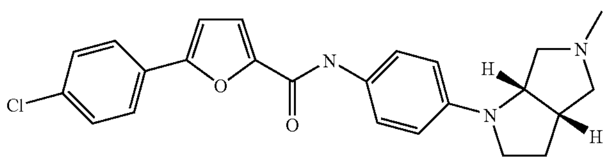 [SMILES: CN1C[C@@H]2CCN(c3ccc(NC(=O)c4ccc(-c5ccc(Cl)cc5)o4)cc3)[C@@H]2C1] | C24H24ClN3O2 | 421.93 | 422 |
| 29 | 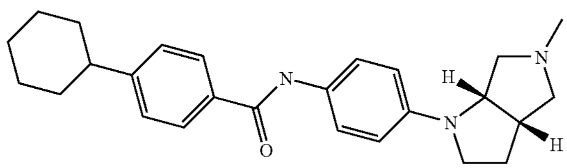 [SMILES: CN1C[C@@H]2CCN(c3ccc(NC(=O)c4ccc(C5CCCCC5)cc4)cc3)[C@@H]2C1] | C26H33N3O | 403.57 | 404 |
| 30 | 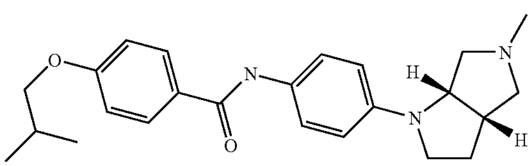 [SMILES: CC(C)COc1ccc(C(=O)Nc2ccc(N3CC[C@H]4CN(C)C[C@H]43)cc2)cc1] | C24H31N3O2 | 393.53 | 394 |
| 31 | 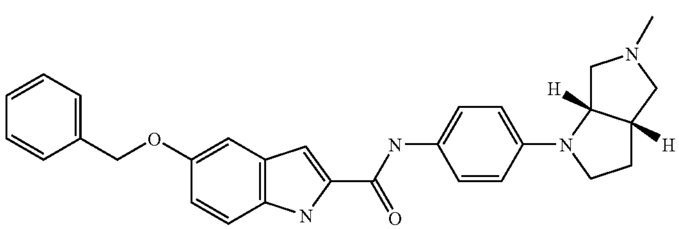 [SMILES: CN1C[C@@H]2CCN(c3ccc(NC(=O)c4cc5cc(OCc6ccccc6)ccc5[nH]4)cc3)[C@@H]2C1] | C29H30N4O2 | 466.59 | 467 |
| 32 | 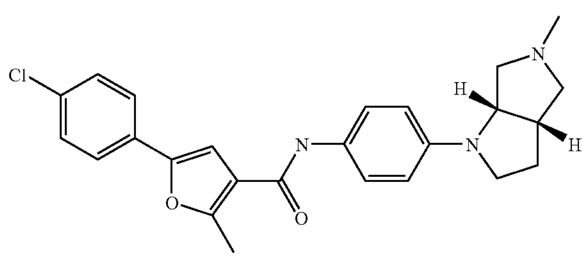 [SMILES: Cc1oc(-c2ccc(Cl)cc2)cc1C(=O)Nc1ccc(N2CC[C@H]3CN(C)C[C@H]32)cc1] | C25H26ClN3O2 | 435.96 | 436 |
| 33 | 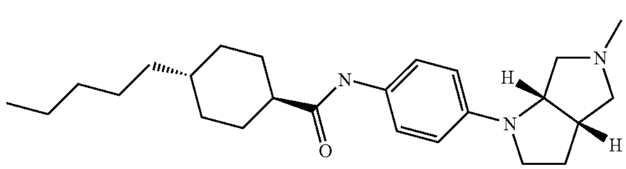 [SMILES: CCCCC[C@H]1CC[C@H](C(=O)Nc2ccc(N3CC[C@H]4CN(C)C[C@H]43)cc2)CC1] | C25H39N3O | 397.61 | 398 |

TABLE 2a-continued

| Ex. No. | Structure | Molecular formula | Molecular weight | ESI-MS [M + H]+ |
|---|---|---|---|---|
| 34 | 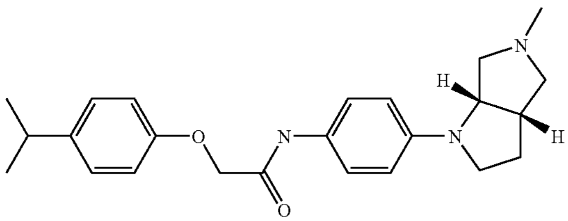 [SMILES: CC(C)c1ccc(OCC(=O)Nc2ccc(N3CC[C@H]4CN(C)C[C@H]43)cc2)cc1] | C24H31N3O2 | 393.53 | 394 |
| 35 | 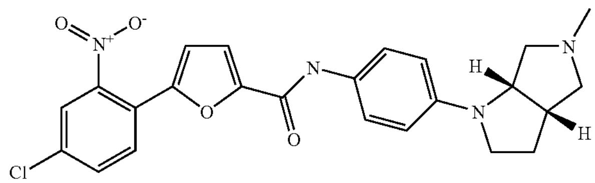 [SMILES: CN1C[C@@H]2CCN(c3ccc(NC(=O)c4ccc(-c5ccc(Cl)cc5[N+](=O)[O-])o4)cc3)[C@@H]2C1] | C24H23ClN4O4 | 466.93 | 467 |
| 36 | 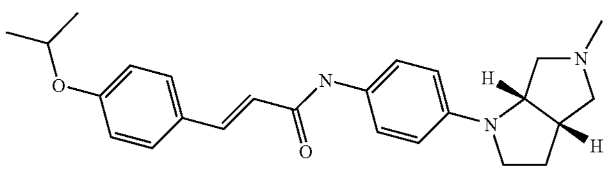 [SMILES: CC(C)Oc1ccc(/C=C/C(=O)Nc2ccc(N3CC[C@H]4CN(C)C[C@H]43)cc2)cc1] | C25H31N3O2 | 405.54 | 406 |
| 37 | 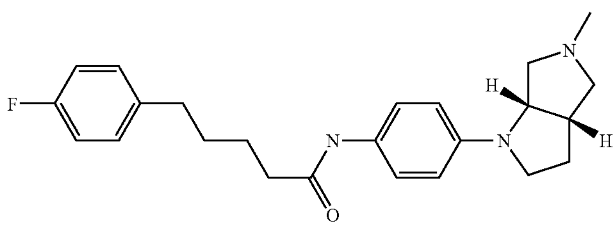 [SMILES: CN1C[C@@H]2CCN(c3ccc(NC(=O)CCCCc4ccc(F)cc4)cc3)[C@@H]2C1] | C24H30FN3O | 395.52 | 396 |
| 38 | 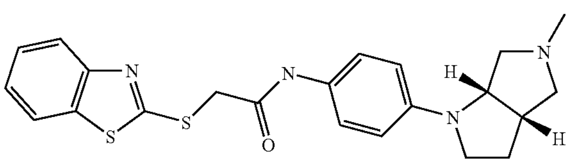 [SMILES: CN1C[C@@H]2CCN(c3ccc(NC(=O)CSc4nc5ccccc5s4)cc3)[C@@H]2C1] | C22H24N4OS2 | 424.59 | 425 |
| 39 | 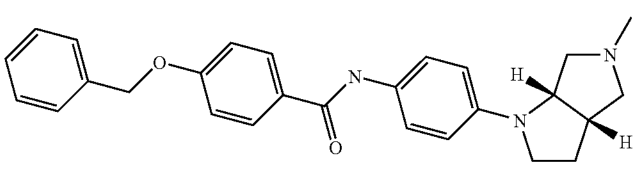 [SMILES: CN1C[C@@H]2CCN(c3ccc(NC(=O)c4ccc(OCc5ccccc5)cc4)cc3)[C@@H]2C1] | C27H29N3O2 | 427.55 | 428 |
| 40 | 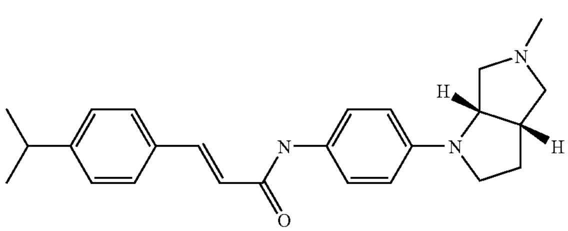 [SMILES: CC(C)c1ccc(/C=C/C(=O)Nc2ccc(N3CC[C@H]4CN(C)C[C@H]43)cc2)cc1] | C25H31N3O | 389.55 | 390 |

TABLE 2a-continued

| Ex. No. | Structure | Molecular formula | Molecular weight | ESI-MS [M + H]+ |
|---|---|---|---|---|
| 41 | 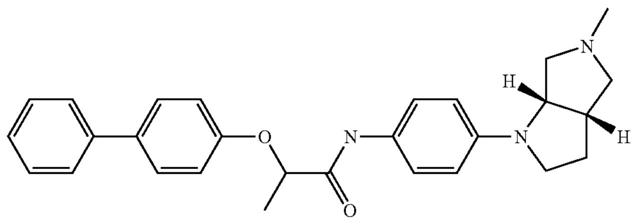 [SMILES: CC(Oc1ccc(-c2ccccc2)cc1)C(=O)Nc1ccc(N2CC[C@H]3CN(C)C[C@H]32)cc1] | C28H31N3O2 | 441.58 | 442 |
| 42 | 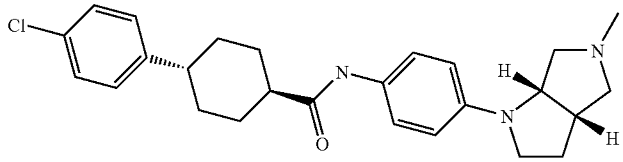 [SMILES: CN1C[C@@H]2CCN(c3ccc(NC(=O)[C@H]4CC[C@H](c5ccc(Cl)cc5)CC4)cc3)[C@@H]2C1] | C26H32ClN3O | 438.02 | 438 |
| 43 | 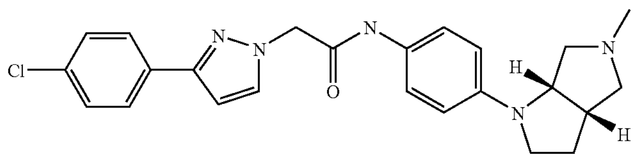 [SMILES: CN1C[C@@H]2CCN(c3ccc(NC(=O)Cn4ccc(-c5ccc(Cl)cc5)n4)cc3)[C@@H]2C1] | C24H26ClN5O | 435.96 | 436 |
| 44 | 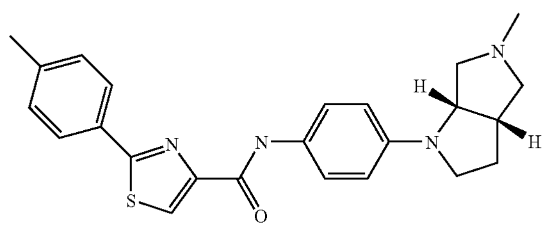 [SMILES: Cc1ccc(-c2nc(C(=O)Nc3ccc(N4CC[C@H]5CN(C)C[C@H]54)cc3)cs2)cc1] | C24H26N4OS | 418.57 | 419 |
| 45 | 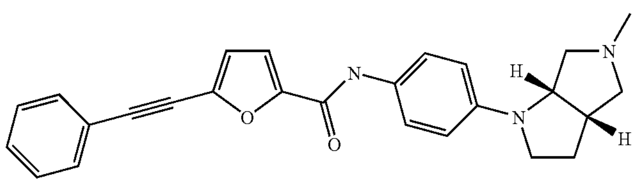 [SMILES: CN1C[C@@H]2CCN(c3ccc(NC(=O)c4ccc(C#Cc5ccccc5)o4)cc3)[C@@H]2C1] | C26H25N3O2 | 411.51 | 412 |
| 46 | 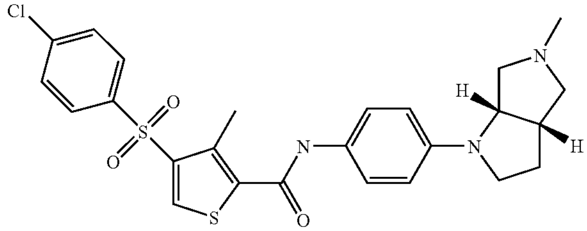 [SMILES: Cc1c(S(=O)(=O)c2ccc(Cl)cc2)csc1C(=O)Nc1ccc(N2CC[C@H]3CN(C)C[C@H]32)cc1] | C25H26ClN3O3S2 | 516.09 | 516 |
| 47 | 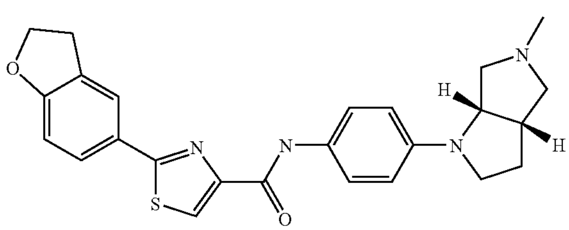 [SMILES: CN1C[C@@H]2CCN(c3ccc(NC(=O)c4csc(-c5ccc6c(c5)CCO6)n4)cc3)[C@@H]2C1] | C25H26N4O2S | 446.58 | 447 |

TABLE 2a-continued

| Ex. No. | Structure | Molecular formula | Molecular weight | ESI-MS [M + H]+ |
|---|---|---|---|---|
| 48 | 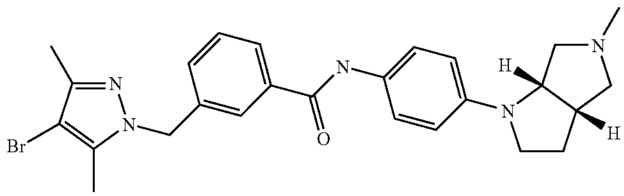 [SMILES: Cc1nn(Cc2cccc(C(=O)Nc3ccc(N4CC[C@H]5CN(C)C[C@H]54)cc3)c2)c(C)c1Br] | C26H30BrN5O | 508.47 | 509 |
| 49 | 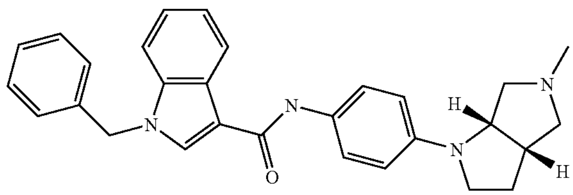 [SMILES: CN1C[C@@H]2CCN(c3ccc(NC(=O)c4cn(Cc5ccccc5)c5ccccc45)cc3)[C@@H]2C1] | C29H30N4O | 450.59 | 451 |
| 50 | 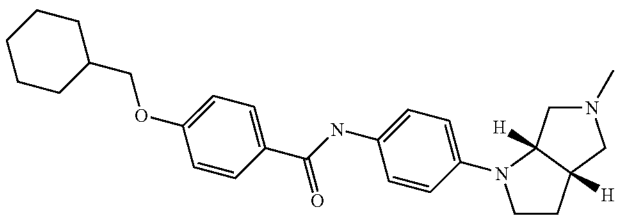 [SMILES: CN1C[C@@H]2CCN(c3ccc(NC(=O)c4ccc(OCC5CCCCC5)cc4)cc3)[C@@H]2C1] | C27H35N3O2 | 433.60 | 434 |
| 51 | 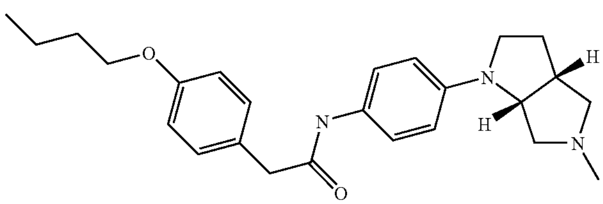 [SMILES: CCCCOc1ccc(CC(=O)Nc2ccc(N3CC[C@@H]4CN(C)C[C@@H]43)cc2)cc1] | C25H33N3O2 | 407.56 | 408 |
| 52 | 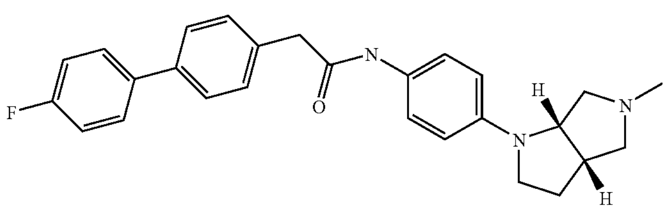 [SMILES: CN1C[C@@H]2CCN(c3ccc(NC(=O)Cc4ccc(-c5ccc(F)cc5)cc4)cc3)[C@@H]2C1] | C27H28FN3O | 429.54 | 430 |
| 53 | 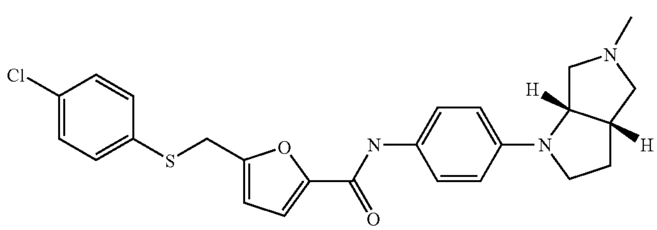 [SMILES: CN1C[C@@H]2CCN(c3ccc(NC(=O)c4ccc(CSc5ccc(Cl)cc5)o4)cc3)[C@@H]2C1] | C25H26ClN3O2S | 468.02 | 468 |
| 54 | 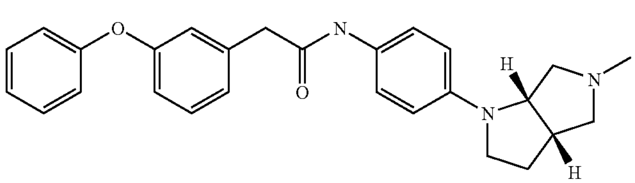 [SMILES: CN1C[C@@H]2CCN(c3ccc(NC(=O)Cc4cccc(Oc5ccccc5)c4)cc3)[C@@H]2C1] | C27H29N3O2 | 427.55 | 428 |

TABLE 2a-continued

| Ex. No. | Structure | Molecular formula | Molecular weight | ESI-MS [M + H]+ |
|---|---|---|---|---|
| 55 | 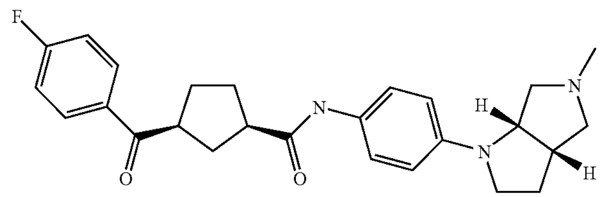 [SMILES: CN1C[C@@H]2CCN(c3ccc(NC(=O)[C@@H]4CC[C@H](C(=O)c5ccc(F)cc5)C4)cc3)[C@@H]2C1] | C26H30FN3O2 | 435.55 | 436 |
| 56 | 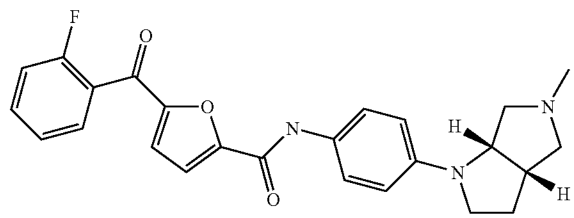 [SMILES: CN1C[C@@H]2CCN(c3ccc(NC(=O)c4ccc(C(=O)c5ccccc5F)o4)cc3)[C@@H]2C1] | C25H24FN3O3 | 433.49 | 434 |
| 57 | 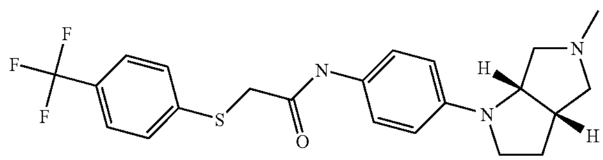 [SMILES: CN1C[C@@H]2CCN(c3ccc(NC(=O)CSc4ccc(C(F)(F)F)cc4)cc3)[C@@H]2C1] | C22H24F3N3OS | 435.52 | 436 |
| 58 | 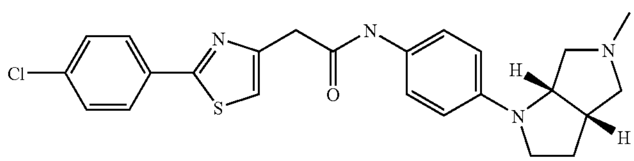 [SMILES: CN1C[C@@H]2CCN(c3ccc(NC(=O)Cc4csc(-c5ccc(Cl)cc5)n4)cc3)[C@@H]2C1] | C24H25ClN4OS | 453.01 | 453 |
| 59 | 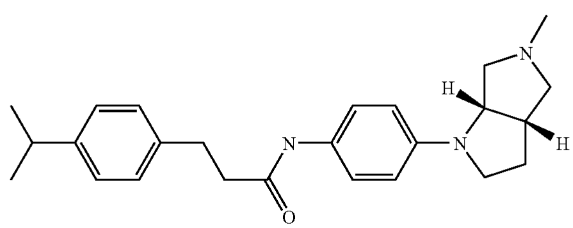 [SMILES: CC(C)c1ccc(CCC(=O)Nc2ccc(N3CC[C@H]4CN(C)C[C@H]43)cc2)cc1] | C25H33N3O | 391.56 | 392 |
| 60 | 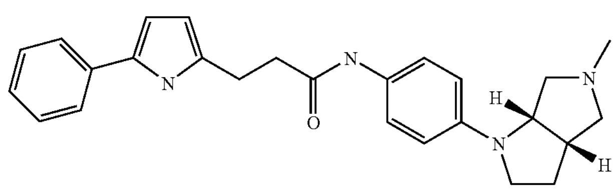 [SMILES: CN1C[C@@H]2CCN(c3ccc(NC(=O)CCc4ccc(-c5ccccc5)[nH]4)cc3)[C@@H]2C1] | C26H30N4O | 414.56 | 415 |
| 61 | 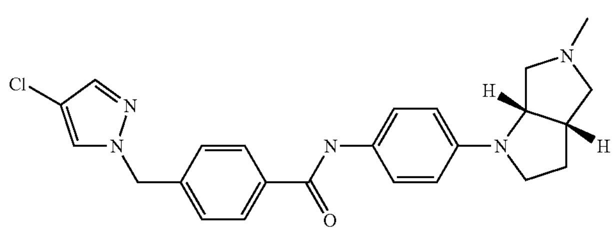 [SMILES: CN1C[C@@H]2CCN(c3ccc(NC(=O)c4ccc(Cn5cc(Cl)cn5)cc4)cc3)[C@@H]2C1] | C24H26ClN5O | 435.96 | 436 |
| 62 | 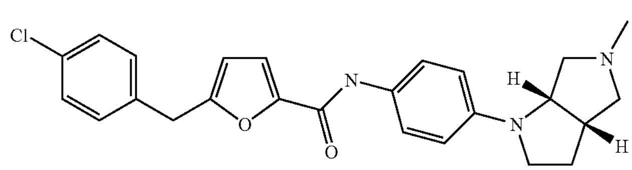 [SMILES: CN1C[C@@H]2CCN(c3ccc(NC(=O)c4ccc(Cc5ccc(Cl)cc5)o4)cc3)[C@@H]2C1] | C25H26ClN3O2 | 435.96 | 436 |

TABLE 2a-continued

| Ex. No. | Structure | Molecular formula | Molecular weight | ESI-MS [M + H]+ |
|---|---|---|---|---|
| 63 | 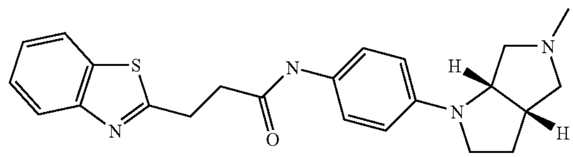 [SMILES: CN1C[C@@H]2CCN(c3ccc(NC(=O)CCc4nc5ccccc5s4)cc3)[C@@H]2C1] | C23H26N4OS | 406.55 | 407 |
| 64 | 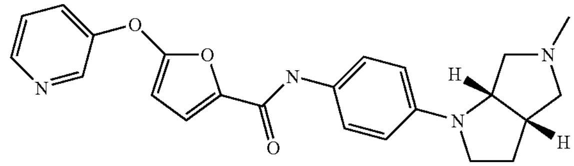 [SMILES: CN1C[C@@H]2CCN(c3ccc(NC(=O)c4ccc(Oc5cccnc5)o4)cc3)[C@@H]2C1] | C23H24N4O3 | 404.47 | 405 |
| 65 | 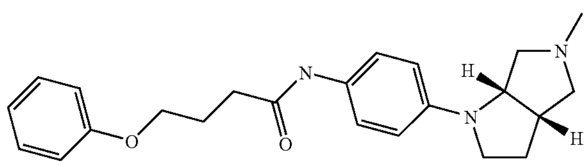 [SMILES: CN1C[C@@H]2CCN(c3ccc(NC(=O)CCCOc4ccccc4)cc3)[C@@H]2C1] | C23H29N3O2 | 379.51 | 380 |
| 66 | 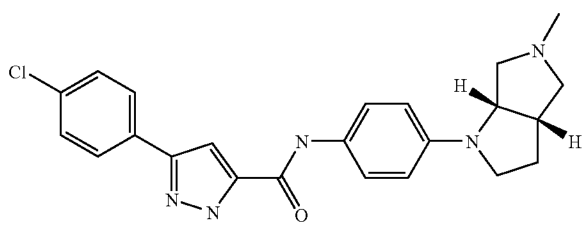 [SMILES: CN1C[C@@H]2CCN(c3ccc(NC(=O)c4cc(-c5ccc(Cl)cc5)n[nH]4)cc3)[C@@H]2C1] | C23H24ClN5O | 421.93 | 422 |
| 67 | 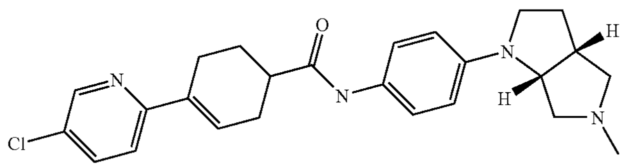 [SMILES: CN1C[C@H]2CCN(c3ccc(NC(=O)C4CC=C(c5ccc(Cl)cn5)CC4)cc3)[C@H]2C1] | C25H29ClN4O | 436.99 | 437 |
| 68 | 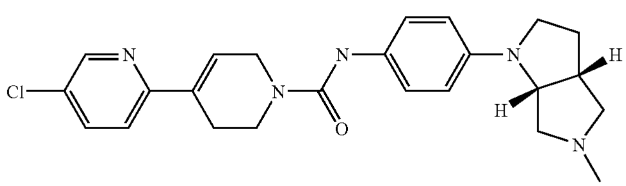 [SMILES: CN1C[C@H]2CCN(c3ccc(NC(=O)N4CC=C(c5ccc(Cl)cn5)CC4)cc3)[C@H]2C1] | C24H28ClN5O | 437.98 | 438 |
| 69 | 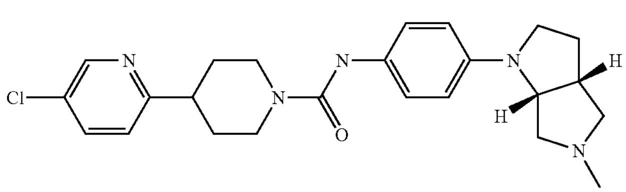 [SMILES: CN1C[C@H]2CCN(c3ccc(NC(=O)N4CCC(c5ccc(Cl)cn5)CC4)cc3)[C@H]2C1] | C24H30ClN5O | 439.99 | 440 |
| 70 | 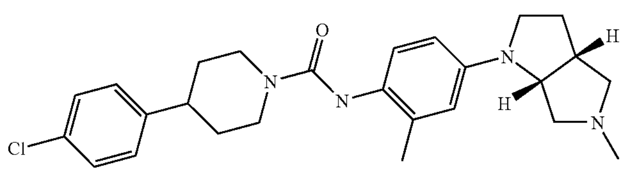 [SMILES: Cc1cc(N2CC[C@@H]3CN(C)C[C@@H]32)ccc1NC(=O)N1CCC(c2ccc(Cl)cc2)CC1] | C26H33ClN4O | 453.03 | 453 |

TABLE 2a-continued

| Ex. No. | Structure | Molecular formula | Molecular weight | ESI-MS [M + H]+ |
|---|---|---|---|---|
| 71 | 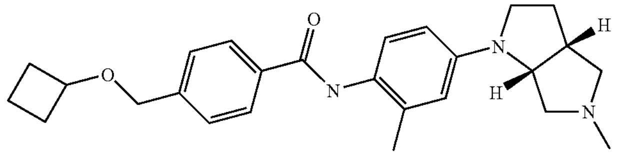 [SMILES: Cc1cc(N2CC[C@@H]3CN(C)C[C@@H]32)ccc1NC(=O)c1ccc(COC2CCC2)cc1] | C26H33N3O2 | 419.57 | 420 |
| 72 | 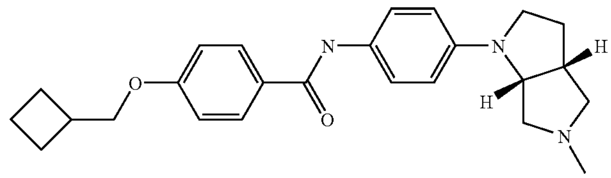 [SMILES: CN1C[C@H]2CCN(c3ccc(NC(=O)c4ccc(OCC5CCC5)cc4)cc3)[C@H]2C1] | C25H31N3O2 | 405.54 | 406 |
| 73 | 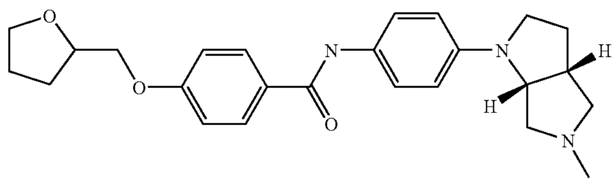 [SMILES: CN1C[C@H]2CCN(c3ccc(NC(=O)c4ccc(OCC5CCCO5)cc4)cc3)[C@H]2C1] | C25H31N3O3 | 421.54 | 422 |
| 74 | 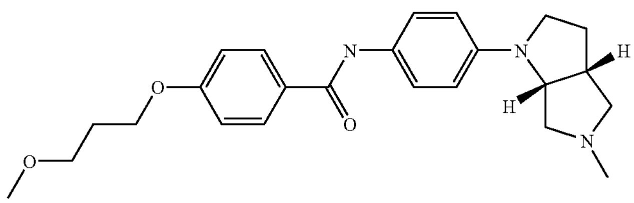 [SMILES: COCCCOc1ccc(C(=O)Nc2ccc(N3CC[C@@H]4CN(C)C[C@@H]43)cc2)cc1] | C24H31N3O3 | 409.53 | 410 |
| 75 | 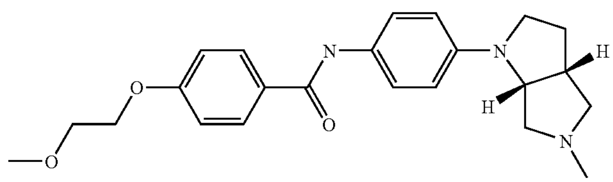 [SMILES: COCCOc1ccc(C(=O)Nc2ccc(N3CC[C@@H]4CN(C)C[C@@H]43)cc2)cc1] | C23H29N3O3 | 395.51 | 396 |
| 76 | 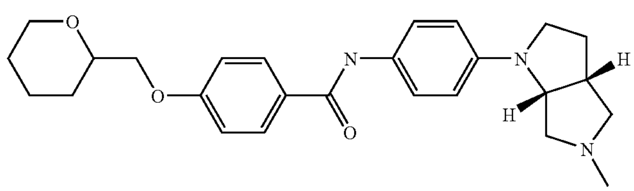 [SMILES: CN1C[C@H]2CCN(c3ccc(NC(=O)c4ccc(OCC5CCCCO5)cc4)cc3)[C@H]2C1] | C26H33N3O3 | 435.57 | 436 |
| 77 | 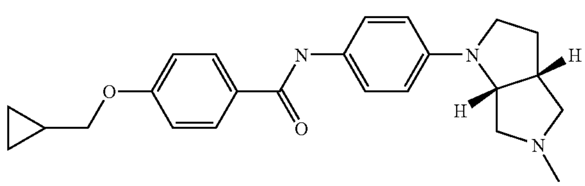 [SMILES: CN1C[C@H]2CCN(c3ccc(NC(=O)c4ccc(OCC5CC5)cc4)cc3)[C@H]2C1] | C24H29N3O2 | 391.52 | 392 |
| 78 | 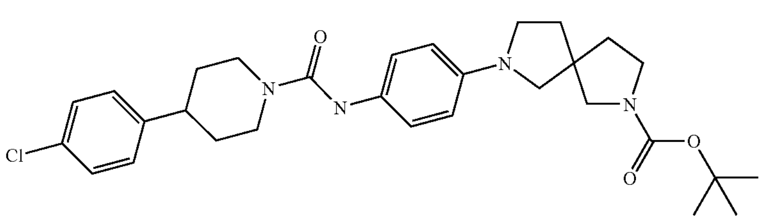 [SMILES: CC(C)(C)OC(=O)N1CCC2(CCN(c3ccc(NC(=O)N4CCC(c5ccc(Cl)cc5)CC4)cc3)C2)C1] | C30H39ClN4O3 | 539.12 | 540 |

TABLE 2a-continued

| Ex. No. | Structure | Molecular formula | Molecular weight | ESI-MS [M + H]+ |
|---|---|---|---|---|
| 79 | 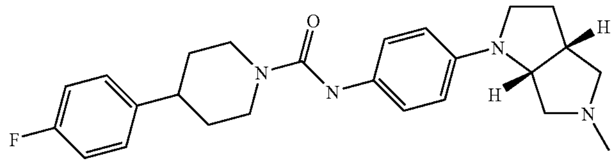 [SMILES: CN1C[C@H]2CCN(c3ccc(NC(=O)N4CCC(c5ccc(F)cc5)CC4)cc3)[C@H]2C1] | C25H31FN4O | 422.55 | 423 |
| 80 | 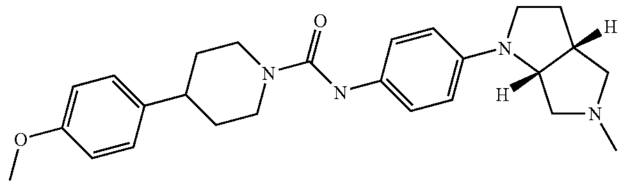 | C26H34N4O2 | 434.59 | 435 |
| 81 | 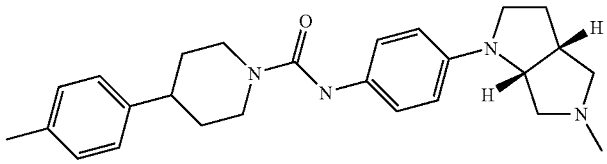 | C26H34N4O | 418.59 | 419 |
| 82 | 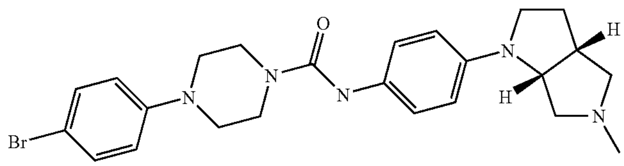 [SMILES: CN1C[C@H]2CCN(c3ccc(NC(=O)N4CCN(c5ccc(Br)cc5)CC4)cc3)[C@H]2C1] | C24H30BrN5O | 484.44 | 485 |
| 83 | 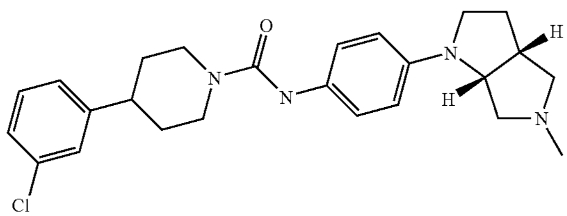 [SMILES: CN1C[C@H]2CCN(c3ccc(NC(=O)N4CCC(c5cccc(Cl)c5)CC4)cc3)[C@H]2C1] | C25H31ClN4O | 439.01 | 440 |
| 84 | 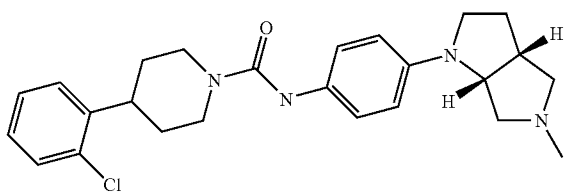 [SMILES: CN1C[C@H]2CCN(c3ccc(NC(=O)N4CCC(c5ccccc5Cl)CC4)cc3)[C@H]2C1] | C25H31ClN4O | 439.01 | 440 |
| 85 | 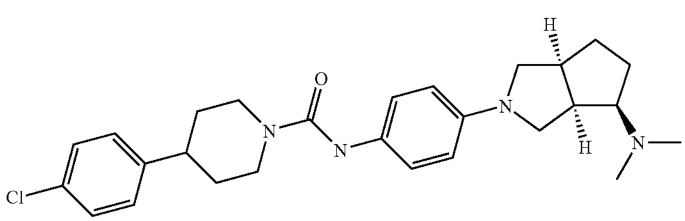 [SMILES: CN(C)[C@@H]1CC[C@@H]2CN(c3ccc(NC(=O)N4CCC(c5ccc(Cl)cc5)CC4)cc3)C[C@@H]21] | C27H35ClN4O | 467.06 | 468 |
| 86 | 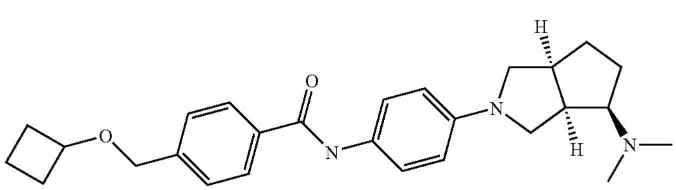 [SMILES: CN(C)[C@@H]1CC[C@@H]2CN(c3ccc(NC(=O)c4ccc(COC5CCC5)cc4)cc3)C[C@@H]21] | C27H35N3O2 | 433.60 | 434 |

TABLE 2a-continued

| Ex. No. | Structure | Molecular formula | Molecular weight | ESI-MS [M + H]+ |
|---|---|---|---|---|
| 87 | 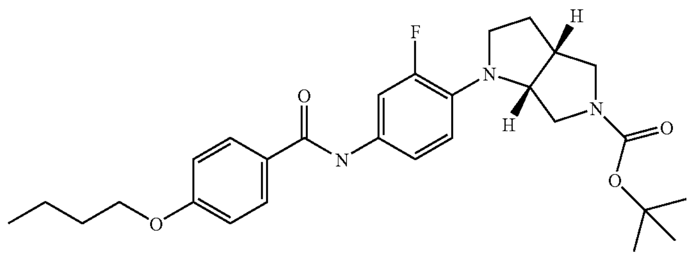 [SMILES: CCCCOc1ccc(C(=O)Nc2ccc(N3CC[C@@H]4CN(C(=O)OC(C)(C)C)C[C@@H]43)c(F)c2)cc1] | C28H36FN3O4 | 497.62 | 498 |
| 88 | 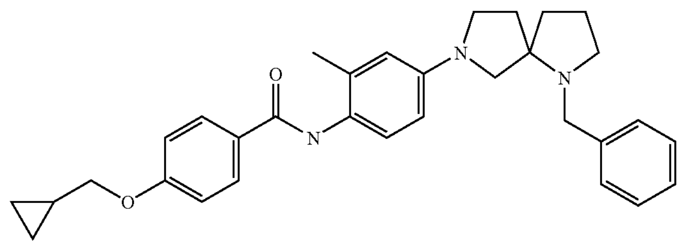 [SMILES: Cc1cc(N2CCC3(CCCN3Cc3ccccc3)C2)ccc1NC(=O)c1ccc(OCC2CC2)cc1] | C32H37N3O2 | 495.67 | 496 |

Table 3 is a compilation of examples which were obtained from the appropriate building blocks by Method A (for ureas) or E (for amides) and subsequent protective group elimination (Method D).

TABLE 3

| Ex. No. | Structure | Molecular formula | Molecular weight | ESI-MS [M + H]+ |
|---|---|---|---|---|
| 89 | 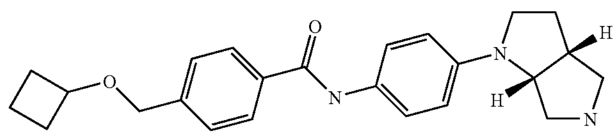 [SMILES: O=C(Nc1ccc(N2CC[C@@H]3CNC[C@@H]32)cc1)c1ccc(COC2CCC2)cc1] | C24H29N3O2 | 391.52 | 392 |
| 90 | 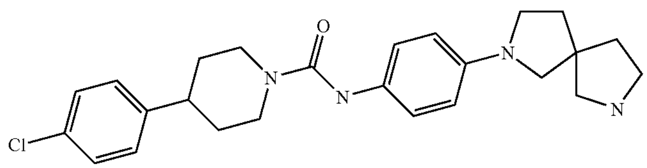 [SMILES: O=C(Nc1ccc(N2CCC3(CCNC3)C2)cc1)N1CCC(c2ccc(Cl)cc2)CC1] | C25H31ClN4O | 439.01 | 439 |
| 91 | 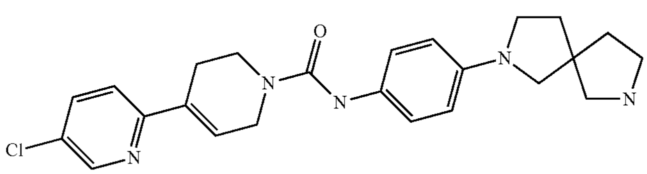 [SMILES: O=C(Nc1ccc(N2CCC3(CCNC3)C2)cc1)N1CC=C(c2ccc(Cl)cn2)CC1] | C24H28ClN5O | 437.98 | 438 |
| 92 | 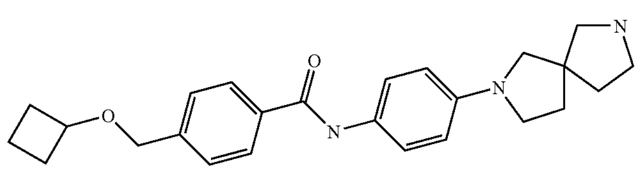 [SMILES: O=C(Nc1ccc(N2CCC3(CCNC3)C2)cc1)c1ccc(COC2CCC2)cc1] | C25H31N3O2 | 405.54 | 406 |
| 93 | 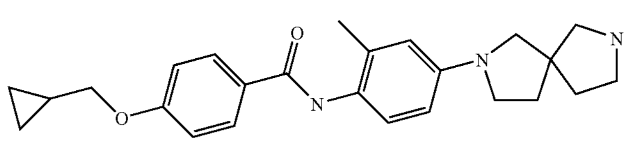 [SMILES: Cc1cc(N2CCC3(CCNC3)C2)ccc1NC(=O)c1ccc(OCC2CC2)cc1] | C25H31N3O2 | 405.54 | 406 |

TABLE 3-continued

| Ex. No. | Structure | Molecular formula | Molecular weight | ESI-MS [M + H]+ |
|---|---|---|---|---|
| 94 | 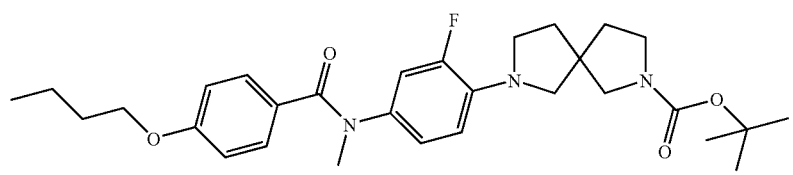 [SMILES: CCCCOc1ccc(C(=O)N(C)c2ccc(N3CCC4(CCN(C(=O)OC(C)(C)C)C4)C3)c(F)c2)cc1] | C23H28FN3O2 | 397.50 | 398 |

Example 95

7-{4-[(4-Butoxybenzoyl)methylamino]phenyl}-2,7-diazaspiro[4.4]nonane-2-carboxylic acid tert-butyl ester

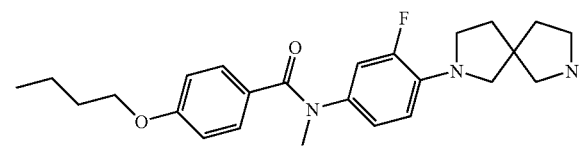 [SMILES: CCCCOc1ccc(C(=O)N(C)c2ccc(N3CCC4(CCNC4)C3)c(F)c2)cc1]

Sodium hydride (55% in oil; 20 mg) was added to 7-[4-(4-butoxy-benzoylamino)-2-fluorophenyl]-2,7-diazaspiro[4.4]nonane-2-carboxylic acid tert-butyl ester (210 mg) dissolved in DMF (5 ml) and, after gas evolution ceased, methyl iodide (25 μl) was added. After two hours, the mixture was hydrolyzed by adding water. The mixture was extracted with ethyl acetate. The organic phase was dried over sodium sulfate and concentrated. The product with the molecular weight of 525.67 (C30H40F1N3O4); MS (ESI): 526 (M+H+) was obtained in this way.

Example 96

4-Butoxy-N-[4-(2,7-diazaspiro[4.4]non-2-yl)-3-fluorophenyl]-N-methylbenzamide

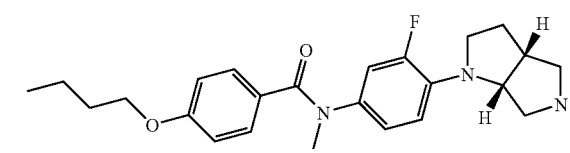 [SMILES: CCCCOc1ccc(C(=O)N(C)c2ccc(N3CC[C@@H]4CNC[C@@H]43)c(F)c2)cc1]

7-{4-[(4-Butoxybenzoyl)methylamino]phenyl}-2,7-diazaspiro[4.4]nonane-2-carboxylic acid tert-butyl ester was treated with trifluoroacetic acid by method D. The product with the molecular weight of 425.55 (C25H32F1N3O2); MS (ESI): 426 (M+H+) was obtained in this way.

Example 97

4-Butoxy-N-[3-fluoro-4-(hexahydropyrrolo[3,4-b]pyrrol-1-yl)-phenyl]-N-methylbenzamide 1-[4-(4-Butoxybenzoylamino)-2-fluorophenyl]hexahydropyrrolo[3,4-b]-pyrrole-5-carboxylic acid tert-butyl ester was reacted as described in examples 95 and 96. The product with the molecular weight of 411.52 (C24H30F1N3O2); MS (ESI): 412 (M+H+) was obtained in this way.

Example 98

4-Butoxy-N-[3-fluoro-4-(5-isopropylhexahydropyrrolo[3,4-b]pyrrol-1-yl)-phenyl]-N-methylbenzamine

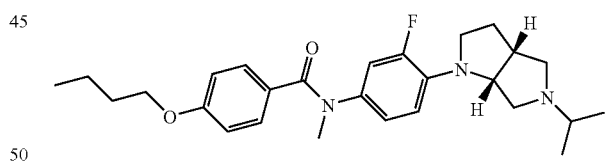

Method G

A mixture of 4-butoxy-N-[3-fluoro-4-(hexahydropyrrolo[3,4-b]pyrrol-1-yl)-phenyl]-N-methylbenzamide (50 mg), acetone (10 mg), acetic acid (7 mg), methanol (1 ml) and THF (2 ml) was mixed with sodium cyanoborohydride (polymer-bound; 0.12 mmol) and stirred for 12 h. The polymer was filtered off with suction and the filtrate was concentrated. The residue was purified by preparative HPLC. The product with the molecular weight of 453.61 (C27H36F1N3O2); MS (ESI): 454 (M+H+) was obtained in this way.

Further examples obtained by reductive amination by method G are compiled in table 4.

TABLE 4
| Ex. No. | Structure | Molecular formula | Molecular weight | ESI-MS [M + H]+ |
|---|---|---|---|---|
| 99 | 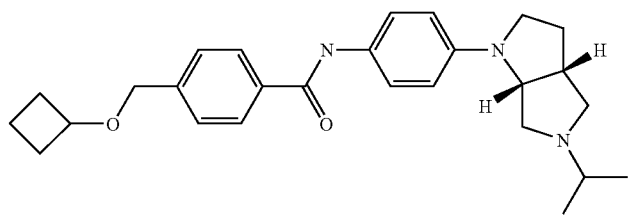 [SMILES: CC(C)N1C[C@H]2CCN(c3ccc(NC(=O)c4ccc(COC5CCC5)cc4)cc3)[C@H]2C1] | C27H35N3O2 | 433.60 | 434 |
| 100 | 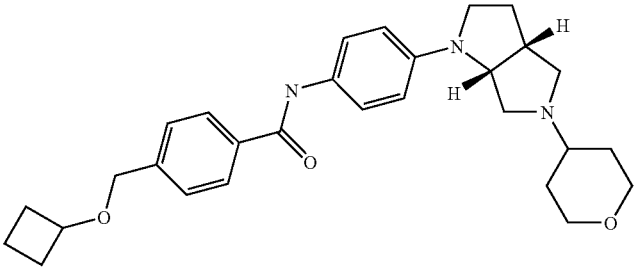 [SMILES: O=C(Nc1ccc(N2CC[C@@H]3CN(C4CCOCC4)C[C@@H]32)cc1)c1ccc(COC2CCC2)cc1] | C29H37N3O3 | 475.64 | 476 |
| 101 | 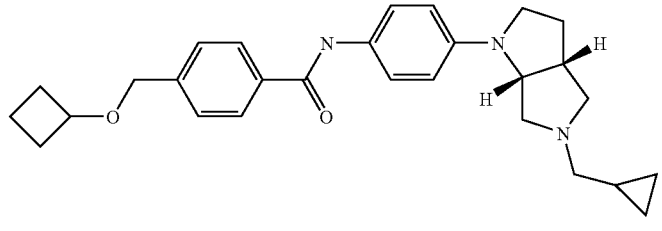 [SMILES: O=C(Nc1ccc(N2CC[C@@H]3CN(CC4CC4)C[C@@H]32)cc1)c1ccc(COC2CCC2)cc1] | C28H35N3O2 | 445.61 | 446 |
| 102 | 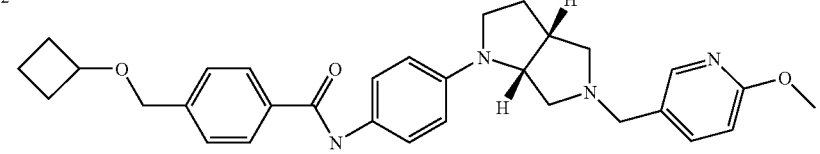 | C31H36N4O3 | 512.66 | 513 |
| 103 | 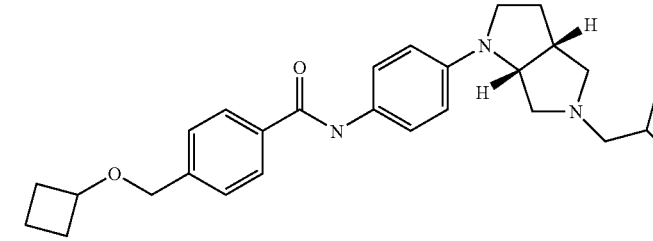 | C28H37N3O2 | 447.63 | 448 |
| 104 | 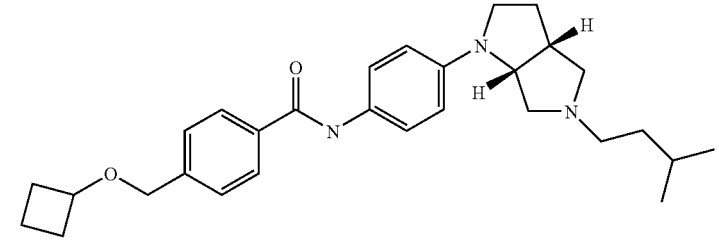 [SMILES: CC(C)CCN1C[C@H]2CCN(c3ccc(NC(=O)c4ccc(COC5CCC5)cc4)cc3)[C@H]2C1] | C29H39N3O2 | 461.65 | 462 |

TABLE 4-continued

| Ex. No. | Structure | Molecular formula | Molecular weight | ESI-MS [M + H]+ |
|---|---|---|---|---|
| 105 | 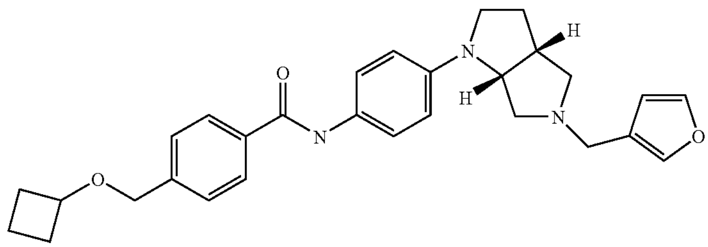 [SMILES: O=C(Nc1ccc(N2CC[C@@H]3CN(Cc4ccoc4)C[C@@H]32)cc1)c1ccc(COC2CCC2)cc1] | C29H33N3O3 | 471.60 | 472 |
| 106 | 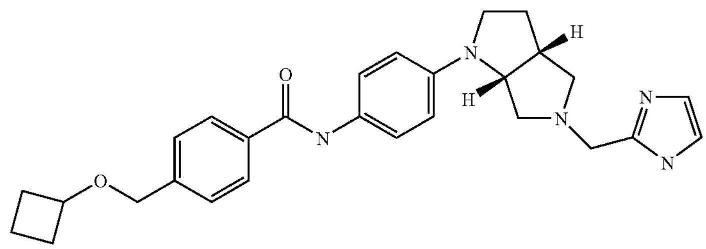 [SMILES: O=C(Nc1ccc(N2CC[C@@H]3CN(Cc4ncc[nH]4)C[C@@H]32)cc1)c1ccc(COC2CCC2)cc1] | C28H33N5O2 | 471.61 | 472 |
| 107 | 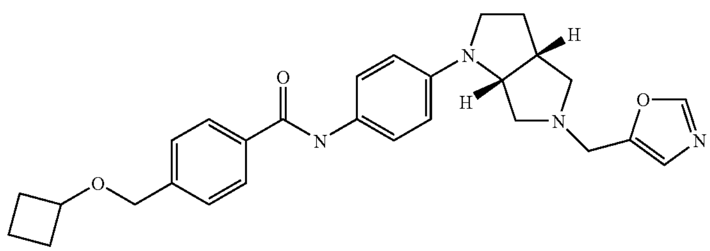 [SMILES: O=C(Nc1ccc(N2CC[C@@H]3CN(Cc4cnco4)C[C@@H]32)cc1)c1ccc(COC2CCC2)cc1] | C28H32N4O3 | 472.59 | 473 |
| 108 | 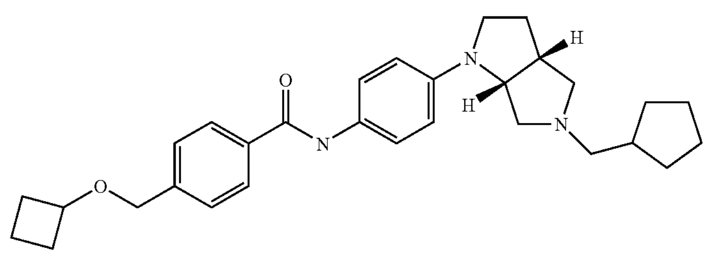 [SMILES: O=C(Nc1ccc(N2CC[C@@H]3CN(CC4CCCC4)C[C@@H]32)cc1)c1ccc(COC2CCC2)cc1] | C30H39N3O2 | 473.66 | 474 |
| 109 | 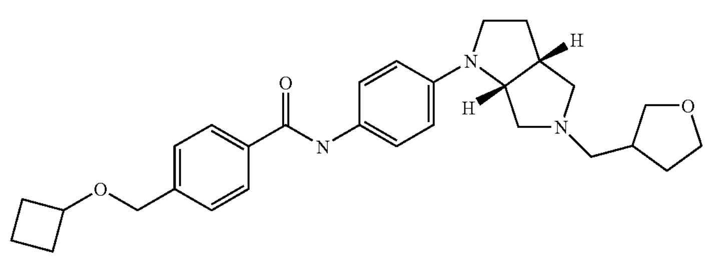 [SMILES: O=C(Nc1ccc(N2CC[C@@H]3CN(CC4CCOC4)C[C@@H]32)cc1)c1ccc(COC2CCC2)cc1] | C29H37N3O3 | 475.64 | 476 |
| 110 | 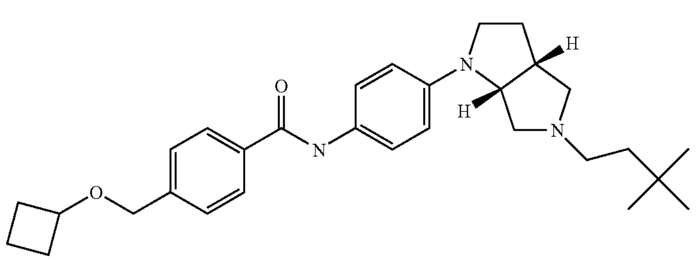 [SMILES: CC(C)(C)CCN1C[C@H]2CCN(c3ccc(NC(=O)c4ccc(COC5CCC5)cc4)cc3)[C@H]2C1] | C30H41N3O2 | 475.68 | 476 |

TABLE 4-continued

| Ex. No. | Structure | Molecular formula | Molecular weight | ESI-MS [M + H]+ |
|---------|-----------|-------------------|------------------|-----------------|
| 111 | 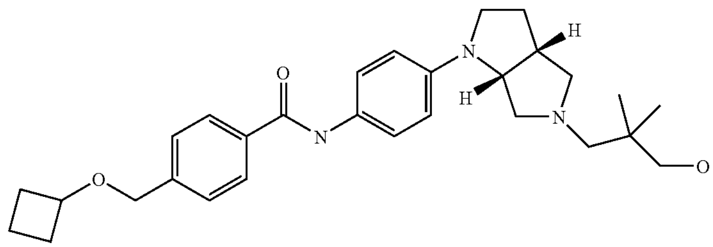 [SMILES: CC(C)(CO)CN1C[C@H]2CCN(c3ccc(NC(=O)c4ccc(COC5CCC5)cc4)cc3)[C@H]2C1] | C29H39N3O3 | 477.65 | 478 |
| 112 | 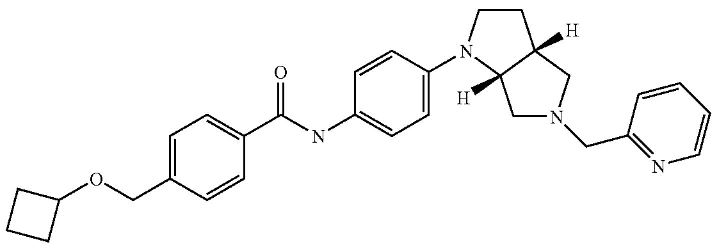 [SMILES: O=C(Nc1ccc(N2CC[C@@H]3CN(Cc4ccccn4)C[C@@H]32)cc1)c1ccc(COC2CCC2)cc1] | C30H34N4O2 | 482.63 | 483 |
| 113 | 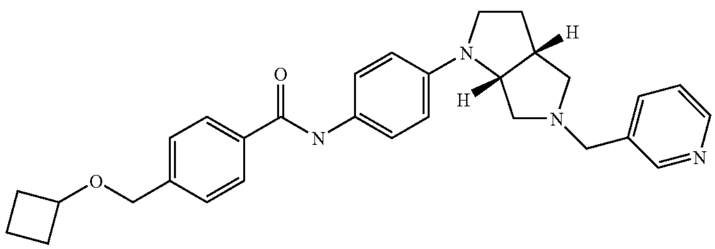 [SMILES: O=C(Nc1ccc(N2CC[C@@H]3CN(Cc4cccnc4)C[C@@H]32)cc1)c1ccc(COC2CCC2)cc1] | C30H34N4O2 | 482.63 | 483 |
| 114 | 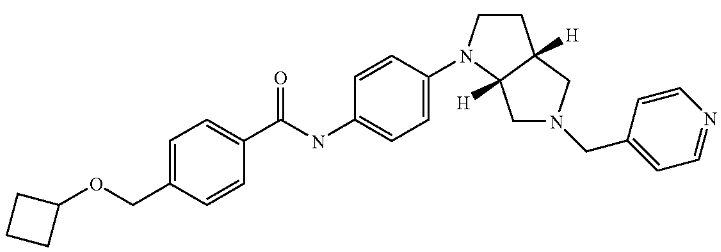 [SMILES: O=C(Nc1ccc(N2CC[C@@H]3CN(Cc4ccncc4)C[C@@H]32)cc1)c1ccc(COC2CCC2)cc1] | C30H34N4O2 | 482.63 | 483 |
| 115 | 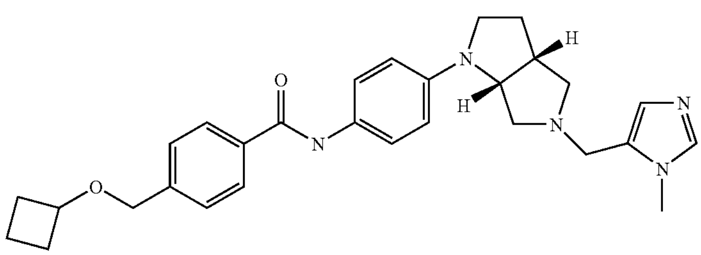 [SMILES: Cn1cncc1CN1C[C@H]2CCN(c3ccc(NC(=O)c4ccc(COC5CCC5)cc4)cc3)[C@H]2C1] | C29H35N5O2 | 485.63 | 486 |
| 116 | 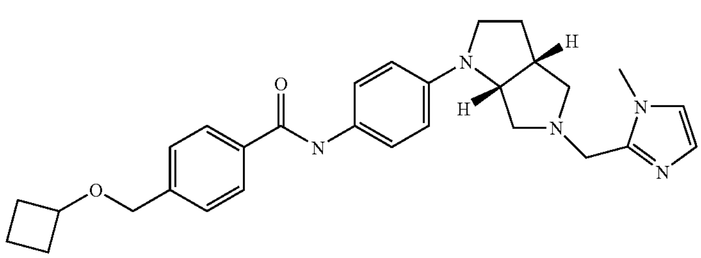 [SMILES: Cn1ccnc1CN1C[C@H]2CCN(c3ccc(NC(=O)c4ccc(COC5CCC5)cc4)cc3)[C@H]2C1] | C29H35N5O2 | 485.63 | 486 |

TABLE 4-continued

| Ex. No. | Structure | Molecular formula | Molecular weight | ESI-MS [M + H]+ |
|---|---|---|---|---|
| 117 | 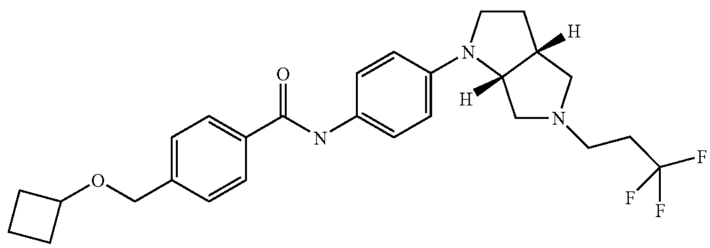 [SMILES: O=C(Nc1ccc(N2CC[C@@H]3CN(CCC(F)(F)F)C[C@@H]32)cc1)c1ccc(COC2CCC2)cc1] | C27H32F3N3O2 | 487.57 | 488 |
| 118 | 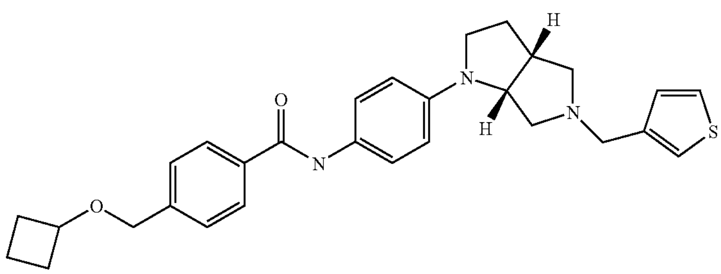 [SMILES: O=C(Nc1ccc(N2CC[C@@H]3CN(Cc4ccsc4)C[C@@H]32)cc1)c1ccc(COC2CCC2)cc1] | C29H33N3O2S | 487.67 | 488 |
| 119 | 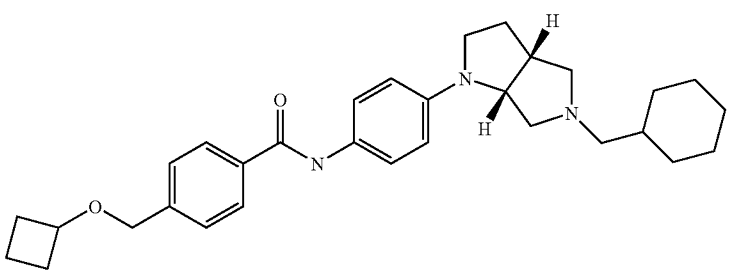 [SMILES: O=C(Nc1ccc(N2CC[C@@H]3CN(CC4CCCCC4)C[C@@H]32)cc1)c1ccc(COC2CCC2)cc1] | C31H41N3O2 | 487.69 | 488 |
| 120 | 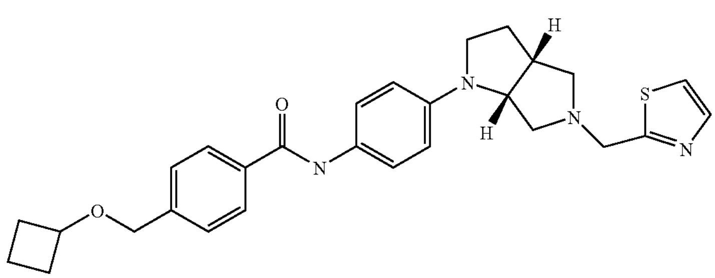 [SMILES: O=C(Nc1ccc(N2CC[C@@H]3CN(Cc4nccs4)C[C@@H]32)cc1)c1ccc(COC2CCC2)cc1] | C28H32N4O2S | 488.66 | 489 |
| 121 | 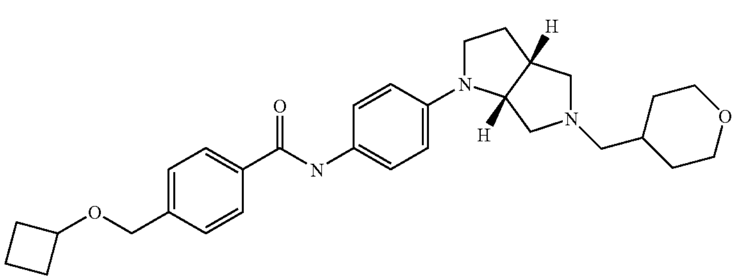 [SMILES: O=C(Nc1ccc(N2CC[C@@H]3CN(CC4CCOCC4)C[C@@H]32)cc1)c1ccc(COC2CCC2)cc1] | C30H39N3O3 | 489.66 | 490 |

TABLE 4-continued

| Ex. No. | Structure | Molecular formula | Molecular weight | ESI-MS [M + H]+ |
|---|---|---|---|---|
| 122 | 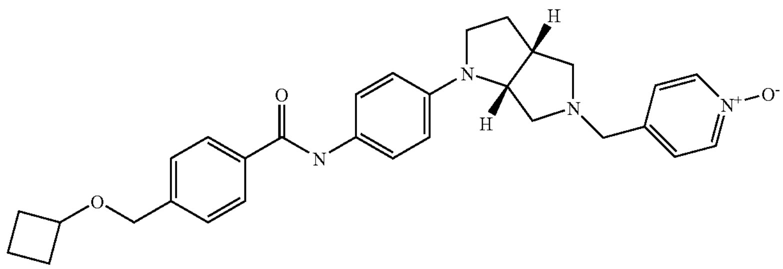 [SMILES: O=C(Nc1ccc(N2CC[C@@H]3CN(Cc4cc[n+]([O-])cc4)C[C@@H]32)cc1)c1ccc(COC2CCC2)cc1] | C30H34N4O3 | 498.63 | 499 |
| 123 | 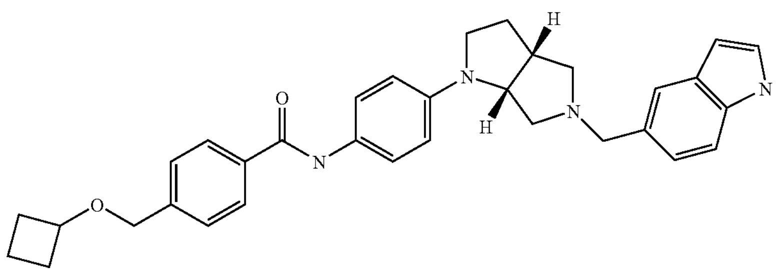 [SMILES: O=C(Nc1ccc(N2CC[C@@H]3CN(Cc4ccc5[nH]ccc5c4)C[C@@H]32)cc1)c1ccc(COC2CCC2)cc1] | C33H36N4O2 | 520.68 | 521 |
| 124 | 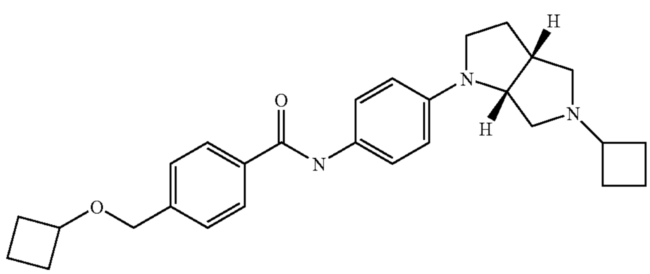 [SMILES: O=C(Nc1ccc(N2CC[C@@H]3CN(C4CCC4)C[C@@H]32)cc1)c1ccc(COC2CCC2)cc1] | C28H35N3O2 | 445.61 | 446 |
| 125 | 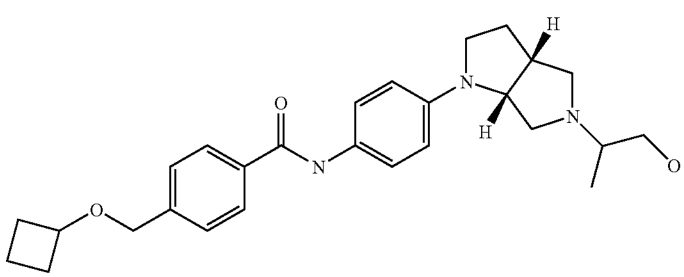 [SMILES: CC(CO)N1C[C@H]2CCN(c3ccc(NC(=O)c4ccc(COC5CCC5)cc4)cc3)[C@H]2C1] | C27H35N3O3 | 449.60 | 450 |
| 126 | 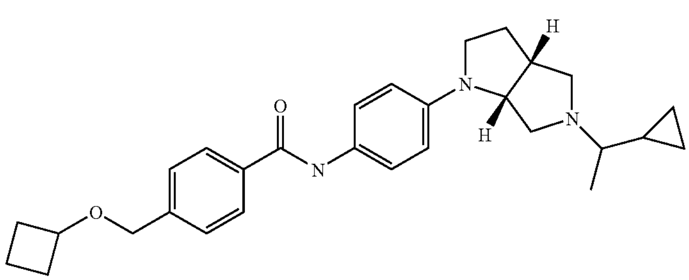 [SMILES: CC(C1CC1)N1C[C@H]2CCN(c3ccc(NC(=O)c4ccc(COC5CCC5)cc4)cc3)[C@H]2C1] | C29H37N3O2 | 459.64 | 460 |

TABLE 4-continued

| Ex. No. | Structure | Molecular formula | Molecular weight | ESI-MS [M + H]+ |
|---|---|---|---|---|
| 127 | 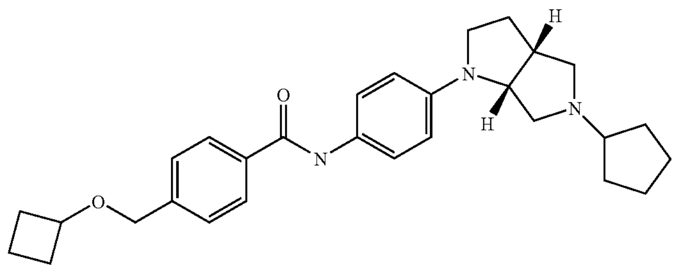 [SMILES: O=C(Nc1ccc(N2CC[C@@H]3CN(C4CCCC4)C[C@@H]32)cc1)c1ccc(COC2CCC2)cc1] | C29H37N3O2 | 459.64 | 460 |
| 128 | 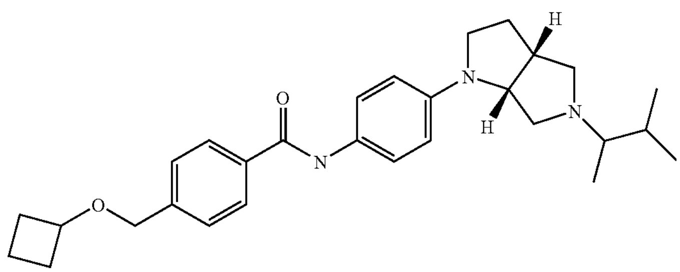 [SMILES: CC(C)C(C)N1C[C@H]2CCN(c3ccc(NC(=O)c4ccc(COC5CCC5)cc4)cc3)[C@H]2C1] | C29H39N3O2 | 461.65 | 462 |
| 129 | 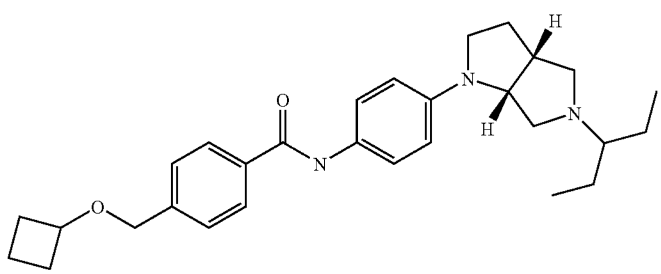 [SMILES: CCC(CC)N1C[C@H]2CCN(c3ccc(NC(=O)c4ccc(COC5CCC5)cc4)cc3)[C@H]2C1] | C29H39N3O2 | 461.65 | 462 |
| 130 | 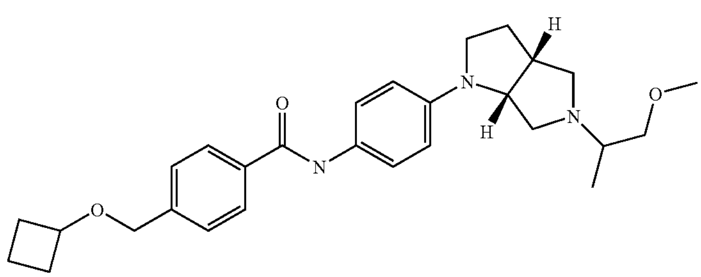 [SMILES: COCC(C)N1C[C@H]2CCN(c3ccc(NC(=O)c4ccc(COC5CCC5)cc4)cc3)[C@H]2C1] | C28H37N3O3 | 463.63 | 464 |
| 131 | 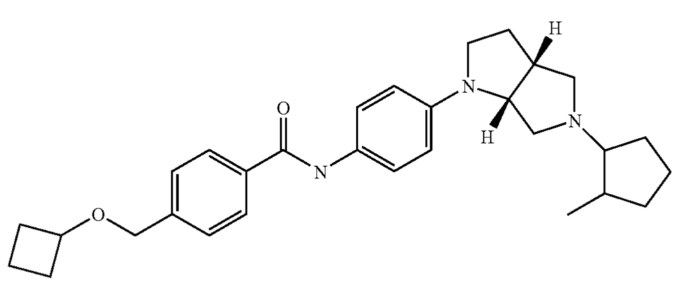 [SMILES: CC1CCCC1N1C[C@H]2CCN(c3ccc(NC(=O)c4ccc(COC5CCC5)cc4)cc3)[C@H]2C1] | C30H39N3O2 | 473.66 | 474 |

TABLE 4-continued

| Ex. No. | Structure | Molecular formula | Molecular weight | ESI-MS [M + H]+ |
|---|---|---|---|---|
| 132 | 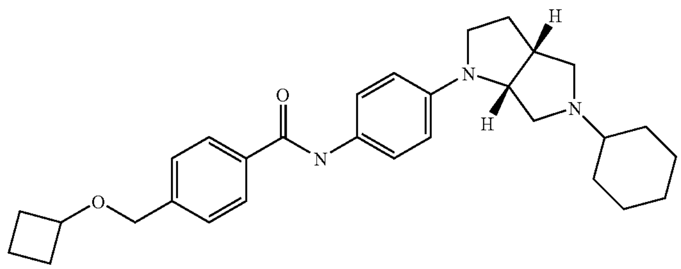 [SMILES: O=C(Nc1ccc(N2CC[C@@H]3CN(C4CCCCC4)C[C@@H]32)cc1)c1ccc(COC2CCC2)cc1] | C30H39N3O2 | 473.66 | 474 |
| 133 | 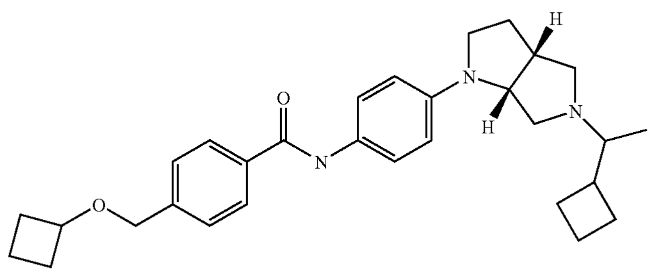 [SMILES: CC(C1CCC1)N1C[C@H]2CCN(c3ccc(NC(=O)c4ccc(COC5CCC5)cc4)cc3)[C@H]2C1] | C30H39N3O2 | 473.66 | 474 |
| 134 | 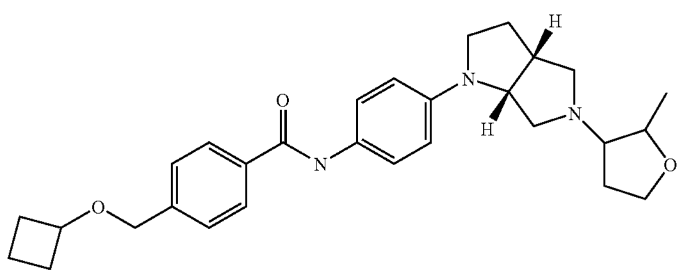 [SMILES: CC1OCCC1N1C[C@H]2CCN(c3ccc(NC(=O)c4ccc(COC5CCC5)cc4)cc3)[C@H]2C1] | C29H37N3O3 | 475.64 | 476 |
| 135 | 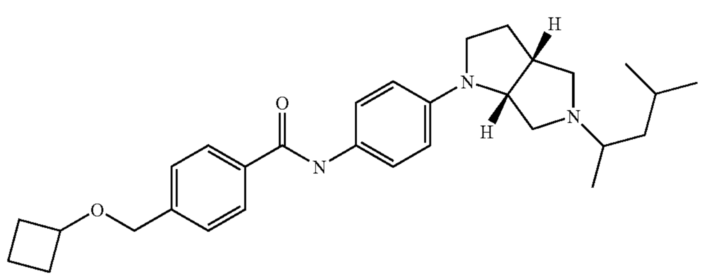 [SMILES: CC(C)CC(C)N1C[C@H]2CCN(c3ccc(NC(=O)c4ccc(COC5CCC5)cc4)cc3)[C@H]2C1] | C30H41N3O2 | 475.68 | 476 |
| 136 | 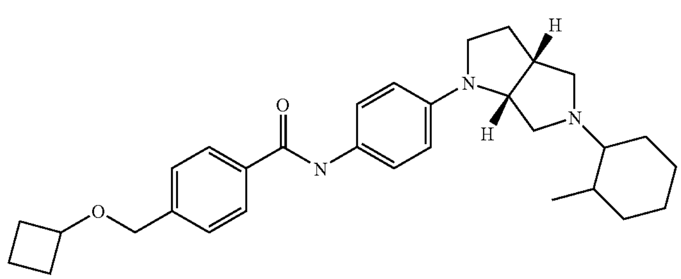 [SMILES: CC1CCCCC1N1C[C@H]2CCN(c3ccc(NC(=O)c4ccc(COC5CCC5)cc4)cc3)[C@H]2C1] | C31H41N3O2 | 487.69 | 488 |

TABLE 4-continued
| Ex. No. | Structure | Molecular formula | Molecular weight | ESI-MS [M + H]+ |
|---|---|---|---|---|
| 137 | 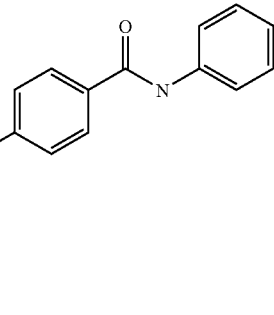 | C31H41N3O2 | 487.69 | 488 |
| 138 | 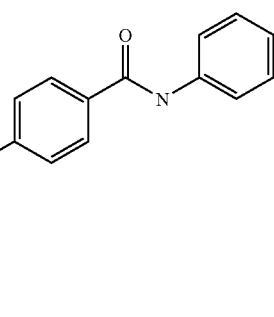 | C30H40N4O2 | 488.68 | 489 |
| 139 | 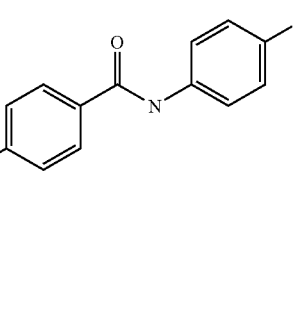 | C29H38N4O3 | 490.65 | 491 |
| 140 | 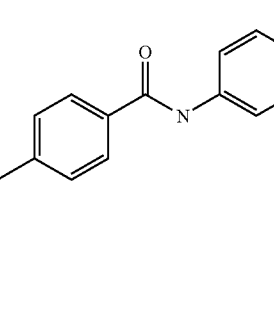 | C30H41N3O3 | 491.68 | 492 |
| 141 | 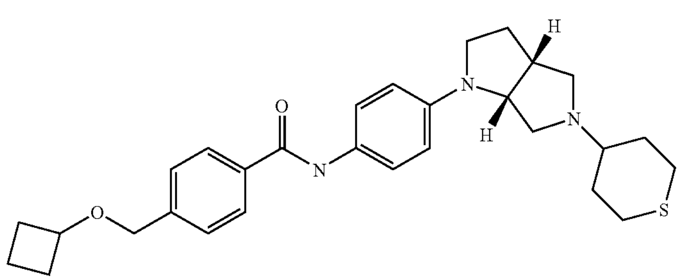 [SMILES: O=C(Nc1ccc(N2CC[C@@H]3CN(C4CCSCC4)C[C@@H]32)cc1)c1ccc(COC2CCC2)cc1] | C29H37N3O2S | 491.70 | 492 |

TABLE 4-continued
| Ex. No. | Structure | Molecular formula | Molecular weight | ESI-MS [M + H]+ |
|---|---|---|---|---|
| 142 | 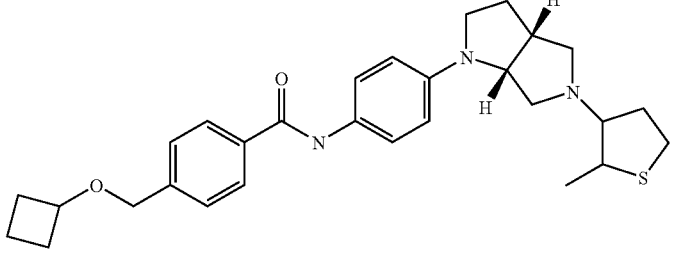 | C29H37N3O2S | 491.70 | 492 |
| 143 | 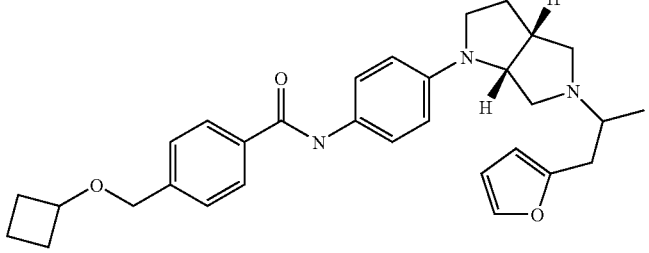 | C31H37N3O3 | 499.66 | 500 |
| 144 | 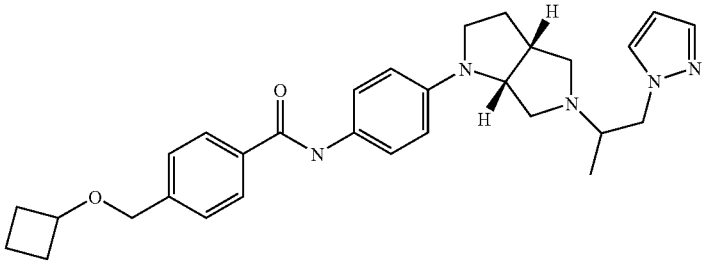 [SMILES: CC(Cn1cccn1)N1C[C@H]2CCN(c3ccc(NC(=O)c4ccc(COC5CCC5)cc4)cc3)[C@H]2C1] | C30H37N5O2 | 499.66 | 500 |
| 145 | 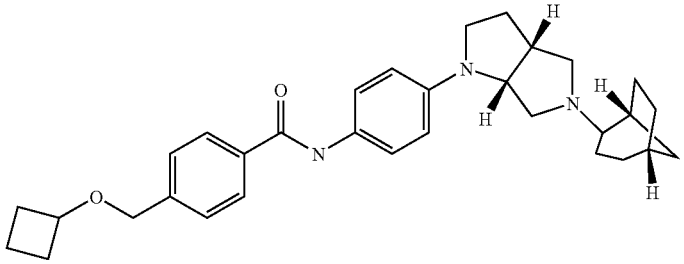 [SMILES: O=C(Nc1ccc(N2CC[C@@H]3CN(C4CC[C@@H]5CC[C@@H]4C5)C[C@@H]32)cc1)c1ccc(COC2CCC2)cc1] | C32H41N3O2 | 499.70 | 500 |
| 146 | 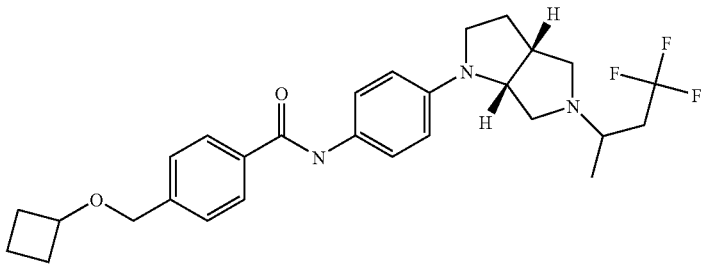 [SMILES: CC(CC(F)(F)F)N1C[C@H]2CCN(c3ccc(NC(=O)c4ccc(COC5CCC5)cc4)cc3)[C@H]2C1] | C28H34F3N3O2 | 501.60 | 502 |

TABLE 4-continued

| Ex. No. | Structure | Molecular formula | Molecular weight | ESI-MS [M + H]+ |
|---|---|---|---|---|
| 147 | 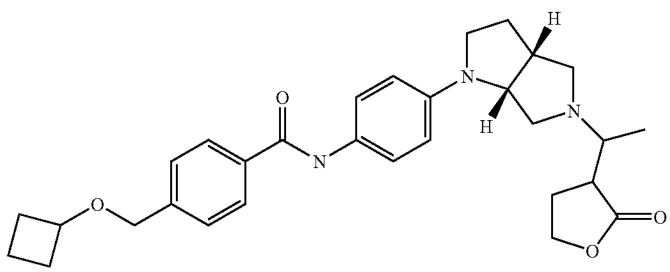 [SMILES: CC(C1CCOC1=O)N1C[C@H]2CCN(c3ccc(NC(=O)c4ccc(COC5CCC5)cc4)cc3)[C@H]2C1] | C30H37N3O4 | 503.65 | 504 |
| 148 | 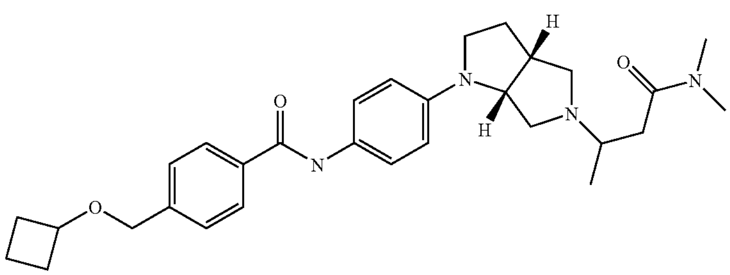 [SMILES: CC(CC(=O)N(C)C)N1C[C@H]2CCN(c3ccc(NC(=O)c4ccc(COC5CCC5)cc4)cc3)[C@H]2C1] | C30H40N4O3 | 504.68 | 505 |
| 149 | 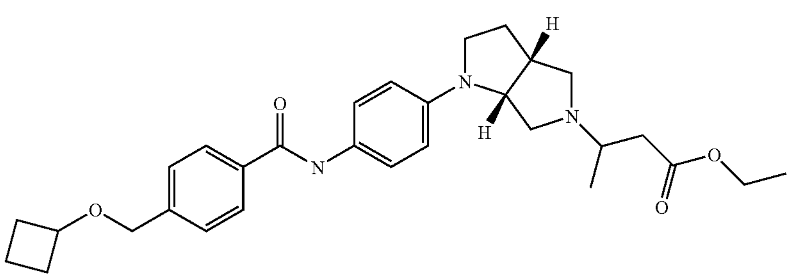 [SMILES: CCOC(=O)CC(C)N1C[C@H]2CCN(c3ccc(NC(=O)c4ccc(COC5CCC5)cc4)cc3)[C@H]2C1] | C30H39N3O4 | 505.66 | 506 |
| 150 | 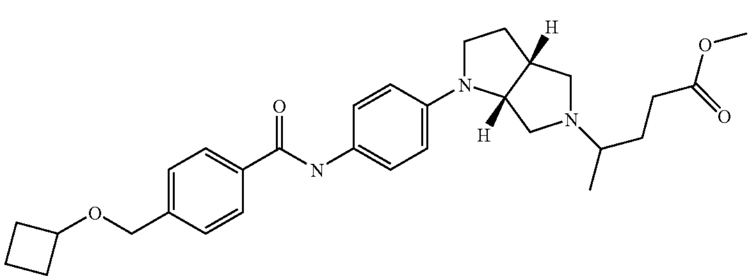 [SMILES: COC(=O)CCC(C)N1C[C@H]2CCN(c3ccc(NC(=O)c4ccc(COC5CCC5)cc4)cc3)[C@H]2C1] | C30H39N3O4 | 505.66 | 506 |
| 151 | 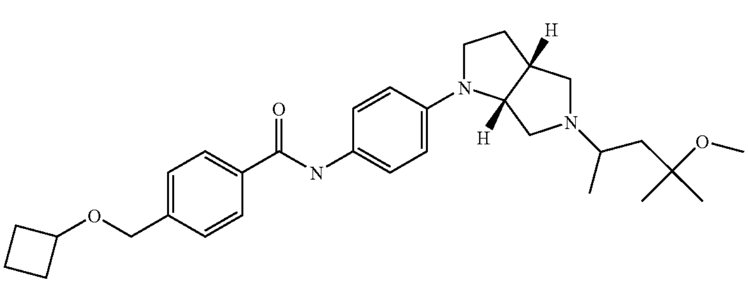 [SMILES: COC(C)(C)CC(C)N1C[C@H]2CCN(c3ccc(NC(=O)c4ccc(COC5CCC5)cc4)cc3)[C@H]2C1] | C31H43N3O3 | 505.71 | 506 |

TABLE 4-continued

| Ex. No. | Structure | Molecular formula | Molecular weight | ESI-MS [M + H]+ |
|---|---|---|---|---|
| 152 | 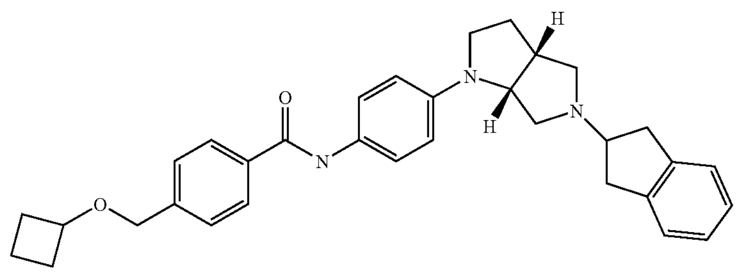 [SMILES: O=C(Nc1ccc(N2CC[C@@H]3CN(C4Cc5ccccc5C4)C[C@@H]32)cc1)c1ccc(COC2CCC2)cc1] | C33H37N3O2 | 507.68 | 508 |
| 153 | 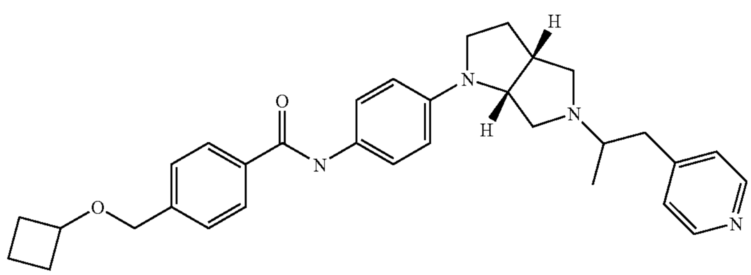 [SMILES: CC(Cc1ccncc1)N1C[C@H]2CCN(c3ccc(NC(=O)c4ccc(COC5CCC5)cc4)cc3)[C@H]2C1] | C32H38N4O2 | 510.69 | 511 |
| 154 | 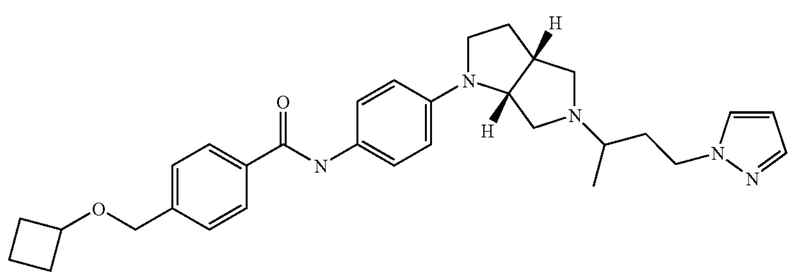 [SMILES: CC(CCn1cccn1)N1C[C@H]2CCN(c3ccc(NC(=O)c4ccc(COC5CCC5)cc4)cc3)[C@H]2C1] | C31H39N5O2 | 513.69 | 514 |
| 155 | 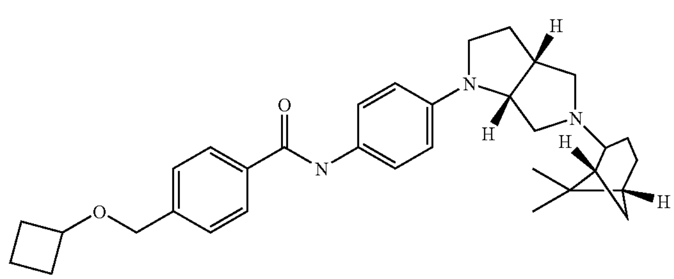 [SMILES: CC1(C)[C@@H]2CCC(N3C[C@H]4CCN(c5ccc(NC(=O)c6ccc(COC7CCC7)cc6)cc5)[C@H]4C3)[C@@H]1C2] | C33H43N3O2 | 513.73 | 514 |
| 156 | 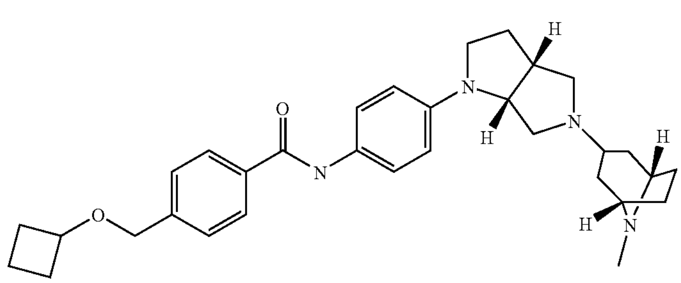 [SMILES: CN1[C@H]2CC[C@H]1CC(N1C[C@H]3CCN(c4ccc(NC(=O)c5ccc(COC6CCC6)cc5)cc4)[C@H]3C1)C2] | C32H42N4O2 | 514.72 | 515 |

TABLE 4-continued

| Ex. No. | Structure | Molecular formula | Molecular weight | ESI-MS [M + H]+ |
|---|---|---|---|---|
| 157 | 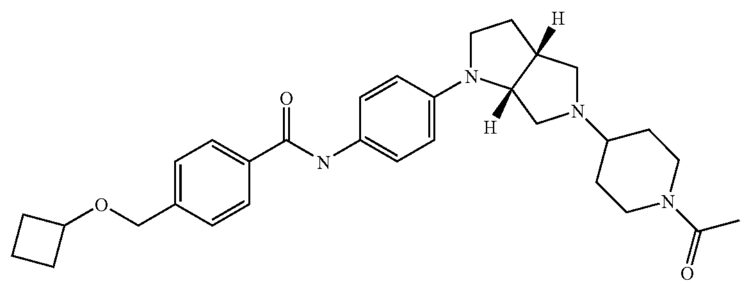 [SMILES: CC(=O)N1CCC(N2C[C@H]3CCN(c4ccc(NC(=O)c5ccc(COC6CCC6)cc5)cc4)[C@H]3C2)CC1] | C31H40N4O3 | 516.69 | 517 |
| 158 | 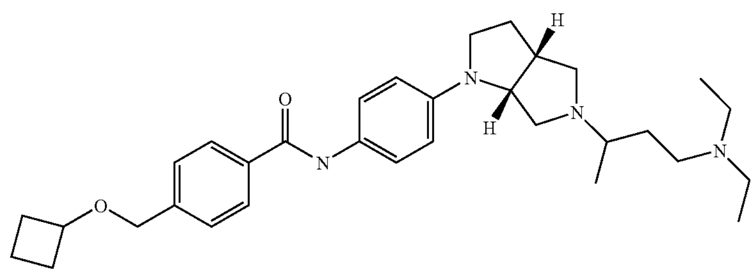 [SMILES: CCN(CC)CCC(C)N1C[C@H]2CCN(c3ccc(NC(=O)c4ccc(COC5CCC5)cc4)cc3)[C@H]2C1] | C32H46N4O2 | 518.75 | 519 |
| 159 | 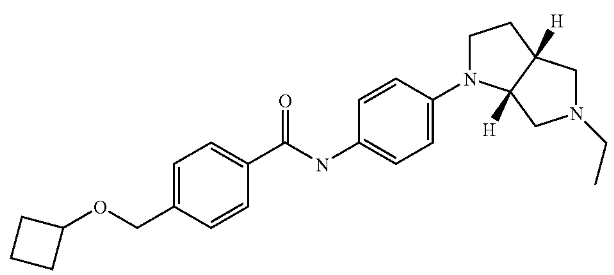 [SMILES: CCN1C[C@H]2CCN(c3ccc(NC(=O)c4ccc(COC5CCC5)cc4)cc3)[C@H]2C1] | C26H33N3O2 | 419.57 | 420 |
| 160 | 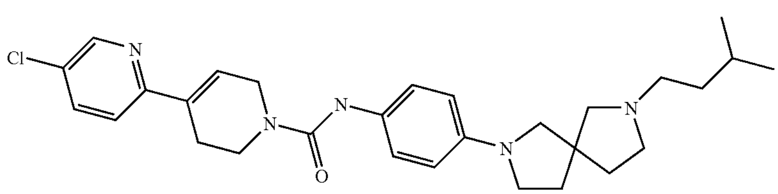 [SMILES: CC(C)CCN1CCC2(CCN(c3ccc(NC(=O)N4CC=C(c5ccc(Cl)cn5)CC4)cc3)C2)C1] | C29H38ClN5O | 508.11 | 509 |
| 161 | 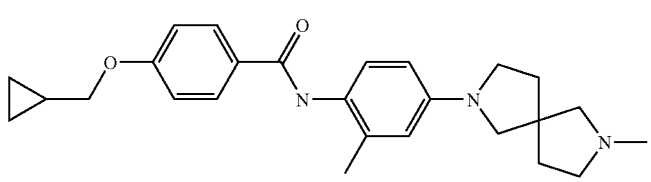 [SMILES: Cc1cc(N2CCC3(CCN(C)C3)C2)ccc1NC(=O)c1ccc(OCC2CC2)cc1] | C26H33N3O2 | 419.57 | 420 |
| 162 | 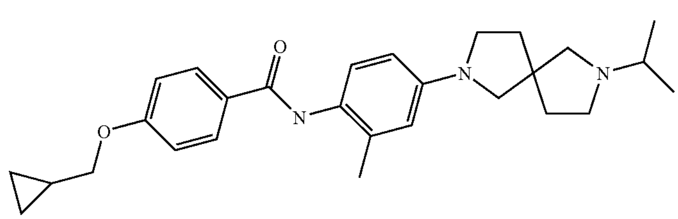 [SMILES: Cc1cc(N2CCC3(CCN(C(C)C)C3)C2)ccc1NC(=O)c1ccc(OCC2CC2)cc1] | C28H37N3O2 | 447.63 | 448 |

TABLE 4-continued
| Ex. No. | Structure | Molecular formula | Molecular weight | ESI-MS [M + H]+ |
|---|---|---|---|---|
| 163 | 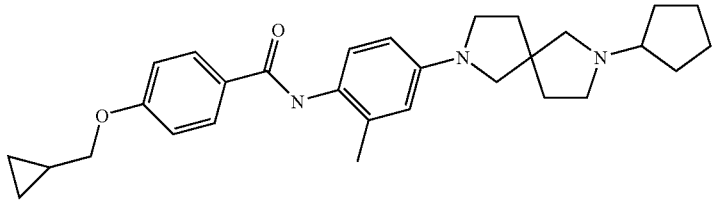 [SMILES: Cc1cc(N2CCC3(CCN(C4CCCC4)C3)C2)ccc1NC(=O)c1ccc(OCC2CC2)cc1] | C30H39N3O2 | 473.66 | 474 |
| 164 | 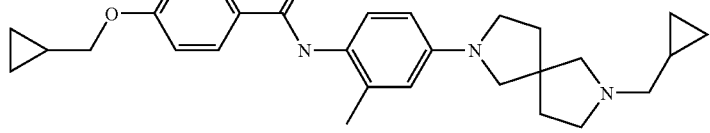 | C29H37N3O2 | 459.64 | 460 |
| 165 | 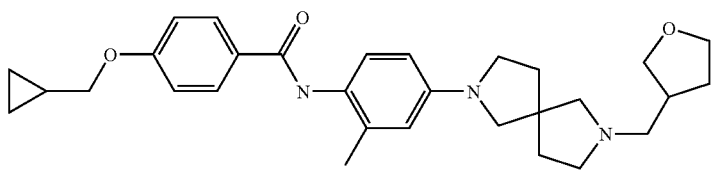 [SMILES: Cc1cc(N2CCC3(CCN(CC4CCOC4)C3)C2)ccc1NC(=O)c1ccc(OCC2CC2)cc1] | C30H39N3O3 | 489.66 | 490 |
| 166 | 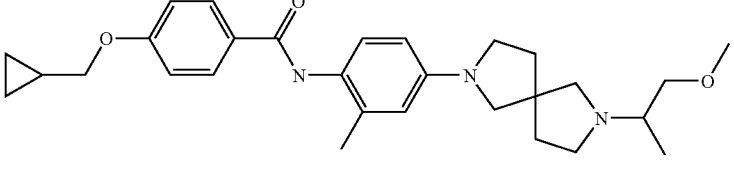 | C29H39N3O3 | 477.65 | 478 |
| 167 | 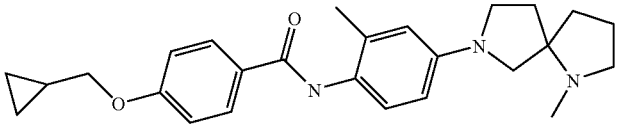 [SMILES: Cc1cc(N2CCC3(CCCN3C)C2)ccc1NC(=O)c1ccc(OCC2CC2)cc1] | C26H33N3O2 | 419.57 | 420 |
| 168 | 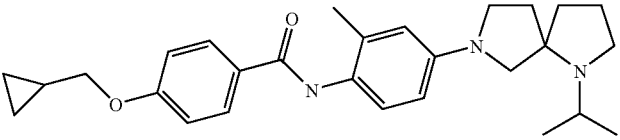 [SMILES: Cc1cc(N2CCC3(CCCN3C(C)C)C2)ccc1NC(=O)c1ccc(OCC2CC2)cc1] | C28H37N3O2 | 447.63 | 448 |
| 169 | 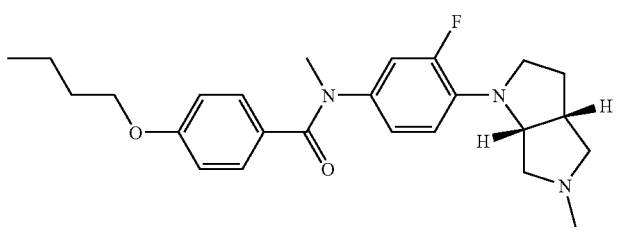 [SMILES: CCCCOc1ccc(C(=O)N(C)c2ccc(N3CC[C@@H]4CN(C)C[C@@H]43)c(F)c2)cc1] | C25H32FN3O2 | 425.55 | 426 |
| 170 | 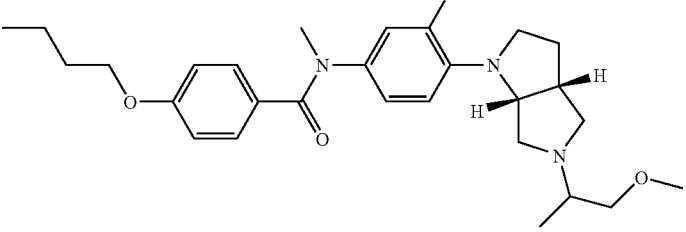 | C28H38FN3O3 | 483.63 | 484 |

TABLE 4-continued

| Ex. No. | Structure | Molecular formula | Molecular weight | ESI-MS [M + H]+ |
|---|---|---|---|---|
| 171 | 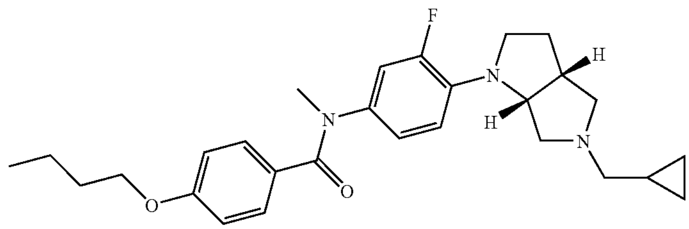 [SMILES: CCCCOc1ccc(C(=O)N(C)c2ccc(N3CC[C@@H]4CN(CC5CC5)C[C@@H]43)c(F)c2)cc1] | C28H36FN3O2 | 465.62 | 466 |
| 172 | 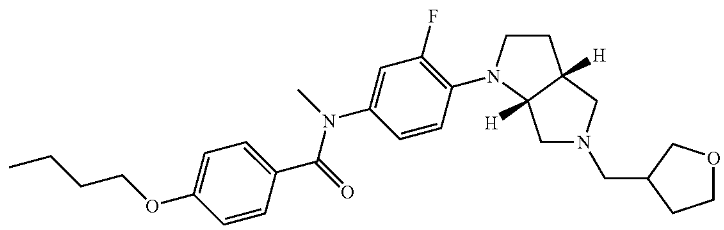 [SMILES: CCCCOc1ccc(C(=O)N(C)c2ccc(N3CC[C@@H]4CN(CC5CCOC5)C[C@@H]43)c(F)c2)cc1] | C29H38FN3O3 | 495.64 | 496 |
| 173 | 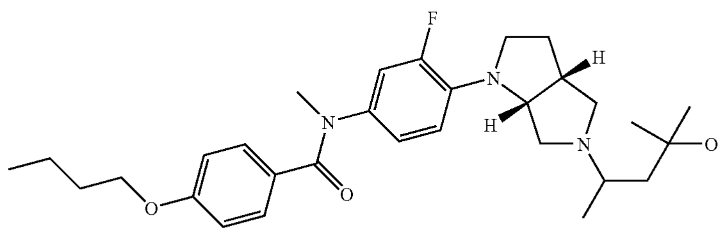 [SMILES: CCCCOc1ccc(C(=O)N(C)c2ccc(N3CC[C@@H]4CN(C(C)CC(C)(C)O)C[C@@H]43)c(F)c2)cc1] | C30H42FN3O3 | 511.69 | 512 |
| 174 | 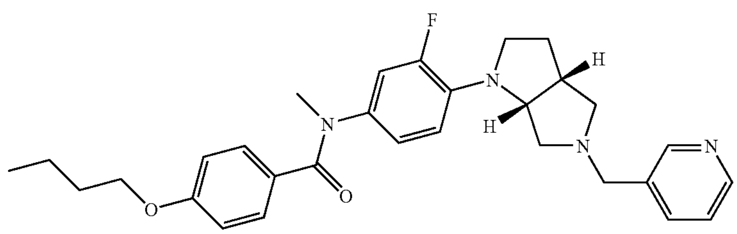 [SMILES: CCCCOc1ccc(C(=O)N(C)c2ccc(N3CC[C@@H]4CN(Cc5cccnc5)C[C@@H]43)c(F)c2)cc1] | C30H35FN4O2 | 502.64 | 503 |
| 175 | 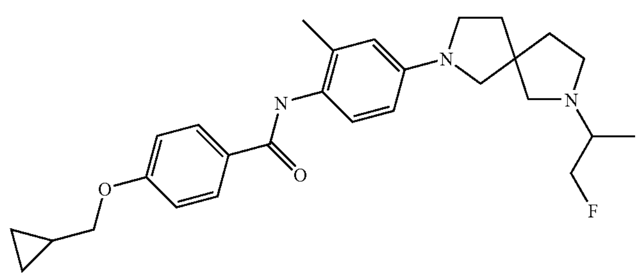 [SMILES: Cc1cc(N2CCC3(CCN(C(C)CF)C3)C2)ccc1NC(=O)c1ccc(OCC2CC2)cc1] | C28H36FN3O2 | 465.62 | 466 |
| 176 | 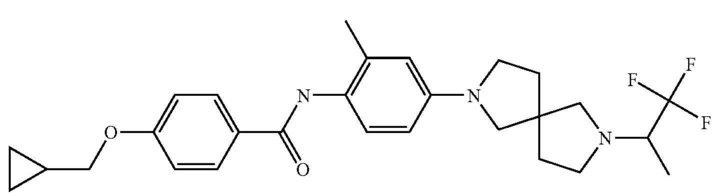 [SMILES: Cc1cc(N2CCC3(CCN(C(C)C(F)(F)F)C3)C2)ccc1NC(=O)c1ccc(OCC2CC2)cc1] | C28H34F3N3O2 | 501.60 | 502 |

TABLE 4-continued

| Ex. No. | Structure | Molecular formula | Molecular weight | ESI-MS [M + H]+ |
|---|---|---|---|---|
| 177 | 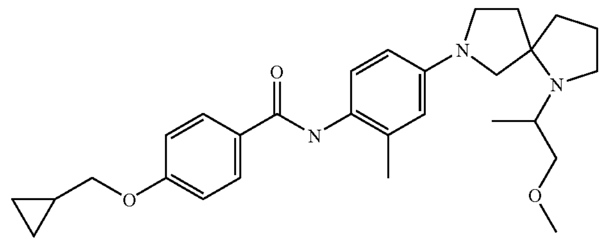 [SMILES: COCC(C)N1CCCC12CCN(c1ccc(NC(=O)c3ccc(OCC4CC4)cc3)c(C)c1)C2] | C29H39N3O3 | 477.65 | 478 |
| 178 | 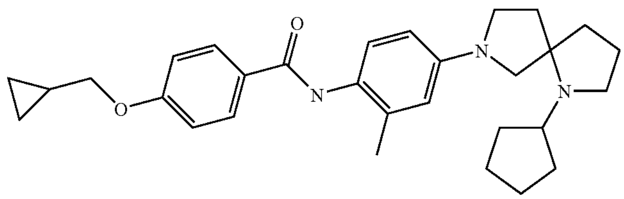 [SMILES: Cc1cc(N2CCC3(CCCN3C3CCCC3)C2)ccc1NC(=O)c1ccc(OCC2CC2)cc1] | C30H39N3O2 | 473.66 | 474 |
| 179 | 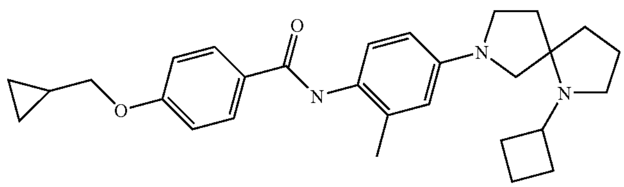 [SMILES: Cc1cc(N2CCC3(CCCN3C3CCC3)C2)ccc1NC(=O)c1ccc(OCC2CC2)cc1] | C29H37N3O2 | 459.64 | 460 |
| 180 | 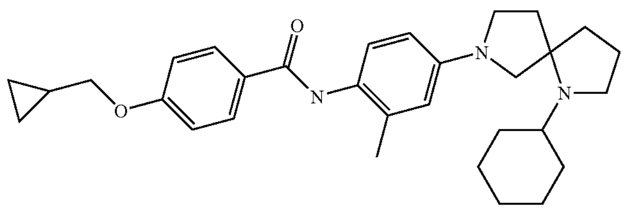 [SMILES: Cc1cc(N2CCC3(CCCN3C3CCCCC3)C2)ccc1NC(=O)c1ccc(OCC2CC2)cc1] | C31H41N3O2 | 487.69 | 488 |
| 181 | 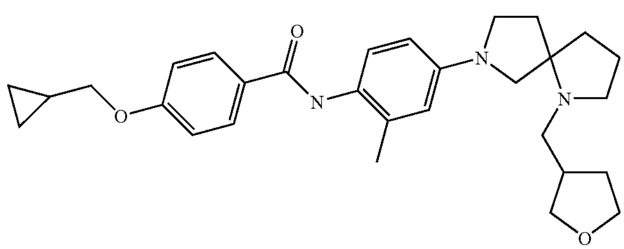 [SMILES: Cc1cc(N2CCC3(CCCN3CC3CCOC3)C2)ccc1NC(=O)c1ccc(OCC2CC2)cc1] | C30H39N3O3 | 489.66 | 490 |
| 182 | 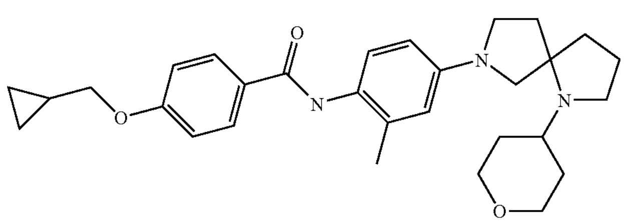 [SMILES: Cc1cc(N2CCC3(CCCN3C3CCOCC3)C2)ccc1NC(=O)c1ccc(OCC2CC2)cc1] | C30H39N3O3 | 489.66 | 490 |
| 183 | 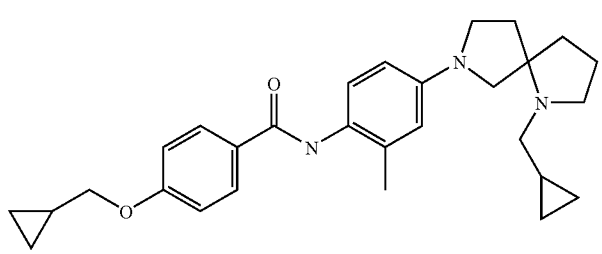 [SMILES: Cc1cc(N2CCC3(CCCN3CC3CC3)C2)ccc1NC(=O)c1ccc(OCC2CC2)cc1] | C29H37N3O2 | 459.64 | 460 |

TABLE 4-continued

| Ex. No. | Structure | Molecular formula | Molecular weight | ESI-MS [M + H]+ |
|---|---|---|---|---|
| 184 | 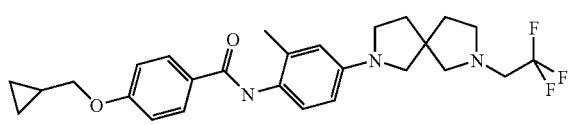 [SMILES: Cc1cc(N2CCC3(CCN(CC(F)(F)F)C3)C2)ccc1NC(=O)c1ccc(OCC2CC2)cc1] | C31H42N4O3 | 518.71 | 519 |

Example 185

4-Cyclopropylmethoxy-N-{2-methyl-4-[7-(2,2,2-trifluoroethyl)-2,7-diaza-spiro[4.4]non-2-yl]phenyl}benzamide

Method H

A mixture of 4-cyclopropylmethoxy-N-[4-(2,7-diazaspiro[4.4]non-2-yl)-2-methylphenyl]benzamide (hydrochloride; 50 mg), 1,1,1-trifluoro-2-iodo-ethane (24 mg), triethylamine (12 mg) and DMF (2 ml) was heated at 50° C. for 12 hours. The cooled reaction mixture was purified directly by preparative HPLC. The product with the molecular weight of 487.57 (C27H32F3N3O2); MS (ESI): 488 (M+H+) was obtained in this way.

The examples compiled in table 5 were obtained by method H by heating (reaction temperatures of 25-100° C.) 4-cyclopropylmethoxy-N-[4-(2,7-di-azaspiro[4.4]non-2-yl)-2-methylphenyl]benzamide with alkyl bromides, iodides or epoxides as alkylating agents.

TABLE 5

| Ex No. | Structure | Molecular formula | Molecular weight | ESI-MS [M + H]+ |
|---|---|---|---|---|
| 186 | 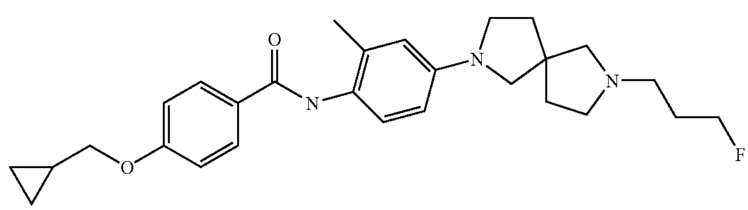 [SMILES: Cc1cc(N2CCC3(CCN(CCCF)C3)C2)ccc1NC(=O)c1ccc(OCC2CC2)cc1] | C28H36FN3O2 | 465.62 | 466 |
| 187 | 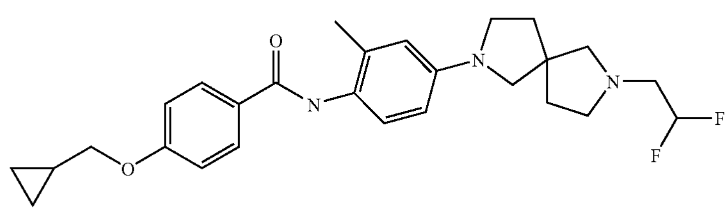 [SMILES: Cc1cc(N2CCC3(CCN(CC(F)F)C3)C2)ccc1NC(=O)c1ccc(OCC2CC2)cc1] | C27H33F2N3O2 | 469.58 | 470 |
| 188 | 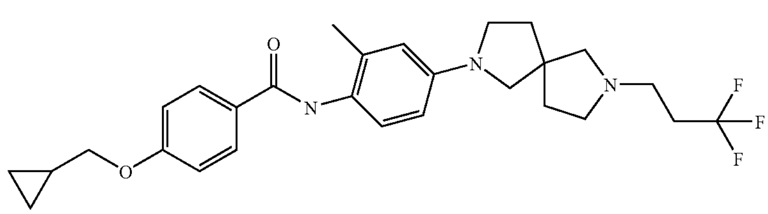 [SMILES: Cc1cc(N2CCC3(CCN(CCC(F)(F)F)C3)C2)ccc1NC(=O)c1ccc(OCC2CC2)cc1] | C28H34F3N3O2 | 501.60 | 502 |

TABLE 5-continued

| Ex No. | Structure | Molecular formula | Molecular weight | ESI-MS [M + H]+ |
|---|---|---|---|---|
| 189 | 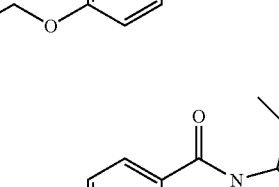 | C28H37N3O3 | 463.63 | 464 |
| 190 | 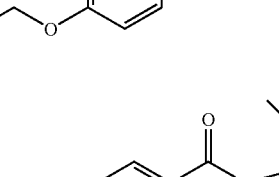 | C28H35N3O4 | 477.61 | 478 |
| 191 | 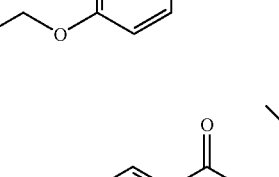 | C27H34FN3O2 | 451.59 | 452 |
| 192 | 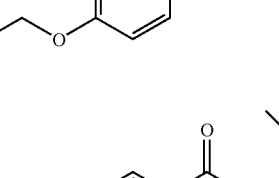 | C28H35N3O3 | 461.61 | 462 |
| 193 | 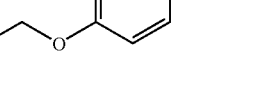 | C29H39N3O3 | 477.65 | 478 |

Example 194

N-[4-(5-Acetylhexahydropyrrolo[3,4-b]pyrrol-1-yl)phenyl]-4-cyclobutoxy-methylbenzamide

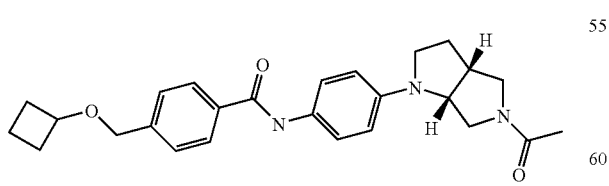

A mixture of 4-cyclobutoxymethyl-N-[4-(hexahydropyrrolo[3,4-b]pyrrol-1-yl)-phenyl]benzamide (30 mg), N,N-diisopropylethylamine (10 mg) and dichloromethane (2 ml) was mixed with acetyl chloride (6.1 mg). After 30 minutes, the reaction solution was concentrated and the residue was purified by preparative HPLC. The product with the molecular weight of 433.56 (C26H31N3O3); MS (ESI): 434 (M+H+) was obtained in this way.

Example 195

4-Cyclobutoxymethyl-N-{4-[5-(2-dimethylaminoacetyl)hexahydropyrrolo-[3,4-b]pyrrol-1-yl]phenyl}benzamide

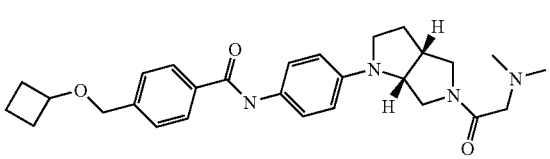 [SMILES: CN(C)CC(=O)N1C[C@H]2CCN(c3ccc(NC(=O)c4ccc(COC5CCC5)cc4)cc3)[C@H]2C1]

4-Cyclobutoxymethyl-N-[4-(hexahydropyrrolo[3,4-b]pyrrol-1-yl)phenyl]-benzamide was reacted with N,N-dimethylglycine by method E. The product with the molecular weight of 476.62 (C28H36N4O3); MS (ESI): 477 (M+H+) was obtained in this way.

Synthesis of Starting Materials which Cannot be Purchased 4-(Cyclopentanecarbonylamino)benzoic acid 4-Aminobenzoic acid ethyl ester was reacted with cyclopentanecarboxylic acid by method E, and the resulting ester was hydrolyzed by boiling with sodium hydroxide in aqueous ethanol. The product with the molecular weight of 233.27 (C13H15NO3); MS (ESI): 234 (M+H+) was obtained in this way.

4-Cyclobutoxymethylbenzoic acid

Sodium hydride (50% in oil; 0.42 g) was cautiously added to a solution of cyclobutanol (0.7 g) in DMF (8 ml). After gas evolution ceased, 4-bromomethylbenzoic acid methyl ester (1.0 g) was added. After 4 hours, the mixture was cautiously hydrolyzed and then partitioned between water and ethyl acetate. The organic phase was dried over magnesium sulfate and concentrated. The ester obtained as crude product was hydrolyzed by boiling with sodium hydroxide in aqueous ethanol. The product with the molecular weight of 206.24 (C12H14O3); MS (ESI): 207 (M+H+) was obtained in this way.

4-Cyclobutylmethoxybenzoic acid

4-Hydroxybenzoic acid ethyl ester was alkylated with cyclobutyl bromide by standard methods (DMF, Cs2CO3), and the resulting ester was hydrolyzed by boiling with sodium hydroxide in aqueous ethanol. The product with the molecular weight of 206.24 (C12H14O3); MS (ESI): 207 (M+H+) was obtained in this way.

The following acids were obtained analogously:
4-(tetrahydrofuran-2-ylmethoxy)benzoic acid
4-(2-methoxyethoxy)benzoic acid
4-(3-methoxypropoxy)benzoic acid
4-(tetrahydropyran-2-ylmethoxy)benzoic acid
4-cyclopropylmethoxybenzoic acid
4-(Pyridin-2-yloxymethyl)benzoic acid A mixture of 2-fluoropyridine (1.6 g), 4-bromobenzyl alcohol (3.08 g), potassium tert-butoxide (2.03 g) and N-methylpyrrolidone (12.8 ml) was heated at 100° C. by microwave irradiation for one minute. The mixture was diluted with water and extracted with ethyl acetate. The organic phase was dried over magnesium sulfate, filtered and concentrated. 2-(4-Bromobenzyloxy)pyridine was obtained in this way.

n-Butyllithium (1.6 M in hexane, 11.4 ml) was added to a solution of 2-(4-bromobenzyloxy)pyridine (4.2 g) in THF (120 ml) at −78° C. After 15 minutes, dry ice (7 g) was added. After warming to room temperature, the mixture was diluted with water and extracted with ethyl acetate. The aqueous phase was acidified and again extracted with ethyl acetate. The organic phase was dried over magnesium sulfate, filtered and concentrated. The product with the molecular weight of 229.24 (C13H11NO3); MS (ESI): 230 (M+H+) was obtained in this way.

5-Butoxypyridine-2-carboxylic acid

Sodium hydride (50% in oil, 250 mg) was added to 5-hydroxypyridine-2-carboxylic acid benzhydryl ester (2.0 g) dissolved in DMF (20 ml) and, after gas evolution ceased, 1-bromobutane (0.72 g) was added. The mixture was heated at 90° C. for 6 hours. It was diluted with water and extracted with ethyl acetate. The organic phase was dried over magnesium sulfate and concentrated. The residue was hydrogenated in analogy to method B. The product with the molecular weight of 195.22 (C10H13NO3); MS (ESI): 196 (M+H+) was obtained in this way.

5-Chloro-1',2',3',6'-tetrahydro[2,4']bipyridinyl

Butyllithium (15% in hexane; 7.6 ml) was added dropwise to a solution of 2-bromo-5-chloropyridine (2.0 g) in diethyl ether (50 ml) at −78° C. and, after one hour, a solution of N-tert-butoxycarbonyl-4-piperidinone (2.1 g) in diethyl ether (10 ml) was added dropwise. After 30 minutes, water was cautiously added, and the mixture was extracted with ethyl acetate. The organic phase was dried over sodium sulfate, filtered and concentrated. The residue was treated with thionyl chloride (3 g) for 24 hours, and the concentrated reaction solution was purified by preparative HPLC. The product with the molecular weight of 194.67 (C10H11ClN2); MS (ESI): 195 (M+H+) was obtained in this way.

5-Chloro-1',2',3',4',5',6'-hexahydro[2,4']bipyridinyl

Platinum dioxide (58 mg) was added to a mixture of 5-chloro-1',2',3',6'-tetrahydro[2,4']bipyridinyl (500 mg) and ethyl acetate (50 ml) under argon. The atmosphere was replaced by hydrogen and the mixture was vigorously stirred for 3 hours. The catalyst was filtered off with suction and the filtrate was concentrated. The product with the molecular weight of 196.68 (C10H13ClN2); MS (ESI): 197 (M+H+) was obtained in this way.

4-(5-Chloropyridin-2-yl)cyclohex-3-enecarboxylic acid

A mixture of 4-(5-chloropyridin-2-yl)-4-hydroxycyclohexanecarboxylic acid ethyl ester (1.6 g) and sulfuric acid (5 ml) is heated at 60° C. for 15 minutes. After addition of water (0.4 ml) the mixture is again heated at 60° C. for 20 minutes. The cooled reaction mixture was diluted with water and washed with dichloromethane. The aqueous phase was adjusted to pH 7 with sodium bicarbonate solution and extracted with dichloromethane. The organic phase was dried over sodium sulfate and concentrated. The product with the molecular weight of 237.69 (C12H12ClNO2); MS (ESI): 238 (M+H+) was obtained in this way.

4-(5-Chloropyridin-2-yl)-4-hydroxycyclohexanecarboxylic acid ethyl ester

Butyllithium (15% in hexane; 15 ml) was added dropwise to a solution of 2-bromo-5-chloropyridine (3.8 g) in diethyl ether (80 ml) at −78° C. and, after one hour, a solution of 4-oxocyclohexanecarboxylic acid ethyl ester (3.7 g) in diethyl ether (10 ml) was added dropwise. After 30 minutes, water was cautiously added and the mixture was extracted with ethyl acetate. The organic phase was dried over sodium sulfate, filtered and concentrated. The residue was purified by preparative HPLC. The product with the molecular weight of 283.76 (C14H18ClNO3); MS (ESI): 284 (M+H+) was obtained in this way.

The following anilines were obtained by reacting the appropriate cyclic amine with the appropriate fluoronitrobenzene and subsequent hydrogenation by method C and method B:

2-Methyl-4-(5-methylhexahydropyrrolo[3,4-b]pyrrol-1-yl)phenylamine 1-(4-Aminophenyl)hexahydropyrrolo[3,4-b]pyrrole-5-carboxylic acid tert-butyl ester 1-(4-Amino-2-fluorophenyl)hexahydropyrrolo[3,4-b]pyrrole-5-carboxylic acid tert-butyl ester (The preparation of hexahydropyrrolo[3,4-b]pyrrole-5-carboxylic acid tert-butyl ester is described in WO2002070523.)

4-(1-Benzyl-1,7-diazaspiro[4.4]non-7-yl)-2-methylphenylamine (The benzyl protective group of this building block e.g. in example 88 can be eliminated by hydrogenation. The synthesis of 1-benzyl-1,7-diaza-spiro[4.4]nonane is described for example in J. Med. Chem. 1990, 33, 2270)

7-(4-Aminophenyl)-2,7-diazaspiro[4.4]nonane-2-carboxylic acid tert-butyl ester 7-(4-Amino-2-fluorophenyl)-2,7-diazaspiro[4.4]nonane-2-carboxylic acid tert-butyl ester 7-(4-Amino-3-methylphenyl)-2,7-diazaspiro[4.4]nonane-2-carboxylic acid tert-butyl ester

[2-(4-Aminophenyl)octahydrocyclopenta[c]pyrrol-4-yl]dimethylamine (Dimethyl(octahydrocyclopenta[c]pyrrol-4-yl)amine was prepared from 2-tritylhexahydrocyclopenta[c]pyrrol-4-one (Eur. J. Med. Chem. 1991, 26, 889) by reductive amination with dimethylamine (method G) and subsequent elimination of the trityl group by treatment with hydrochloric acid.)

The invention claimed is:

1. A compound of formula I

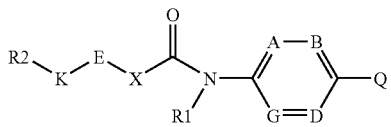

wherein:

A, B, D, and G are, independently of one another, N, or C(R3) or, alternatively, groups A and B or D and G are each C(R3) and together form an ortho-phenylene unit to result overall in a 1,4-disubstituted naphthalene system; wherein R3 is selected from H, F, Cl, Br, CF₃, CN, O—(C₁-C₆)-alkyl, O—(C₁-C₄)-alkoxy-(C₁-C₄)-alkyl, S—(C₁-C₆)-alkyl, (C₁-C₆)-alkyl, (C₀-C₈)-alkylene-aryl, O—(C₀-C₈)-alkylene-aryl, N(R4)(R5), SO₂—CH₃, CON(R6)(R7), N(R8)CO(R9), CO(R12), and (CR13R14)$_x$—O(R15); wherein R4, R5, R6, R7, R8 are, independently of one another, either H, or (C₁-C₈)-alkyl; or, R4 and R5, R6 and R7 form, independently of one another, and optionally together with the nitrogen atom to which they are bonded, a 5-6 membered ring which, apart from the nitrogen atom, may also include 1 further heteroatom selected from the group consisting of NH, N—(C₁-C₆)-alkyl, oxygen and sulfur;

R9, and R12 are, independently of one another, H or (C₁-C₈)-alkyl;

R13, R14 are each H;

R15 is H or (C₁-C₆)-alkyl;

x is 0, 1, or 2;

R1 is H or (C₁-C₈)-alkyl;

X is selected from N(R16), a bond, (R17)C=C(R18), C≡C, CH₂—CH₂, YCH₂, and CH₂Y;

Y is O, S, or N(R21);

R16, R17, and R18 are, independently of one another, H, or (C₁-C₈)-alkyl;

R21 is H, or (C₁-C₈)-alkyl;

E is a 3-8 membered bivalent carbo- or heterocyclic ring structure having 0-4 heteroatoms selected from the group consisting of N, O and S, and which may optionally have substituents selected from the group consisting of H, F, Cl, Br, OH, CF₃, NO₂, CN, OCF₃, O—(C₁-C₆)-alkyl, O—(C₁-C₄)-alkoxy-(C₁-C₄)-alkyl, S—(C₁-C₆)-alkyl, (C₁-C₆)-alkyl, (C₂-C₆)-alkenyl, O—(C₃-C₈)-cycloalkyl, (C₃-C₈)-cycloalkenyl, (C₂-C₆)-alkynyl, (C₀-C₈)-alkylene-aryl, O—(C₀-C₈)-alkylene-aryl, S-aryl, N(R22)(R23), SO₂—CH₃, N(R26)CO(R27), N(R28)SO₂(R29), and CO(R30) and may be mono- or bicyclic;

R22, R23, R26, and R28 are, independently of one another, H, or (C₁-C₈)-alkyl;

or, alternatively,

R22 and R23, independently of one another, optionally together with the nitrogen atom to which they are bonded, form a 5-6 membered ring which, apart from the nitrogen atom, may also include one further heteroatom selected from the group consisting of NH, N—(C₁-C₆)-alkyl, oxygen and sulfur;

R27, R29, and R30 are, independently of one another, H or (C₁-C₈)-alkyl;

K is selected from a bond, O, OCH₂, CH₂O, S, SO, SO₂, N(R35), N(R36)CO, CON(R37), (C(R38)(R39))$_v$, CO, (R31)C=C(R32), C≡C, SCH₂, and SO₂CH₂, wherein v is 2;

R31, R32, R35, R36, R37, R38, and R39 are, independently of one another, H or (C₁-C₈)-alkyl;

R2 is selected from (C₁-C₈)-alkyl, (C₁-C₄)-alkoxy-(C₁-C₄)-alkyl, a 3 to 10-membered mono-, bi-, tri- or spirocyclic ring which may include up to 3 heteroatoms selected from the group consisting of oxygen, nitrogen and sulfur, where the ring system may additionally be substituted by one or more of the following substituents: F, Cl, Br, CF₃, CN, (C₁-C₆)-alkyl, O—(C₁-C₈)-alkyl, (C₀-C₂)-alkylene-aryl, oxo, CO(R41), CON(R42)(R43), hydroxy, N(R45)CO(C₁-C₆)-alkyl, N(R46)(R47) and SO₂CH₃

R41, R42, R43, R45, R46, and R47 are, independently of one another, H or (C₁-C₈)-alkyl;

or, alternatively,

R42 and R43, R46 and R47 form, independently of one another, optionally together with the nitrogen atom to which they are bonded, a 5-6 membered ring which, apart from the nitrogen atom, may also include 1 further heteroatom selected from the group consisting of NH, N—(C₁-C₆)-alkyl, oxygen and sulfur;

Q is selected from:

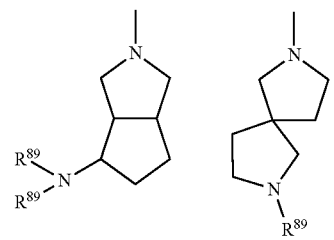

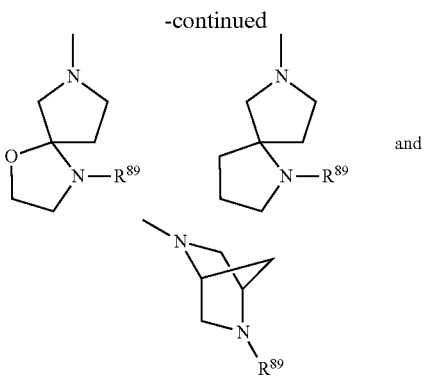

wherein:
R89 is selected from H, (C₁-C₄)-alkoxy-(C₁-C₄)-alkyl, (C₁-C₆)-alkyl, (C₂-C₆)-alkenyl, (C₂-C₆)-alkynyl, CO(R51), (CR52R53)$_o$-R54, and CO(CR52R53)$_p$-R55;
R51 is H or (C₁-C₈)-alkyl;
R52 and R53 are,
independently of one another, H, (C₁-C₈)-alkyl, OH, (C₃-C₈)-cycloalkyl, or (C₁-C₄)-alkoxy-(C₁-C₄)alkyl;
o and p are, independently of one another, 0, 1, 2, 3, 4, 5 or 6;
R54 and R55 are,
independently of one another, OH, O—(C₁-C₈)-alkyl, CON(R56)(R57), N(R58)CO(R59), N(R60)(R61), CO₂(R62), SO₂Me, CN, a 3-10 membered ring system having up to 3 heteroatoms selected from the group consisting of N, O and S, which may be substituted with one or more of the following substituents: F, Cl, Br, CF₃, (C₁-C₈-alkyl, O—(C₁-C₈)-alkyl, CO(R63), oxo, and OH;
R56, R57, R58, R59, R62, and R63 are,
independently of one another, H or (C₁-C₈)-alkyl;
or, alternatively,
R56 and R57
form, optionally together with the nitrogen atom to which they are bonded, a 5-6 membered ring which, apart from the nitrogen atom, may also include 1 further heteroatom selected from the group consisting of NH, N—(C₁-C₆)-alkyl, oxygen and sulfur;
R60 and R61 are,
independently of one another, H, (C₁-C₆)-alkyl, (C₁-C₄)-alkoxy-(C₁-C₄)-alkyl, (C₂-C₆)-alkenyl, (C₂-C₆)-alkynyl, CO(R64), (CR65R66)$_q$-R67, or CO(CR68R69)$_r$-R70; or, alternatively, R60 and R61 form, together with the nitrogen atom to which they are bonded, a 4 to 10-membered mono-, bi- or spirocyclic ring which, apart from the nitrogen atom, may comprise up to 3 additional heteroatoms selected from the group consisting of N, O and S and may, additionally, be substituted by one or more of the following substituents: F, Cl, Br, CF₃, O—(C₁-C₈)-alkyl, (C₁-C₆)-alkyl, CO(R71), oxo, OH, (C₁-C₄)-alkoxy-(C₁-C₄)-alkyl, hydroxy-(C₁-C₄)-alkyl, CON(R72)(R73), N(R74)CO(R75), N(R76)(R77), CO₂(R78), and SO₂Me; where
R64, R65, R66, R68, R69, R71, R72, R73, R74, R75, R76, R77, and R78 are,
independently of one another, H or (C₁-C₈)-alkyl;
or, alternatively,
R76 and R77 form, optionally together with the nitrogen atom to which they are bonded, a 5-6 membered ring which, apart from said nitrogen atom, may also include 1 further heteroatom selected from the group consisting of NH, N—(C₁-C₆)-alkyl, oxygen and sulfur;
q and r are, independently of one another, 0, 1, 2, 3, 4, 5 or 6;
R67 and R70 are,
independently of one another, OH, O—(C₁-C₈)-alkyl, CON(R79)(R80), N(R81)CO(R82), N(R83)(R84), CO₂(R85), SO₂Me, CN, a 3-10 membered ring system having 0 to 3 heteroatoms selected from the group consisting of N, O and S, which may be substituted with one or more of the following substituents: F, Cl, Br, CF₃, (C₁-C₈)-alkyl, O—(C₁-C₈)-alkyl, CO(R86), oxo, and OH;
R79, R80, R81, R82, R83, R84, R85, and R86 are,
independently of one another, H or (C₁-C₈)-alkyl;
or, alternatively,
R79 and R80, R83 and R84 form, independently of one another, optionally together with the nitrogen atom to which they are bonded, a 5-6 membered ring which, apart from the nitrogen atom, may also include 1 further heteroatom selected from the group consisting of NH, N—(C₁-C₈)-alkyl, oxygen and sulfur,
or
an N-oxide thereof or a physiologically tolerated salt thereof.

2. The compound as claimed in claim 1, wherein A, B, D, and G are, independently of one another, N or C(R3), and the total number of nitrogen atoms in this ring is 0-2.

3. The compound as claimed in claim 1, wherein
K is selected from a bond, O, CO, OCH₂, CH₂O, N(R36)CO, CON(R37), (C(R38)(R39))₂, (R31)C=C(R32), C≡C, SCH₂, or SO₂CH₂, wherein R31, R32, R36, R37, R38, and R39 are, independently of one another, H or (C₁-C₈)-alkyl.

4. The compound as claimed in claim 1, wherein
R2 is (C₁-C₈)-alkyl, (C₁-C₄)-alkoxy-(C₁-C₄)-alkyl, a 3 to 10-membered mono-, bi-, tri- or spirocyclic ring which may include 0 to 3 heteroatoms selected from the group consisting of oxygen, nitrogen and sulfur, where the ring system may additionally be substituted with one or more of the following substituents: F, Cl, Br, CF₃, CN, (C₁-C₆)-alkyl, O—(C₁-C₈)-alkyl, (C₀-C₂)-alkylene-aryl, oxo, CO(R41), CON(R42)(R43), hydroxy, N(R45)CO(C₁-C₆)-alkyl, N(R46)(R47) SO₂CH₃ (C₁-C₈)-alkyl, (C₁-C₄)-alkoxy-(C₁-C₄)-alkyl, a 3 to 10-membered mono- or bicyclic ring which may include 0 to 2 heteroatoms selected from the group consisting of oxygen, nitrogen and sulfur, where the ring system may additionally be substituted with one or more of the following substituents: F, Cl, Br, CF₃, CN, (C₁-C₆)-alkyl, O—(C₁-C₈)-alkyl, oxo, CO(R41), CON(R42)(R43), N(R45)CO(C₁-C₆)-alkyl and SO₂CH₃;
R41, R42, R43, R45, R46, and R47 are, independently of one another, H or (C₁-C₈)-alkyl;
or, alternatively,
R42 and R43, R46 and R47 form, independently of one another, optionally together with the nitrogen atom to which they are bonded, a 5-6 membered ring which, apart from the nitrogen atom, may also include 1 further heteroatom-containing members selected from the group consisting of NH, N—(C₁-C₆)-alkyl, oxygen and sulfur.

5. The compound as claimed in claim 1, wherein
A, B, D, and G are C(R3), wherein
R3 is H, F, Cl, Br, CF₃, CN, O—(C₁-C₆)-alkyl, O—(C₁-C₄)-alkoxy-(C₁-C₄)-alkyl, S—(C₁-C₆)-alkyl, (C₁-C₆)-alkyl, (C₀-C₈)-alkylene-aryl, O—(C₀-C₈)-alkylene-aryl, N(R4)(R5), SO₂—CH₃, CON(R6)(R7), N(R8)CO(R9), CO(R12), or (CR13R14)$_x$—O(R15);

R4, R5, R6, R7, and R8 are, independently of one another, H, or $(C_1-C_8)$-alkyl;

or, alternatively,

R4 and R5, R6 and R7, independently of one another, optionally together with the nitrogen atom to which they are bonded, form a 5-6 membered ring which, apart from the nitrogen atom, may also include 1 further heteroatom selected from the group consisting of NH, N—$(C_1-C_6)$-alkyl, oxygen and sulfur;

R9 and R12 are, independently of one another, H or $(C_1-C_8)$-alkyl;

R13 and R14 are each H;

R15 is H or $(C_1-C_6)$-alkyl;

X is 0, 1 or 2.

6. The compound as claimed in claim 1, wherein X is a bond or N(R16), in which R16 is H or $(C_1-C_8)$-alkyl.

7. A medicament comprising one or more of the compounds of formula I as claimed in claim 1.

8. A medicament comprising one or more of the compounds of formula I as claimed in claim 1 and one or more active ingredients which have beneficial effects on metabolic disturbances or disorders associated therewith.

9. A medicament comprising one or more of the compounds of formula I as claimed in claim 1 and one or more antidiabetics.

10. A medicament comprising one or more of the compounds of formula I as claimed in claim 1 and one or more lipid modulators.

11. The compound as claimed in claim 1, wherein Q is selected from:

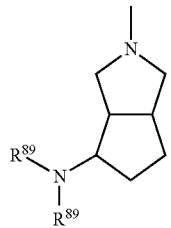 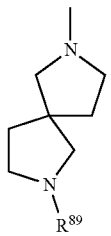 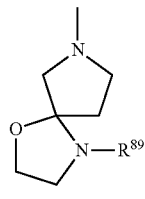

-continued

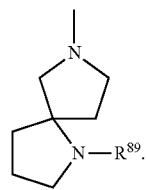

12. The compound as claimed in claim 1, wherein Q is selected from:

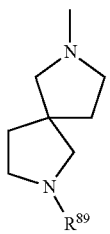 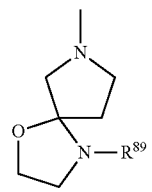 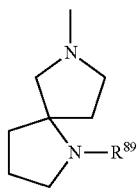

13. The compound as claimed in claim 3, wherein K is selected from $OCH_2$, $CH_2O$, N(R36)CO, CON(R37), $(C(R38)(R39))_2$, (R31)C=C(R32), C≡C, $SCH_2$, and $SO_2CH_2$, wherein R31, R32, R36, R37, R38, and R39 are, independently of one another, H or $(C_1-C_8)$-alkyl.

14. The compound as claimed in claim 3, wherein K is selected from $OCH_2$, $CH_2O$, CON(R37), $(C(R38)(R39))_2$, C≡C, and $SCH_2$, wherein R31, R32, R36, R37, R38, and R39 are, independently of one another, H or $(C_1-C_8)$-alkyl.

* * * * *